United States Patent
Dickhaut et al.

(10) Patent No.: US 11,578,083 B2
(45) Date of Patent: *Feb. 14, 2023

(54) PYRIMIDINIUM COMPOUNDS AND THEIR MIXTURES FOR COMBATING ANIMAL PESTS

(71) Applicant: BASF SE, Ludwigshafen am Rhein (DE)

(72) Inventors: Joachim Dickhaut, Ludwigshafen (DE); Ashokkumar Adisechan, Navi Mumbai (IN); Gopal Krishna Datta, Goettingen (DE); Olesya Kuzmina, Ludwigshafen (DE); Juergen Langewald, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 486 days.

This patent is subject to a terminal disclaimer.

(21) Appl. No.: 16/497,935

(22) PCT Filed: Mar. 26, 2018

(86) PCT No.: PCT/EP2018/057578
§ 371 (c)(1),
(2) Date: Sep. 26, 2019

(87) PCT Pub. No.: WO2018/177970
PCT Pub. Date: Oct. 4, 2018

(65) Prior Publication Data
US 2021/0355139 A1    Nov. 18, 2021

(30) Foreign Application Priority Data

Mar. 31, 2017  (EP) .................................. 17164175
Apr. 27, 2017  (EP) .................................. 17168354
May 3, 2017    (EP) .................................. 17169294
Aug. 31, 2017  (EP) .................................. 17188677
Jan. 17, 2018  (EP) .................................. 18152000

(51) Int. Cl.
| | |
|---|---|
| *A01N 37/30* | (2006.01) |
| *A01N 37/34* | (2006.01) |
| *A01N 43/40* | (2006.01) |
| *A01N 43/56* | (2006.01) |
| *A01N 43/653* | (2006.01) |
| *A01N 43/707* | (2006.01) |
| *A01N 43/80* | (2006.01) |
| *A01N 43/88* | (2006.01) |
| *A01N 43/90* | (2006.01) |
| *A01N 47/34* | (2006.01) |
| *A01P 7/04* | (2006.01) |
| *C07D 513/04* | (2006.01) |

(52) U.S. Cl.
CPC .......... *C07D 513/04* (2013.01); *A01N 37/30* (2013.01); *A01N 37/34* (2013.01); *A01N 43/40* (2013.01); *A01N 43/56* (2013.01); *A01N 43/653* (2013.01); *A01N 43/707* (2013.01); *A01N 43/80* (2013.01); *A01N 43/88* (2013.01); *A01N 43/90* (2013.01); *A01N 47/34* (2013.01); *A01P 7/04* (2021.08)

(58) Field of Classification Search
CPC ........ A01N 37/30; A01N 37/34; A01N 43/40; A01N 43/56; A01N 43/653; A01N 43/707; A01N 43/80; A01N 43/88; A01N 43/90; A01N 47/34; A01P 7/04; C07D 513/04; C07D 277/32; C07D 419/04

See application file for complete search history.

(56) References Cited

U.S. PATENT DOCUMENTS

| | | | | |
|---|---|---|---|---|
| 9,730,451  | B2 * | 8/2017 | Narine ................. | C07D 487/04 |
| 11,034,703 | B2 * | 6/2021 | Shinde ................. | C07D 419/04 |
| 11,124,528 | B2 * | 9/2021 | Shinde ................. | C07D 277/32 |

FOREIGN PATENT DOCUMENTS

WO    WO-2014167084 A1 * 10/2014  .............. A61P 33/00

OTHER PUBLICATIONS

U.S. Appl. No. 17/275,231, filed Sep. 2019, BASF SE.*
U.S. Appl. No. 17/275,225, filed Sep. 2019, BASF SE.*
U.S. Appl. No. 17/274,909, filed Sep. 2019, BASF SE.*

(Continued)

*Primary Examiner* — Amanda L. Aguirre
(74) *Attorney, Agent, or Firm* — Marshall, Gerstein & Borun LLP

(57) ABSTRACT

The present invention relates to pyrimidinium compounds of formula (I), to the stereoisomers, salts, tautomers and N-oxides thereof, their mixtures and to compositions comprising such compounds or mixtures. The invention also relates to methods and uses of these pyrimidinium compounds and of compositions thereof, for combating and controlling animal pests. Furthermore, the invention relates also to pesticidal methods of applying such substituted pyrimidinium compounds. The pyrimidinium compounds of the present invention are defined by the following general formula (I):

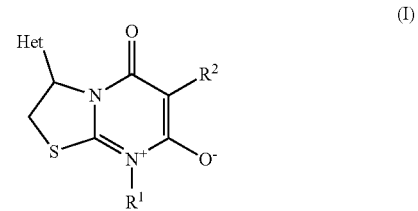

wherein R1, R2 and Het are defined as in the description.

10 Claims, No Drawings

(56) References Cited

OTHER PUBLICATIONS

U.S. Appl. No. 17/270,824, filed Sep. 2019, BASF SE.*
Porter, A. Insecticide Resistance Action Committee, Method No. 019, "IRAC Susceptibility Test Method Series", published online Dec. 15, 2016 [downloaded May 3, 2022] from the Internet <https://irac-online.org/content/uploads/Method_019-_v3.4_15Dec16_aphid.pdf>. (Year: 2016).*
WebMD "Pyrethrum: Overview, Uses, Side Effects, Precautions, Interactions, Dosing and Reviews." Therapeutic Research Faculty, 2020 [downloaded Apr. 19, 2022] from the Internet <https://www.webmd.com/vitamins/ai/ingredientmono-387/pyrethrum>. (Year: 2020).*
Teng et al. "Evaluation of the sublethal effect of tetrachlorantraniliprole on Spodoptera exigua and its potential toxicity to two non-target organisms." PLoS ONE 2020, 15(11): e0242052. (Year: 2020).*

* cited by examiner

PYRIMIDINIUM COMPOUNDS AND THEIR MIXTURES FOR COMBATING ANIMAL PESTS

This application is a National Stage application of International Application No. PCT/EP2018/057578, filed Mar. 26, 2018. This application also claims priority under 35 U.S.C. § 119 to European Patent Application No. 17164175.6, filed Mar. 31, 2017; European Patent Application No. 17168354.3, filed Apr. 27, 2017; European Patent Application No. 17169294.0, filed May 3, 2017; European Patent Application No. 17188677.3, filed Aug. 31, 2017; and European Patent Application No. 18152000.8, filed Jan. 17, 2018.

The present invention relates to insecticidal pyrimidinium compounds and/or to the compositions comprising such compounds for combating invertebrate pests. The present invention relates further to mixtures of these compounds with further active ingredient(s) having synergistically enhanced action. The invention also relates to pesticidal methods, to uses and to applications of the pyrimidinium compounds as described in the present invention and the stereoisomers, salts, tautomers and N-oxides thereof as well as of their mixtures and compositions comprising them.

Invertebrate pests and in particular insects, arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control insects, arachnids and nematodes.

It has been found that these objectives can be achieved by pyrimidinium compounds of the general formula (I), as defined below, including their stereoisomers, their salts, in particular their agriculturally or veterinary acceptable salts, their tautomers and their N-oxides.

The present invention relates to pyrimidinium compounds of formula (I)

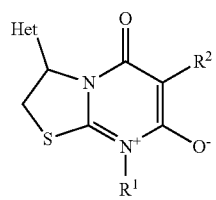

(I)

wherein $R^1$ is $C_1$-$C_4$-alkyl, $C_3$-$C_6$-cycloalkyl, $C_2$-$C_4$-alkenyl or benzyl, which groups may be partially or fully substituted with halogen or $C_1$-$C_4$-alkyl;

$R^2$ is a five- or six membered carbo- or heterocyclic ring, which ring may be unsubstituted, partially, or fully substituted with $R^{2a}$;

Het is selected from D-1, D-2 and D-3:

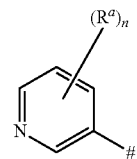

D-1

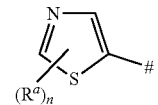

D-2

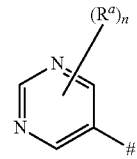

D-3 wherein $R^a$ is halogen, $C_1$-$C_4$-haloalkyl, $C_1$-$C_4$-alkoxy or $C_1$-$C_4$-alkylthio or phenyl, n is 0, 1 or 2, and # denotes the bond in formula (I);

$R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl, which may be substituted with halogen, $C_1$-$C_6$-haloalkyl or $C_1$-$C_6$-haloalkoxy;

$R^b$ is each independently hydrogen, $C_1$-$C_6$-alkyl, $C_1$-$C_6$-haloalkyl, $C_1$-$C_6$-alkoxy, $C_1$-$C_6$-haloalkoxy;

$R^c$ is each independently hydrogen, $C_1$-$C_4$-alkyl, $C_1$-$C_4$-haloalkyl, $C_1$-$C_6$ cycloalkyl;

wherein two geminally bound groups $R^bR^b$, $R^cR^b$ or $R^cR^c$ together with the atom to which they are bound, may form a 3-, 4-, 5-, 6- or 7-membered saturated, partially unsaturated or aromatic carbo- or heterocyclic ring;

or a stereoisomer, tautomer, salt, or N-oxide thereof.

WO2014/167084 describes certain substituted pyrimidinium compounds for combating invertebrate pests.

The present invention also relates to non-racemic compounds of formula (I), wherein the variables Het, $R^1$, and $R^2$ are as defined in compound of formula (I);

The present invention also relates to the compounds of formula (I) with enantiomeric excess of formula (I-R), wherein the variables Het, $R^1$, and $R^2$ are as defined in compound of formula (I);

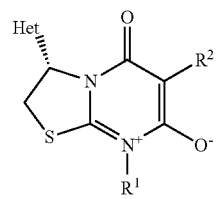

(I-R)

The pyrimidinium compounds of the formula (I), the non-racemic compounds of the formula (I), or the compound of formula (I) with enantiomeric excess of compound of formula I-R, and their agriculturally acceptable salts are highly active against animal pest, i.e. harmful arthropods and nematodes, especially against insects and acaridae which are difficult to control by other means.

Moreover, the present invention relates to and includes the following embodiments:

compositions comprising at least one compound of formula (I), or the non-racemic compounds of the formula (I), or the compound of formula (I) with enantiomeric excess of compound of formula I-R, as defined above and herein below;

agricultural and veterinary compositions comprising an amount of at least one compound of formula (I), or the non-racemic compounds of the formula (I), or the compound of formula (I) with enantiomeric excess of compound of formula I-R, or an enantiomer, diasteromer or salt thereof as defined above and herein below;

a method for combating invertebrate pests, infestation, or infection by invertebrate pests, which method comprises contacting said pest or its food supply, habitat or breeding grounds with a pesticidally effective amount of at least one compound of formula (I), or the non-racemic compounds of the formula (I), or the compound of formula (I) with enantiomeric excess of compound of formula I-R, as defined above and herein below or a composition thereof;

a method for controlling invertebrate pests, infestation, or infection by invertebrate pests, which method comprises contacting said pest or its food supply, habitat or breeding grounds with a pesticidally effective amount of at least one compound of formula (I), or the non-racemic compounds of the formula (I), or the compound of formula (I) with enantiomeric excess of compound of formula I-R, as defined above and herein below, or a composition comprising at least one compound of formula (I) or the non-racemic compounds of the formula (I) or the compound of formula (I) with enantiomeric excess of compound of formula I-R;

a method for preventing or protecting against invertebrate pests comprising contacting the invertebrate pests, or their food supply, habitat or breeding grounds with a substituted pyrimidinium compounds of the general formula (I), or the non-racemic compounds of the formula (I), or the compound of formula (I) with enantiomeric excess of compound of formula I-R, as defined above and herein below, or a composition comprising at least one compound of formula (I) or or the non-racemic compounds of the formula (I) or the compound of formula (I) with enantiomeric excess of compound of formula I-R, as defined above and herein below, or a composition comprising at least one compound of formula (I) or the non-racemic compounds of the formula (I) or the compound of formula (I) with enantiomeric excess of compound of formula I-R;

a method for protecting crops, plants, plant propagation material and/or growing plants from attack or infestation by invertebrate pests comprising contacting or treating the crops, plants, plant propagation material and growing plants, or soil, material, surface, space, area or water in which the crops, plants, plant propagation material is stored or the plant is growing, with a pesticidally effective amount of at least one compound of formula (I), or the non-racemic compounds of the formula (I), or the compound of formula (I) with enantiomeric excess of compound of formula I-R, as defined above and herein below or a composition comprising at least one compound of formula (I) or the non-racemic compounds of the formula (I) or the compound of formula (I) with enantiomeric excess of compound of formula I-R;

a non-therapeutic method for treating animals infested or infected by parasites or preventing animals of getting infected or infested by parasites or protecting animals against infestation or infection by parasites which comprises orally, topically or parenterally administering or applying to the animals a parasiticidally effective amount of a compound of formula (I), or the non-racemic compounds of the formula (I), or the compound of formula (I) with enantiomeric excess of compound of formula I-R, as defined above and herein below or a composition comprising at least one compound of formula (I) or the non-racemic compounds of the formula (I) or the compound of formula (I) with enantiomeric excess of compound of formula I-R;

a method for treating, controlling, preventing or protecting animals against infestation or infection by parasites by administering or applying orally, topically or parenterally to the animals a substituted pyrimidinium compound of the general formula (I), or the non-racemic compounds of the formula (I), or the compound of formula (I) with enantiomeric excess of compound of formula I-R, as defined above and herein below or a composition comprising at least one compound of formula (I) or the non-racemic compounds of the formula (I) or the compound of formula (I) with enantiomeric excess of compound of formula I-R;

seed comprising a compound of formula (I), or the non-racemic compounds of the formula (I) or the compound of formula (I) with enantiomeric excess of compound of formula I-R, as defined above and herein below, in an amount of from 0.1 g to 10 kg per 100 kg of seed;

the use of the compounds of formula (I), or the non-racemic compounds of the formula (I), or the compound of formula (I) with enantiomeric excess of compound of formula I-R, as defined above and herein below for protecting growing plants or plant propagation material from attack or infestation by invertebrate pests;

the use of compounds of formula (I), or the non-racemic compounds of the formula (I), or the compound of formula (I) with enantiomeric excess of compound of formula I-R, or the enantiomers, diastereomers or veterinary acceptable salts thereof for combating parasites in and on animals;

a process for the preparation of a veterinary composition for treating, controlling, preventing or protecting animals against infestation or infection by parasites which comprises adding a parasiticidally effective amount of a compound of formula (I), or the non-racemic compounds of the formula (I), or the compound of formula (I) with enantiomeric excess of compound of formula I-R, as defined herein or the enantiomers, diastereomers and/or veterinary acceptable salt thereof to a carrier composition suitable for veterinary use;

the use of a compound of formula (I), or the non-racemic compounds of the formula (I), or the compound of formula (I) with enantiomeric excess of compound of formula I-R, as defined herein or the enantiomers, diastereomers and/or veterinary acceptable salt thereof for the preparation of a medicament for treating, controlling, preventing or protecting animals against infestation or infection by parasites.

Moreover, the present invention also relates to and includes the following embodiments:

a compound of formula (I), or the non-racemic compounds of the formula (I), or the compound of formula (I) with enantiomeric excess of compound of formula I-R, as defined herein for use in controlling rice pests, especially rice pest invertebrates, in rice;

compositions comprising at least one compound of formula (I), or the non-racemic compounds of the formula (I), or the compound of formula (I) with enantiomeric excess of compound of formula I-R, as defined herein, for use in controlling rice pests, especially rice pest invertebrates, in rice;

agricultural compositions comprising an amount of at least one compound of formula (I), or the non-racemic compounds of the formula (I), or the compound of formula (I) with enantiomeric excess of compound of formula I-R, as defined herein or an enantiomer, diasteromer or salt thereof as defined above, for use in controlling rice pests, especially rice pest invertebrates, in rice;

a method for combating rice pest invertebrates, infestation, or infection by rice pest invertebrates, which method comprises contacting said pest or its food supply, habitat or breeding grounds with a pesticidally effective amount of at least one compound of formula (I), or the non-racemic compounds of the formula (I), or the compound of formula (I) with enantiomeric excess of compound of formula I-R, as defined above and herein below or a composition thereof;

a method for controlling rice pest invertebrates, infestation, or infection by invertebrate pests, which method comprises contacting said pest or its food supply, habitat or breeding grounds with a pesticidally effective amount of at least one compound of formula (I), or the non-racemic compounds of the formula (I), or the compound of formula (I) with enantiomeric excess of compound of formula I-R, as defined above and herein below, or a composition comprising at least one compound of formula (I) or the non-racemic compounds of the formula (I) or the compound of formula (I) with enantiomeric excess of compound of formula I-R;

a method for preventing or protecting against rice pest invertebrates comprising contacting the rice pest invertebrates, or their food supply, habitat or breeding grounds with a substituted pyrimidinium compounds of the general formula (I), or the non-racemic compounds of the formula (I), or the compound of formula (I) with enantiomeric excess of compound of formula I-R, as defined above, or a composition comprising at least one compound of formula (I) or the non-racemic compounds of the formula (I) or the compound of formula (I) with enantiomeric excess of compound of formula I-R, as defined above and herein below;

a method for protecting rice, rice plants, rice plant propagation material and/or growing rice plants from attack or infestation by rice pest invertebrates comprising contacting or treating the rice, rice plants, rice plant propagation material and growing rice plants, or soil, material, surface, space, area or water in which the rice, rice plants, rice plant propagation material is stored or the rice plant is growing, with a pesticidally effective amount of at least one compound of formula (I), or the non-racemic compounds of the formula (I), or the compound of formula (I) with enantiomeric excess of compound of formula I-R, as defined above and herein below, or a composition comprising at least one compound of formula (I) or the non-racemic compounds of the formula (I) or the compound of formula (I) with enantiomeric excess of compound of formula I-R;

a method for increasing the health of rice plants, especially in paddy rice fields, comprising the treatment with at least one compound of formula (I), or the non-racemic compounds of the formula (I), or the compound of formula (I) with enantiomeric excess of compound of formula I-R, as defined herein;

a method for increasing the yield of rice plants, comprising the treatment with at least one compound of formula (I), or the non-racemic compounds of the formula (I), or the compound of formula (I) with enantiomeric excess of compound of formula I-R, as defined herein;

rice seed comprising a compound of formula (I), or the non-racemic compounds of the formula (I), or the compound of formula (I) with enantiomeric excess of compound of formula I-R, as defined above and herein below, in an amount of from 0.1 g to 10 kg per 100 kg of seed;

the use of the compounds of formula (I), or the non-racemic compounds of the formula (I), or the compound of formula (I) with enantiomeric excess of compound of formula I-R, as defined above and herein below for protecting growing rice plants or rice plant propagation material from attack or infestation by rice pest invertebrates;

All the compounds of the present invention including if applicable their stereoisomers, their tautomers, their salts or their N-oxides as well as compositions thereof are particularly useful for controlling invertebrate pests, in particular for controlling arthropods and nematodes and especially insects. Therefore, the invention relates to the use of a compound as disclosed in the present invention, for combating or controlling invertebrate pests, in particular invertebrate pests of the group of insects, arachnids or nematodes.

The term "compound(s) according to the invention" or "compound(s) of formula (I)" as used in the present invention refers to and comprises the compound(s) as defined herein and/or stereoisomer(s), salt(s), tautomer(s) or N-oxide(s) thereof. The term "compound(s) of the present invention" is to be understood as equivalent to the term "compound(s) according to the invention", therefore also comprising stereoisomer(s), salt(s), tautomer(s) or N-oxide(s) of compounds of formula (I).

The term "compound(s) I-R" or "compound(s) of formula (I-R)" as used in herein are synonyms.

The term "composition(s) according to the invention" or "composition(s) of the present invention" encompasses composition(s) comprising at least one compound of formula (I) or the compound of formula (I) with enantiomeric excess of compound of formula I-R, according to the invention as defined above, therefore also including a stereoisomer, an agriculturally or veterinary acceptable salt, tautomer or an N-oxide of the compounds of formula (I).

The compounds of the formula (I) are present in mesomeric forms. These forms may be expressed in different isoelectronic formulae, each having the formal positive and negative charges on different atoms (as shown below). The present invention extends to all representative isoelectronic structures of compounds of formula I.

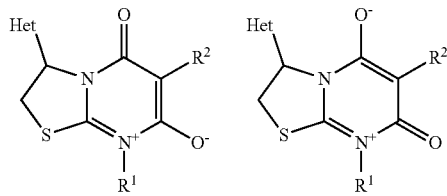

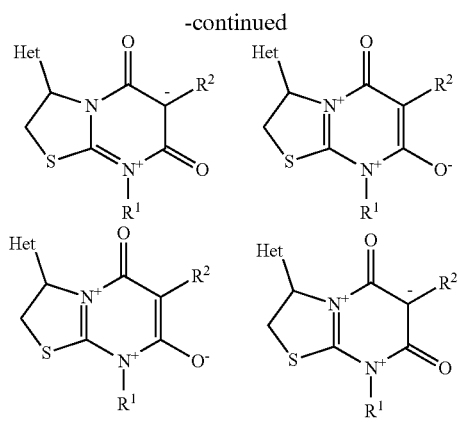

The compounds of the formula (I) have one or, depending on the substitution pattern, more centers of chirality, in which case they are present as mixtures of enantiomers or diastereomers. The invention provides both the single pure enantiomers or pure diastereomers of the compounds of formula (I), and their mixtures and the use according to the invention of the pure enantiomers or pure diastereomers of the compound of formula (I) or its mixtures. Suitable compounds of the formula (I) also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula (I), i.e. to single enantiomers or diastereomers, as well as to mixtures thereof. Preferred embodiments of specific enantiomers are described in more detail below, as compounds of formula (I-R) and (I-S).

Depending on the substitution pattern, the compounds of the formula (I) may be present in the form of their tautomers. Hence the invention also relates to the tautomers of the formula (I) and the stereoisomers, salts, tautomers and N-oxides of said tautomers.

Salts of the compounds of the formula (I) are preferably agriculturally and/or veterinary acceptable salts. They can be formed in a customary method, e.g. by reacting the compound with an acid of the anion in question if the compound of formula (I) has a basic functionality or by reacting an acidic compound of formula (I) with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxy-alkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The term "N-oxide" includes any compound of the present invention which has at least one tertiary nitrogen atom that is oxidized to an N-oxide moiety.

The organic moieties groups mentioned in the above definitions of the variables are—like the term halogen—collective terms for individual listings of the individual group members. The prefix $C_n$-$C_m$ indicates in each case the possible number of carbon atoms in the group.

The organic moieties may have further substituents attached to them, i.e. the organic moieties may be "substituted with" other moieties (e.g. halogen, fluoro, alkyl), which is some-times expressed also as "substituted by", but has the same meaning in this context.

"Halogen" denotes in each case fluorine, bromine, chlorine or iodine, in particular fluorine, chlorine, or bromine.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl, or 1,1-dimethylethyl.

The term "$C_n$-$C_m$-haloalkyl" as used herein refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl. In this context, the alkyl moiety is said to be substituted with halogen or fluoro, which is sometimes expressed also as "substituted by" halogen or fluoro.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen (or sulfur linkages, respectively) at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the term "$C_n$-$C_m$-haloalkoxy" refers to straight-chain or branched alkyl groups having n to m carbon atoms, e.g. 1 to 10, in particular 1 to 6 or 1 to 4 carbon atoms (as mentioned above) bonded through oxygen linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloro-methoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy. Similarly the terms $C_1$-$C_2$-fluoroalkoxy refer to $C_1$-$C_2$-fluoroalkyl which is bound to the remainder of the molecule via an oxygen atom.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-di-methyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "aryl" as used herein refers to a mono-, bi- or tricyclic aromatic hydrocarbon radical such as phenyl or naphthyl, in particular phenyl (also referred as to $C_6H_5$ as substituent).

The term "ring system" denotes two or more directly connected rings.

The term "$C_3$-$C_m$-cycloalkyl" as used herein refers to a monocyclic ring of 3- to m-membered saturated cycloaliphatic radicals, e.g. cyclopropyl, cyclobutyl, cyclopentyl, cyclohexyl, cycloheptyl, cyclooctyl and cyclodecyl.

The term "five- or six-membered carbo- or heterocyclic ring" as used herein refers to saturated, partially unsaturated or aromatic rings which may contain 1, 2, 3 or 4 heteroatoms or heteroatom groups, wherein those heteroatom(s) (group(s)) are selected from N (N-substituted groups), O and S (S-substituted groups) as used herein refers to monocyclic radicals, the monocyclic radicals being saturated, partially unsaturated or aromatic (completely unsaturated). The heterocyclic radical may be attached to the remainder of the molecule via a carbon ring member or via a nitrogen ring member.

Examples of five- or six-membered carbo- or heterocyclic rings include cyclopentane and cyclohexane, cyclohexen, phenyl, pyridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin 5 yl, 1,2,4-thiadiazolidin-3-yl, 1,2,4-thiadiazolidin-5-yl, 1,2,4-triazolidin-3-yl,-1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-di-oxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, and the like.

Examples of 5- or 6-membered partially unsaturated heterocyclyl or heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin 3 yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydro-pyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl.

Examples of 5- or 6-membered aromatic heterocyclic (hetaryl) or heteroaromatic rings are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

Unless specified otherwise the term "at least XX %" refers to ≥XX % to ≤100%, e.g. at least 55% refers to ≥55% to ≤100%.

The term "non-racemic compound(s) of formula (I)" refers to the compound(s) of formula (I) wherein its R- and S-enantiomers are not present in equal amount.

The term "Enantiomeric excess" indicates the excess of an enantiomer in a mixture of enantiomers, and is calculated according to the following formula:

ee=[|$m_1$−$m_2$|/($m_1$+$m_2$)]×100% ee: enantiomeric excess
$m_1$: fraction of enantiomer 1
$m_2$: fraction of enantiomer 2

As used herein and unless otherwise stated, the term "enantiomer" means each individual optically active form of a compound of the invention.

The term "with enantiomeric excess" as used herein refers to a mixture of enantiomers wherein the enantiomer with respect to which the term with "enantiomeric excess" used is present in enantiomeric excess compared to other enantiomer, preferably in an amount of at least 60%, preferably at least 80%, more preferably at least 95%, most preferably at least 98% of the mixture of enantiomers. For example the term "compound of formula I-1 with enantiomeric excess of compound I-R-1" refers to compound of formula I-1 wherein the compound I-R-1 is present in enantiomeric excess amount compared to the compound I-S-1, preferably in an amount of at least 60%, preferably at least 80%, more preferably at least 95%, most preferably at least 98%.

The compounds according to the invention can be prepared as described in WO2014/167084, or as described below. The preparation of the compounds of formula (I) above may lead to them being obtained as isomer mixtures. If desired, these can be resolved by the methods customary for this purpose, such as crystallization or chromatography, also on optically active adsorbate, to give the pure isomers.

Agronomically acceptable salts of the compounds I can be formed in a customary manner, e.g. by reaction with an acid of the anion in question.

Compounds of formula (I) can be prepared analogously to the methods described by Holyoke et al. in WO 2009/099929 (Scheme 1), from appropriately substituted compounds (III).

Scheme 1

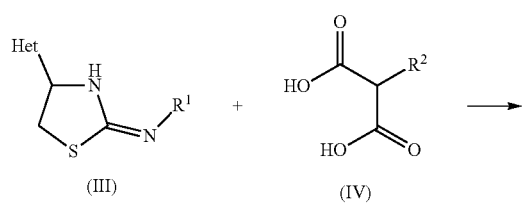

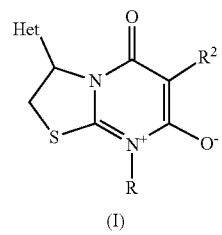

(I)

Compounds (III) can be prepared by methods described e.g. by Brian R. Dixon et al in U.S. Pat. No. 6,353,006 from e.g. 2-chloro ethanamines like compound (V), and analogous methods thereto, with appropriately substituted reactants.

Scheme 2

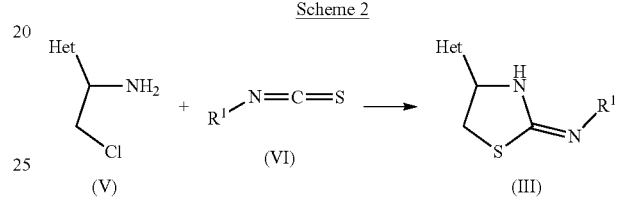

2-Chloro ethanamines compounds (V) in turn are available for example by reduction of sulfinylimines as exemplified in Denolf, Bram et al, Journal of Organic Chemistry, 72(9), 3211-3217; 2007.

Scheme 3

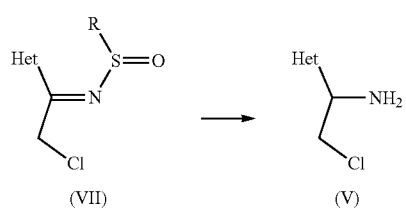

Compounds (VII) are obtained from α-halo-ketones, which are well known to persons skilled in the art.

The compound of formula I with enantiomeric excess can be prepared by the method described below or method analogous to the method described in example section:

The compound of formula I with enantiomeric excess can be prepared by method comprising at least the steps of:
(A) reacting a compound of formula III,

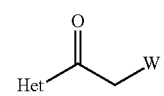

III wherein
W is halogen, O-p-toluenesulfonyl, O-methanesulfonyl, or O-trifluoromethanesulfonyl;
Het is as defined in compound of formula I;
with $M^2OR^{AC}$ wherein $M^2$ is selected from lithium, sodium, potassium, aluminium, barium, caesium, calcium, and magnesium; $R^{AC}$ is C(=O)$C_1$-$C_4$-alkyl;

to obtain the compound of formula IV,

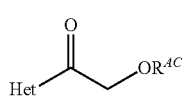

IV wherein Het and $R^{AC}$ are as defined herein;

(B) hydrolyzing the compound of formula IV as defined herein, in the presence of an acid or a base, to obtain a compound of formula V,

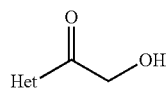

V wherein Het is as defined in compound of formula IV;

(C) reacting the compound of formula V with $X^2SO_2NH_2$ wherein $X^2$ is halogen,
to obtain the compound of formula VI

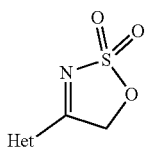

VI wherein Het is as defined in compound of formula V, (D) hydrogenation of the compound of formula VI, in the presence of a hydrogenation catalyst MXLn, wherein
M is a transition metal from group VIII to group XII of the periodic table;
X is an anion;
Ln is Ln1 or Ln2,
wherein
Ln1 is a chiral ligand of the formula Ln1

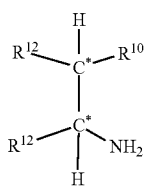

Ln1 wherein
C* is an asymmetric carbon atom of S or R-configuration;
$R^{10}$ is OH or $NH-SO_2-R^{11}$; wherein
$R^{11}$ is aryl unsubstituted or substituted with halogen, $C_1$-$C_{10}$-alkyl, $C_1$-$C_4$-alkoxy, $C_3$-$C_6$-cycloalkyl, $SO_3H$, or $SO_3Na$,
or
$C_1$-$C_{10}$-perfluoroalkyl, or $R^{13}R^{14}N$ wherein $R^{13}$ and $R^{14}$ independently represent $C_1$-$C_{10}$-alkyl unsubstituted or substituted with $C_6$-$C_{10}$-aryl, or $R^{13}$ and $R^{14}$ represent a $C_6$-$C_{10}$-cycloalkyl;

$R^{12}$ independently represents aryl or $C_6$-$C_{10}$-cycloalkyl ring, wherein the ring is unsubstituted or substituted independently of each other with halogen, $C_1$-$C_{10}$-alkyl, $C_1$-$C_4$-alkoxy, $C_3$-$C_6$-cycloalkyl, $SO_3H$, or $SO_3Na$, or both $R^{12}$ are linked together to form a 3- to 6-membered carbocyclic ring or a 5- to 10-membered partially unsaturated carbocyclic ring;

Ln2 is a chiral phosphorous ligand;

and a hydrogen source selected from a) mixture of $N(R)_3$, wherein R is H or $C_1$-$C_6$-alkyl, and HCOOH, b) HCOONa, and c) mixture of isopropyl alcohol, and t-BuOK or t-BuONa or t-BuOLi;

to obtain a compound of formula VII

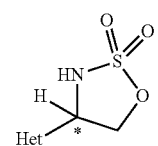

VII wherein

C* is an asymmetric carbon atom of S or R-configuration;

Het is as defined in compound of formula VI, (E) reacting the compound of formula VII,

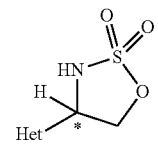

VII wherein

C* is an asymmetric carbon atom of S or R-configuration;

Het is as defined herein;

with $R^1NCS$, wherein $R^1$ is $C_1$-$C_4$-alkyl, $C_3$-$C_6$-cycloalkyl, $C_2$-$C_4$-alkenyl or —$CH_2$-phenyl, which groups unsubstituted or substituted by halogen or $C_1$-$C_4$-alkyl;

in the presence of a base, to obtain a compound of formula VIII,

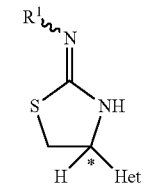

VIII wherein

C* and Het are as defined in the compound of formula VII;

$R^1$ is as defined herein, (F) reacting the compound of formula VIII as defined herein, with a compound of formula IX

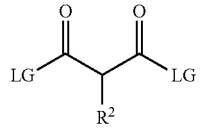

IX wherein,

LG is a leaving group selected from halogen, $OR^u$ or $SR^u$; wherein $R^u$ is halogen, $C_1$-$C_6$-alkyl or aryl, which is unsubstituted or substituted with halogen;

$R^2$ is as defined in the compound of formula I;

to obtain the compound of formula I with enantiomeric excess as defined herein.

Preferences

In one embodiment of the invention, $R^1$ is $C_1$-$C_4$-alkyl, $C_3$-$C_6$-cycloalkyl, $C_2$-$C_4$-alkenyl.

In a further embodiment, $R^1$ is $C_1$-$C_4$-alkyl. In a further embodiment, $R^1$ is methyl or ethyl.

In one embodiment of the invention, $R^2$ is phenyl, pyridinyl or thiophene, which may be unsubstituted, partially, or fully substituted with $R^{2a}$.

In a further embodiment, $R^2$ is phenyl, which may be unsubstituted, partially, or fully substituted with $R^{2a}$, wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl, which may be substituted with halogen, $C_1$-$C_6$-haloalkyl or $C_1$-$C_6$-haloalkoxy.

In a further embodiment, $R^2$ is phenyl, which may be unsubstituted, partially, or fully substituted with halogen, $C_1$-$C_4$-alkyl or $C_1$-$C_3$-haloalkyl.

In a further embodiment, $R^2$ is phenyl, which may be unsubstituted, partially, or fully substituted with trifluoromethyl or halogen, preferably chloro;

In a further embodiment, $R^2$ is phenyl, 3,5-dichlorophenyl, 3-trifluoromethylphenyl.

In a further embodiment, $R^2$ is phenyl.

In a further embodiment, $R^2$ is 3,5-dichlorophenyl.

In a further embodiment, $R^2$ is 3-trifluoromethylphenyl.

In one embodiment of the invention, Het is a five- or six-membered carbo- or heterocyclic aromatic ring.

In one embodiment of the invention, Het is D-2.

In one embodiment of the invention, Het is D-2, wherein $R^a$ is halogen, $C_1$-$C_4$-haloalkyl, $C_1$-$C_4$-alkoxy or $C_1$-$C_4$-alkylthio;

n is 1 or 2.

In one embodiment of the invention, Het is selected from D-1, D-2 and D-3, wherein $R^a$ is chloro, n is 1.

In a further embodiment Het is D-1a, D-2a, and D-3a:

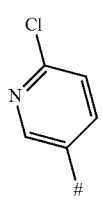

D-1a

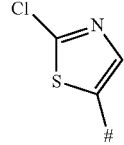

D-2a

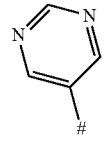

D-3a

In a further embodiment, Het is D-1a.

In a further embodiment, Het is D-2a.

In a further embodiment, Het is D-3a.

In one embodiment of the invention, the compound of formula (I) is one of the following compounds I-1 to I-6:

| Compound No | $R^1$ | $R^2$ | Het |
|---|---|---|---|
| I-1 | $CH_3$ | Ph | D-2a |
| I-2 | $CH_3$ | Ph | D-1a |
| I-3 | $CH_3$ | Ph | D-3a |
| I-4 | $CH_3$ | 3-(trifluoromethyl)phenyl | D-2a |
| I-5 | $CH_3$ | 3,5-dichlorophenyl | D-2a |
| I-6 | $CH_2CH_3$ | Ph | D-2a |

In one embodiment of the invention, the compound of formula (I) is the compound I-1.

In one embodiment of the invention, the compound of formula (I) is the compound I-2.

In one embodiment of the invention, the compound of formula (I) is the compound I-3.

In one embodiment of the invention, the compound of formula (I) is the compound I-4.

In one embodiment of the invention, the compound of formula (I) is the compound I-5.

In one embodiment of the invention, the compound of formula (I) is the compound I-6.

In one embodiment of the invention, the compounds of formula (I) have the following stereochemistry as in formula (I-R):

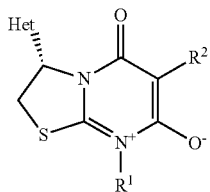

(I-R)

The compounds of formula (I-R) show a higher pesticidal efficacy compared to their stereoisomers of formula (I-S), as is proven by biological examples. Selectivity of compounds (I-R) is different than the selectivity of compounds (1-S) towards biological targets like enzymes or receptors.

In a further embodiment, the compounds according to the invention have the stereochemistry as in formula (I-R) and $R^1$ is $C_1$-$C_4$-alkyl, $C_3$-$C_6$-cycloalkyl, $C_2$-$C_4$-alkenyl, preferably $R^1$ is $C_1$-$C_4$-alkyl, preferably $R^1$ is methyl or ethyl.

In a further embodiment, the compounds according to the invention have the stereochemistry as in formula (I-R) and $R^2$ is phenyl, pyridinyl or thiophene, which may be unsubstituted, partially, or fully substituted with $R^{2a}$, wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl, which may be substituted with halogen, $C_1$-$C_6$-haloalkyl or $C_1$-$C_6$-haloalkoxy.

In a further embodiment, the compounds according to the invention have the stereochemistry as in formula (I-R) and $R^2$ is phenyl, which may be unsubstituted, partially, or fully substituted with $R^{2a}$ as defined above.

In a further embodiment, the compounds according to the invention have the stereochemistry as in formula (I-R) and $R^2$ is phenyl, which may be unsubstituted, partially, or fully substituted with halogen, $C_1$-$C_4$-alkyl or $C_1$-$C_3$-haloalkyl; preferably $R^2$ is phenyl, which may be unsubstituted, partially, or fully substituted with trifluoromethyl or halogen, preferably chloro.

In a further embodiment, the compounds according to the invention have the stereochemistry as in formula (I-R) and $R^2$ is phenyl, 3,5-dichlorophenyl, 3-trifluoromethylphenyl.

In a further embodiment, the compounds according to the invention have the stereochemistry as in formula (I-R) and $R^2$ is phenyl.

In a further embodiment, the compounds according to the invention have the stereochemistry as in formula (I-R) and $R^2$ is 3,5-dichlorophenyl.

In a further embodiment, the compounds according to the invention have the stereochemistry as in formula (I-R) and $R^2$ is 3-trifluoromethylphenyl.

In further embodiment of the invention, Het is D-2.

In further embodiment of the invention, Het is D-2, wherein
$R^a$ is halogen, $C_1$-$C_4$-haloalkyl, $C_1$-$C_4$-alkoxy or $C_1$-$C_4$-alkylthio;
n is 1 or 2.

In a further embodiment, the compounds according to the invention have the stereochemistry as in formula (I-R) and Het is selected from D-1, D-2 and D-3, wherein $R^a$ is chloro, n is 1.

In a further embodiment, the compounds according to the invention have the stereochemistry as in formula (I-R) and Het is D-1a, D-2a or D-3a;

In a further embodiment, the compounds according to the invention have the stereochemistry as in formula (I-R) and Het is D-1a.

In a further embodiment, the compounds according to the invention have the stereochemistry as in formula (I-R) and Het is D-2a.

In a further embodiment, the compounds according to the invention have the stereochemistry as in formula (I-R) and Het is D-3a.

In one embodiment of the invention, the compound of formula (I) is one of the following compounds I-R-1 to I-R-6:

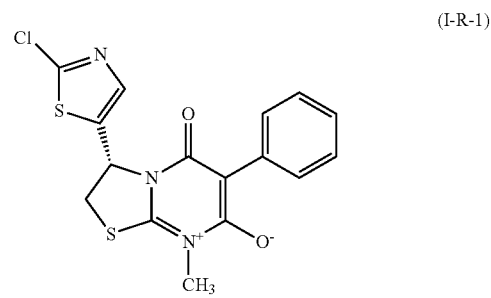

(I-R-1)

(I-R-2)

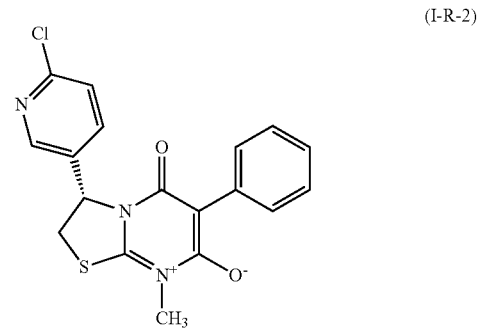

(I-R-3)

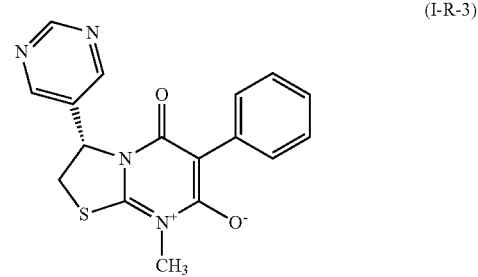

(I-R-4)

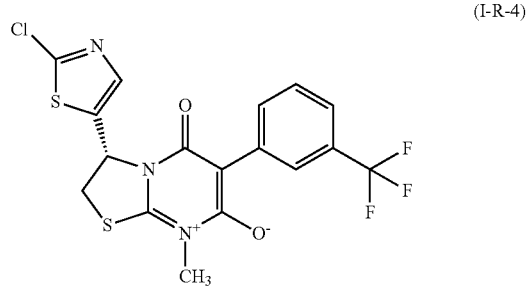

-continued

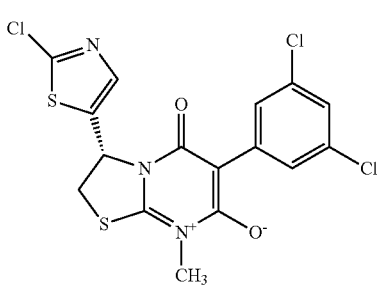
(I-R-5)

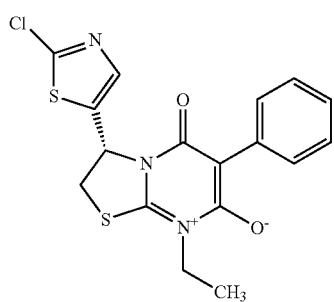
(I-R-6)

In one embodiment of the invention, the compound of formula (I) is the compound I-R-1.

In one embodiment of the invention, the compound of formula (I) is the compound I-R-2.

In one embodiment of the invention, the compound of formula (I) is the compound I-R-3.

In one embodiment of the invention, the compound of formula (I) is the compound I-R-4.

In one embodiment of the invention, the compound of formula (I) is the compound I-R-5.

In one embodiment of the invention, the compound of formula (I) is the compound I-R-6.

In one embodiment of the invention, the compounds of formula (I) refer to the compound of formula (I) with enantiomeric excess of formula (I-R), wherein the variables Het, $R^1$, and $R^2$ are as defined in compound of formula (I);

In one embodiment of the invention, the compounds of formula (I) refer to the compound of formula (I) with enantiomeric excess of at least 55% of formula (I-R);

In one embodiment of the invention, the compounds of formula (I) refer to the compound of formula (I) with enantiomeric excess of at least 60% of formula (I-R);

In one embodiment of the invention, the compounds of formula (I) refer to the compound of formula (I) with enantiomeric excess of at least 65% of formula (I-R);

In one embodiment of the invention, the compounds of formula (I) refer to the compound of formula (I) with enantiomeric excess of at least 70% of formula (I-R);

In one embodiment of the invention, the compounds of formula (I) refer to the compound of formula (I) with enantiomeric excess of at least 75% of formula (I-R);

In one embodiment of the invention, the compounds of formula (I) refer to the compound of formula (I) with enantiomeric excess of at least 80% of formula (I-R);

In one embodiment of the invention, the compounds of formula (I) refer to the compound of formula (I) with enantiomeric excess of at least 85% of formula (I-R);

In a preferred embodiment of the invention, the compounds of formula (I) refer to the compound of formula (I) with enantiomeric excess of at least 90% of formula (I-R);

In another preferred embodiment of the invention, the compounds of formula (I) refer to the compound of formula (I) with enantiomeric excess of at least 95% of formula (I-R);

In another preferred embodiment of the invention, the compounds of formula (I) refer to the compound of formula (I) with enantiomeric excess of at least 98% of formula (I-R);

In another preferred embodiment of the invention, the compounds of formula (I) refer to the compound of formula (I) with enantiomeric excess of at least 99% of formula (I-R);

In another embodiment of the invention, the compounds of formula (I) have the following stereochemistry as in formula (I-S):

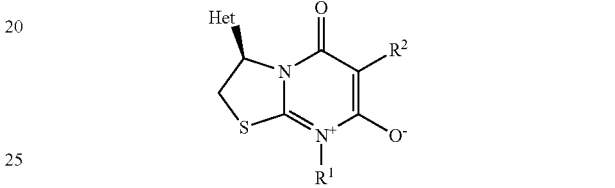
(I-S)

In a further embodiment, the compounds according to the invention have the stereochemistry as in formula (I-S) and $R^1$ is $C_1$-$C_4$-alkyl, $C_3$-$C_6$-cycloalkyl, $C_2$-$C_4$-alkenyl, preferably $R^1$ is $C_1$-$C_4$-alkyl, preferably $R^1$ is methyl or ethyl.

In a further embodiment, the compounds according to the invention have the stereochemistry as in formula (I-S) and $R^2$ is phenyl, pyridinyl or thiophene, which may be unsubstituted, partially, or fully substituted with $R^{2a}$, wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl, which may be substituted with halogen, $C_1$-$C_6$-haloalkyl or $C_1$-$C_6$-haloalkoxy.

In a further embodiment, the compounds according to the invention have the stereochemistry as in formula (I-S) and $R^2$ is phenyl, which may be unsubstituted, partially, or fully substituted with $R^{2a}$ as defined above.

In a further embodiment, the compounds according to the invention have the stereochemistry as in formula (I-S) and $R^2$ is phenyl, which may be unsubstituted, partially, or fully substituted with halogen, $C_1$-$C_4$-alkyl or $C_1$-$C_3$-haloalkyl; preferably $R^2$ is phenyl, which may be unsubstituted, partially, or fully substituted with trifluoromethyl or halogen, preferably chloro.

In a further embodiment, the compounds according to the invention have the stereochemistry as in formula (I-S) and $R^2$ is phenyl, 3,5-dichlorophenyl, 3-trifluoromethylphenyl.

In a further embodiment, the compounds according to the invention have the stereochemistry as in formula (I-S) and $R^2$ is phenyl.

In a further embodiment, the compounds according to the invention have the stereochemistry as in formula (I-S) and $R^2$ is 3,5-dichlorophenyl.

In a further embodiment, the compounds according to the invention have the stereochemistry as in formula (I-S) and $R^2$ is 3-trifluoromethylphenyl.

In a further embodiment, the compounds according to the invention have the stereochemistry as in formula (I-S) and Het is selected from D-1, D-2 and D-3, wherein $R^a$ is chloro, n is 1.

In a further embodiment, the compounds according to the invention have the stereochemistry as in formula (I-S) and Het is D-1a, D-2a or D-3a;

In a further embodiment, the compounds according to the invention have the stereochemistry as in formula (I-S) and Het is D-1a.

In a further embodiment, the compounds according to the invention have the stereochemistry as in formula (I-S) and Het is D-2a.

In a further embodiment, the compounds according to the invention have the stereochemistry as in formula (I-S) and Het is D-3a.

The compounds of formula (I) with enantiomeric excess of formula (I-R) show a higher pesticidal efficacy compared to the racemic mixture or the compounds of formula (I) with enantiomeric excess of formula (I-S), as is proven by biological examples.

In a further embodiment, the compounds according to the invention are the compounds of formula (I) with enantiomeric excess of formula (I-R), wherein $R^1$ is $C_1$-$C_4$-alkyl, $C_3$-$C_6$-cycloalkyl, $C_2$-$C_4$-alkenyl, preferably $R^1$ is $C_1$-$C_4$-alkyl, preferably $R^1$ is methyl or ethyl.

In a further embodiment, the compounds according to the invention are the compounds of formula (I) with enantiomeric excess of formula (I-R), wherein $R^2$ is phenyl, pyridinyl or thiophene, which may be unsubstituted, partially, or fully substituted with $R^{2a}$, wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl, which may be substituted with halogen, $C_1$-$C_6$-haloalkyl or $C_1$-$C_6$-haloalkoxy.

In a further embodiment, the compounds according to the invention are the compounds of formula (I) with enantiomeric excess of formula (I-R), wherein $R^2$ is phenyl, which may be unsubstituted, partially, or fully substituted with $R^{2a}$ as defined above.

In a further embodiment, the compounds according to the invention are the compounds of formula (I) with enantiomeric excess of formula (I-R), wherein $R^2$ is phenyl, which may be unsubstituted, partially, or fully substituted with halogen, $C_1$-$C_4$-alkyl or $C_1$-$C_3$-haloalkyl; preferably $R^2$ is phenyl, which may be unsubstituted, partially, or fully substituted with trifluoromethyl or halogen, preferably chloro.

In a further embodiment, the compounds according to the invention are the compounds of formula (I) with enantiomeric excess of formula (I-R), wherein $R^2$ is phenyl, 3,5-dichlorophenyl, 3-trifluoromethylphenyl.

In a further embodiment, the compounds according to the invention are the compounds of formula (I) with enantiomeric excess of formula (I-R), wherein $R^2$ is phenyl.

In a further embodiment, the compounds according to the invention are the compounds of formula (I) with enantiomeric excess of formula (I-R), wherein $R^2$ is 3,5-dichlorophenyl.

In a further embodiment, the compounds according to the invention are the compounds of formula (I) with enantiomeric excess of formula (I-R), wherein $R^2$ is 3-trifluoromethylphenyl.

In a further embodiment, the compounds according to the invention are the compounds of formula (I) with enantiomeric excess of formula (I-R), wherein Het is selected from D-1, D-2 and D-3, wherein $R^a$ is chloro, n is 0 or 1.

In a further embodiment, the compounds according to the invention are the compounds of formula (I) with enantiomeric excess of formula (I-R), wherein Het is D-2;

In a further embodiment, the compounds according to the invention are the compounds of formula (I) with enantiomeric excess of formula (I-R), wherein Het is D-2, wherein $R^a$ is halogen, $C_1$-$C_4$-haloalkyl, $C_1$-$C_4$-alkoxy, or $C_1$-$C_4$-alkylthio;

n is 1 or 2.

In a further embodiment, the compounds according to the invention are the compounds of formula (I) with enantiomeric excess of formula (I-R), wherein Het is D-1a, D-2a, or D-3a;

In a further embodiment, the compounds according to the invention are the compounds of formula (I) with enantiomeric excess of formula (I-R), wherein Het is D-1a.

In a further embodiment, the compounds according to the invention are the compounds of formula (I) with enantiomeric excess of formula (I-R), wherein Het is D-2a.

In a further embodiment, the compounds according to the invention are the compounds of formula (I) with enantiomeric excess of formula (I-R), wherein Het is D-3a.

In one embodiment of the invention, the compound of formula (I) is selected from compounds I-1 to I-6 with enantiomeric excess of R-enantiomer compounds I-R-1 to I-R-6, respectively:

In one embodiment of the invention, the compound of formula (I) is the compound I-1 with enantiomeric excess of compound I-R-1.

In one embodiment of the invention, the compound of formula (I) is the compound I-2 with enantiomeric excess of compound I-R-2.

In one embodiment of the invention, the compound of formula (I) is the compound I-3 with enantiomeric excess of compound I-R-3.

In one embodiment of the invention, the compound of formula (I) is the compound I-4 with enantiomeric excess of compound I-R-4.

In one embodiment of the invention, the compound of formula (I) is the compound I-5 with enantiomeric excess of compound I-R-5.

In one embodiment of the invention, the compound of formula (I) is the compound I-6 with enantiomeric excess of compound I-R-6.

In one embodiment of the invention, the compound of formula (I) is one of the following compounds I-S-1 to I-S-6:

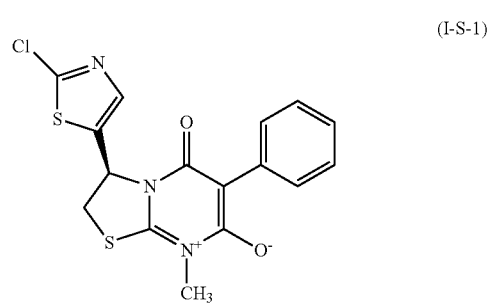

(I-S-1)

-continued

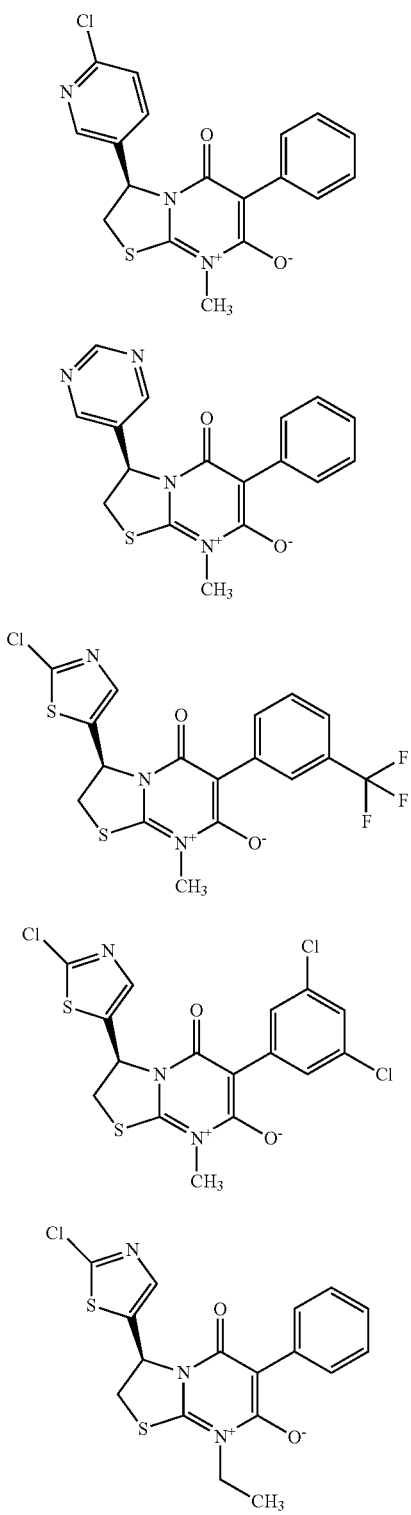

(I-S-2)
(I-S-3)
(I-S-4)
(I-S-5)
(I-S-6)

In one embodiment of the invention, the compound of formula (I) is the compound I-S-1.

In one embodiment of the invention, the compound of formula (I) is the compound I-S-2.

In one embodiment of the invention, the compound of formula (I) is the compound I-S-3.

In one embodiment of the invention, the compound of formula (I) is the compound I-S-4.

In one embodiment of the invention, the compound of formula (I) is the compound I-S-5.

In one embodiment of the invention, the compound of formula (I) is the compound I-S-6.

In one embodiment of the invention, the compounds of formula (I) refer to the compound of formula (I) with enantiomeric excess of formula (I-R), wherein the formula (I-R) is present in an amount from ≥55% to ≤100% and the formula (I-S) is present in an amount from ≤45% to ≥0%;

In one embodiment of the invention, the compounds of formula (I) refer to the compound of formula (I) with enantiomeric excess of formula (I-R), wherein the formula (I-R) is present in an amount from ≥60% to ≤100% and the formula (I-S) is present in an amount from ≤40% to ≥0%;

In one embodiment of the invention, the compounds of formula (I) refer to the compound of formula (I) with enantiomeric excess of formula (I-R), wherein the formula (I-R) is present in an amount from ≥65% to ≤100% and the formula (I-S) is present in an amount from ≤35% to ≥0%;

In one embodiment of the invention, the compounds of formula (I) refer to the compound of formula (I) with enantiomeric excess of formula (I-R), wherein the formula (I-R) is present in an amount from ≥70% to ≤100% and the formula (I-S) is present in an amount from ≤30% to ≥0%;

In one embodiment of the invention, the compounds of formula (I) refer to the compound of formula (I) with enantiomeric excess of formula (I-R), wherein the formula (I-R) is present in an amount from ≥75% to ≤100% and the formula (I-S) is present in an amount from ≤25% to ≥0%;

In one embodiment of the invention, the compounds of formula (I) refer to the compound of formula (I) with enantiomeric excess of formula (I-R), wherein the formula (I-R) is present in an amount from ≥80% to ≤100% and the formula (I-S) is present in an amount from ≤20% to ≥0%;

In one embodiment of the invention, the compounds of formula (I) refer to the compound of formula (I) with enantiomeric excess of formula (I-R), wherein the formula (I-R) is present in an amount from ≥85% to ≤100% and the formula (I-S) is present in an amount from ≤15% to ≥0%;

In another embodiment of the invention, the compounds of formula (I) refer to the compound of formula (I) with enantiomeric excess of formula (I-R), wherein the formula (I-R) is present in an amount from ≥90% to ≤100% and the formula (I-S) is present in an amount from ≤10% to ≥0%;

In another embodiment of the invention, the compounds of formula (I) refer to the compound of formula (I) with enantiomeric excess of formula (I-R), wherein the formula (I-R) is present in an amount from ≥95% to ≤100% and the formula (I-S) is present in an amount from ≤5% to ≥0%;

In another embodiment of the invention, the compounds of formula (I) refer to the compound of formula (I) with enantiomeric excess of formula (I-R), wherein the formula (I-R) is present in an amount from ≥98% to ≤100%, preferably ≥99% to ≤100%, and the formula (I-S) is present in an amount from ≤2% to ≥0%, preferably ≤1% to ≥0%;

Mixtures

One typical problem arising in the field of pest control lies in the need to reduce the dosage rates of the active ingredient in order to reduce or avoid unfavorable environmental or toxicological effects whilst still allowing effective pest control.

Another problem encountered concerns the need to have available pest control agents which are effective against a broad spectrum of pests.

There also exists the need for pest control agents that combine knock-down activity with prolonged control, that is, fast action with long lasting action.

Another difficulty in relation to the use of pesticides is that the repeated and exclusive application of an individual pesticidal compound leads in many cases to a rapid selection of pests which have developed natural or adapted resistance against the active compound in question.

Therefore, there is a need for pest control agents that help prevent or overcome resistance induced by pesticides.

Furthermore, there is a desire for pesticide compounds or combination of compounds, which when applied improve plants, which may result in "plant health", "vitality of plant propagation material" or "increased plant yield".

It is therefore an object of the present invention to provide agricultural combinations which solves one or more than one of the discussed problems as
reducing the dosage rate,
enhancing the spectrum of activity,
combining knock-down activity with prolonged control,
improving resistance management,
Improved plant health;
Improved vitality of plant propagation material, also termed seed vitality;
Increased plant yield It was therefore an object of the present invention to provide pesticidal mixtures which solve at least one of the discussed problems as reducing the dosage rate, enhancing the spectrum of activity or combining knock-down activity with prolonged control or as to resistance management.

It has been found that this object is in part or in whole achieved by the combination of active compounds as defined herein.

Therefore, in a special embodiment of the invention, the compounds according to the invention are mixed with at least one further active ingredient.

As used herein, the term "mixture(s) of the present invention" or "mixture(s) according to the invention" refers to the mixtures comprising compound(s) of formula (I) or the compound of formula (I) with enantiomeric excess of compound of formula (I-R) as defined above, which are also referred to as "compound(s) of formula (I)" or "compound(s) I" or "formula (I) compound(s)", and compound(s) (II) as defined below, which are also referred to as "compound(s) of formula II" or "compound(s) II".

The compounds of formula I or non-racemic compound of formula (I) or compound of formula (I) with enantiomeric excess, and the compounds II are understood to include their salts, tautomers, stereoisomers, and N-oxides.

In one embodiment of the invention, the invention relates to mixtures comprising
(1) at least one compound of formula (I) as defined herein or non-racemic compound of formula (I) or compound of formula (I) with enantiomeric excess of compound of formula (I-R) or (I-S), enantiomers, salts, tautomers, stereoisomers and N-oxides thereof, and
(2) at least one compound II selected from the group of:

M.1 Acetylcholine esterase (AChE) inhibitors: M.1A carbamates, e.g. aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or M.1B organophosphates, e.g. acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxy-aminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, and vamidothion;

M.2. GABA-gated chloride channel antagonists: M.2A cyclodiene organochlorine compounds, e.g. endosulfan or chlordane; or M.2B fiproles (phenylpyrazoles), e.g. ethiprole, fipronil, flufiprole, pyrafluprole, and pyriprole;

M.3 Sodium channel modulators from the class of M.3A pyrethroids, e.g. acrinathrin, allethrin, d-cis-trans allethrin, d-trans allethrin, bifenthrin (in particular kappa-bifenthrin), bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin (in particular epsilon-momfluorothrin), permethrin, phenothrin, prallethrin, profluthrin, pyrethrin (pyrethrum), resmethrin, silafluofen, tefluthrin (in particular kappa-tefluthrin), tetramethylfluthrin, tetramethrin, tralomethrin, and transfluthrin; or M.3B sodium channel modulators such as DDT or methoxychlor;

M.4 Nicotinic acetylcholine receptor agonists (nAChR): M.4A neonicotinoids, e.g. acetamiprid, clothianidin, cycloxaprid, dinotefuran, imidacloprid, nitenpyram, thiacloprid and thiamethoxam; or the compounds M.4A.1 4,5-Dihydro-N-nitro-1-(2-oxiranylmethyl)-1H-imidazol-2-amine, M.4A.2: (2E-)-1-[(6-Chloropyridin-3-yl)methyl]-N'-nitro-2-pentylidenehydrazinecarboximidamide; or M4.A.3: 1-[(6-Chloropyridin-3-yl)methyl]-7-methyl-8-nitro-5-propoxy-1,2,3,5,6,7-hexahydroimidazo[1,2-a]pyridine; or M.4B nicotine; M.4C sulfoxaflor; M.4D flupyradifurone; M.4E triflumezopyrim;

M.5 Nicotinic acetylcholine receptor allosteric activators: spinosyns, e.g. spinosad or spinetoram;

M.6 Chloride channel activators from the class of avermectins and milbemycins, e.g. abamectin, emamectin benzoate, ivermectin, lepimectin, or milbemectin;

M.7 Juvenile hormone mimics, such as M.7A juvenile hormone analogues hydroprene, kinoprene, and methoprene; or M.7B fenoxycarb, or M.7C pyriproxyfen;

M.8 miscellaneous non-specific (multi-site) inhibitors, e.g. M.8A alkyl halides as methyl bromide and other alkyl halides, M.8B chloropicrin, M.8C sulfuryl fluoride, M.8D borax, or M.8E tartar emetic;

M.9 Chordotonal organ TRPV channel modulators, e.g. M.9B pymetrozine; pyrifluquinazon;

M.10 Mite growth inhibitors, e.g. M.10A clofentezine, hexythiazox, and diflovidazin, or M.10B etoxazole;

M.12 Inhibitors of mitochondrial ATP synthase, e.g. M.12A diafenthiuron, or M.12B organotin miticides such as azocyclotin, cyhexatin, or fenbutatin oxide, M.12C propargite, or M.12D tetradifon;

M.13 Uncouplers of oxidative phosphorylation via disruption of the proton gradient, e.g. chlorfenapyr, DNOC, or sulfluramid;

M.14 Nicotinic acetylcholine receptor (nAChR) channel blockers, e.g. nereistoxin analogues bensultap, cartap hydrochloride, thiocyclam, or thiosultap sodium;

M.15 Inhibitors of the chitin biosynthesis type 0, such as benzoylureas e.g. bistrifluron, chlorfluazuron, diflubenzuron, flucycloxuron, flufenoxuron, hexaflumuron, lufenuron, novaluron, noviflumuron, teflubenzuron, or triflumuron;

M.16 Inhibitors of the chitin biosynthesis type 1, e.g. buprofezin;

M.17 Moulting disruptors, Dipteran, e.g. cyromazine;

M.18 Ecdyson receptor agonists such as diacylhydrazines, e.g. methoxyfenozide, tebufenozide, halofenozide, fufenozide, or chromafenozide;

M.19 Octopamin receptor agonists, e.g. amitraz;

M.20 Mitochondrial complex Ill electron transport inhibitors, e.g. M.20A hydramethylnon, M.20B acequinocyl, M.20C fluacrypyrim; or M.20D bifenazate;

M.21 Mitochondrial complex I electron transport inhibitors, e.g. M.21A METI acaricides and insecticides such as fenazaquin, fenpyroximate, pyrimidifen, pyridaben, tebufenpyrad or tolfenpyrad, or M.21 B rotenone;

M.22 Voltage-dependent sodium channel blockers, e.g. M.22A indoxacarb, M.22B metaflumizone, or M.22B.1: 2-[2-(4-Cyanophenyl)-1-[3-(trifluoromethyl)phenyl]ethylidene]-N-[4-(difluoro-methoxy)phenyl]-hydrazinecarboxamide or M.22B.2: N-(3-Chloro-2-methylphenyl)-2-[(4-chloro-phenyl)[4-[methyl(methylsulfonyl)amino]phenyl]methylene]-hydrazinecarboxamide;

M.23 Inhibitors of the of acetyl CoA carboxylase, such as Tetronic and Tetramic acid derivatives, e.g. spirodiclofen, spiromesifen, or spirotetramat; M.23.1 spiropidion M.24 Mitochondrial complex IV electron transport inhibitors, e.g. M.24A phosphine such as aluminium phosphide, calcium phosphide, phosphine or zinc phosphide, or M.24B cyanide;

M.25 Mitochondrial complex II electron transport inhibitors, such as beta-ketonitrile derivatives, e.g. cyenopyrafen or cyflumetofen;

M.28 Ryanodine receptor-modulators from the class of diamides, e.g. flubendiamide, chlorantraniliprole, cyantraniliprole, tetraniliprole, M.28.1: (R)-3-Chlor-N1-{2-methyl-4-[1,2,2,2-tetra-fluoro-1-(trifluoromethyl)ethyl]phenyl}-N2-(1-methyl-2-methylsulfonylethyl)phthalamid, M.28.2: (S)-3-Chloro-N1-{2-methyl-4-[1,2,2,2-tetrafluoro-1-(trifluoromethyl)ethyl]phenyl}-N2-(1-methyl-2-methylsulfonylethyl)phthalamid, M.28.3: cyclaniliprole, or M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide; M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide; M.28.5j) 3-Chloro-1-(3-chloro-2-pyridinyl)-N-[2,4-dichloro-6-[[(1-cyano-1-methylethyl)amino]carbonyl]phenyl]-1H-pyrazole-5-carboxamide; M.28.5k) 3-Bromo-N-[2,4-dichloro-6-(methylcarbamoyl)phenyl]-1-(3,5-dichloro-2-pyridyl)-1H-pyrazole-5-carboxamide; M.28.5l) N-[4-Chloro-2-[[(1,1-dimethylethyl)amino]carbonyl]-6-methyl-phenyl]-1-(3-chloro-2-pyridinyl)-3-(fluoromethoxy)-1H-pyrazole-5-carboxamide; or M.28.6: cyhalodiamide; or M.29: Chordotonal organ Modulators—undefined target site, e.g. flonicamid; M.UN. insecticidal active compounds of unknown or uncertain mode of action, e.g. afidopyropen, afoxolaner, azadirachtin, amidoflumet, benzoximate, broflanilide, bromopropylate, chinomethionat, cryolite, dicloromezotiaz, dicofol, flufenerim, flometoquin, fluensulfone, fluhexafon, fluopyram, fluralaner, metoxadiazone, piperonyl butoxide, pyflubumide, pyridalyl, tioxazafen, M.UN.3: 11-(4-chloro-2,6-dimethylphenyl)-12-hydroxy-1,4-dioxa-9-azadispiro[4.2.4.2]-tetradec-11-en-10-one, M.UN.4: 3-(4'-fluoro-2,4-dimethylbiphenyl-3-yl)-4-hydroxy-8-oxa-1-azaspiro[4.5]dec-3-en-2-one, M.UN.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *Bacillus firmus* (Votivo, 1-1582);

M.UN.6: flupyrimin;

M.UN.8: fluazaindolizine; M.UN.9.a): 4-[5-(3,5-dichlorophenyl)-5-(trifluoromethyl)-4H-isoxazol-3-yl]-2-methyl-N-(1-oxothietan-3-yl)benzamide; M.UN.9.b): fluxametamide; M.UN.10: 5-[3-[2,6-dichloro-4-(3,3-dichloroallyloxy)phenoxy]propoxy]-1H-pyrazole;

M.UN.11.b) 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide; M.UN.11.c) 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide; M.UN.11.d) N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.UN.11.e) N-[3-[[[2-bromo-4-[1,2,2,2-tetrafluoro-1-(trifluoromethyl)ethyl]-6-(trifluoromethyl)phenyl]amino]carbonyl]-2-fluoro-phenyl]-4-fluoro-N-methyl-benzamide; M.UN.11.f) 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.UN.11.g) 3-fluoro-N-[2-fluoro-3-[[[2-iodo-4-[1,2,2,2-tetrafluoro-1-(trifluoromethyl)-ethyl]-6-(trifluoromethyl)phenyl]amino]carbonyl]phenyl]-N-methyl-benzamide; M.UN.11.h) 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide; M.UN.11.i) 4-cyano-N-[2-cyano-5-[[2,6-di-bromo-4-[1,2,2,3,3,3-hexafluoro-1-(trifluoromethyl)propyl]phenyl]carbamoyl]phenyl]-2-methyl-benzamide; M.UN.11.j) 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide; M.UN.11.k) N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide; M.UN.11.l) N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide; M.UN.11.m) N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide; M.UN.11.n) 4-cyano-N-[2- cyano-5-[[2,6-dichloro-4-[1,2,2,3,3,3-hexafluoro-1-(trifluoromethyl)propyl]phenyl]carbamoyl]phenyl]-2-methyl-benzamide; M.UN.11.o) 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide; M.UN.11.p) N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; or M.UN.12.a) 2-(1,3-Dioxan-2-yl)-6-[2-(3-pyridinyl)-5-thiazolyl]-pyridine; M.UN.12.b) 2-[6-[2-(5-Fluoro-3-pyridinyl)-5-thiazolyl]-2-pyridinyl]-pyrimidine; M.UN.12.c) 2-[6-[2-(3-Pyridinyl)-5-thiazolyl]-2-pyridinyl]-pyrimidine; M.UN.12.d) N-Methylsulfonyl-6-[2-(3-pyridyl)thiazol-5-yl]pyridine-2-carboxamide; M.UN.12.e) N-Methylsulfonyl-6-[2-(3-pyridyl)thiazol-5-yl]pyridine-2-carboxamide; M.UN.12.f) N-Ethyl-N-[4-methyl-2-(3-pyridyl)thiazol-5-yl]-3-methylthio-propanamide; M.UN.12.g) N-Methyl-N-[4-methyl-2-(3-pyridyl)thiazol-5-yl]-3-methylthio-propanamide; M.UN.12.h) N,2-Di-methyl-N-[4-methyl-2-(3-pyridyl)thiazol-5-yl]-3-methylthio-propanamide; M.UN.12.i) N-Ethyl-2-methyl-N-[4-methyl-2-(3-pyridyl)thiazol-5-yl]-3-methylthio-propanamide; M.UN.12.j) N-[4-Chloro-2-(3-pyridyl)thiazol-5-yl]-N-ethyl-2-methyl-3-methylthio-propanamide; M.UN.12.k) N-[4-Chloro-2-(3-pyridyl)thiazol-5-yl]-N,2-dimethyl-3-methylthio-propanamide; M.UN.12.l) N-[4-Chloro-2-(3-pyridyl)thiazol-5-yl]-N-methyl-3-methylthio-propanamide; M.UN.12.m) N-[4-Chloro-2-(3-pyridyl)thiazol-5-yl]-N-ethyl-3-methylthio-propanamide;

M.UN.14a) 1-[(6-Chloro-3-pyridinyl)methyl]-1,2,3,5,6,7-hexahydro-5-methoxy-7-methyl-8-nitro-imidazo[1,2-a]pyridine; or M.UN.14b) 1-[(6-Chloropyridin-3-yl)methyl]-7-methyl-8-nitro-1,2,3,5,6,7-hexahydroimidazo[1,2-a]pyridin-5-ol;

M.UN.16a) 1-isopropyl-N,5-dimethyl-N-pyridazin-4-yl-pyrazole-4-carboxamide; or M.UN.16b) 1-(1,2-dimethylpropyl)-N-ethyl-5-methyl-N-pyridazin-4-yl-pyrazole-4-carboxamide; M.UN.16c) N,5-dimethyl-N-pyridazin-4-yl-1-(2,2,2-trifluoro-1-methyl-ethyl)pyrazole-4-carboxamide; M.UN.16d) 1-[1-(1-cyanocyclopropyl)ethyl]-N-ethyl-5-methyl-N-pyridazin-4-yl-pyrazole-4-carboxamide; M.UN.16e) N-ethyl-1-(2-fluoro-1-methyl-propyl)-5-methyl-N-pyridazin-4-yl-pyrazole-4-carboxamide; M.UN.16f) 1-(1,2-dimethylpropyl)-N,5-dimethyl-N-pyridazin-4-yl-pyrazole-4-carboxamide; M.UN.16g) 1-[1-(1-cyanocyclopropyl)ethyl]-N,5-dimethyl-N-pyridazin-4-yl-pyrazole-4-carboxamide; M.UN.16h) N-methyl-1-(2-fluoro-1-methyl-propyl)-5-methyl-N-pyridazin-4-yl-pyrazole-4-carboxamide; M.UN.16i) 1-(4,4-difluorocyclohexyl)-N-ethyl-5-methyl-N-pyridazin-4-yl-pyrazole-4-carboxamide; or M.UN.16j) 1-(4,4-difluorocyclohexyl)-N,5-dimethyl-N-pyridazin-4-yl-pyrazole-4-carboxamide, M.UN.17a) N-(1-methylethyl)-2-(3-pyridinyl)-2H-indazole-4-carboxamide; M.UN.17b) N-cyclo-propyl-2-(3-pyridinyl)-2H-indazole-4-carboxamide; M.UN.17c) N-cyclohexyl-2-(3-pyridinyl)-2H-indazole-4-carboxamide; M.UN.17d) 2-(3-pyridinyl)-N-(2,2,2-trifluoroethyl)-2H-indazole-4-carboxamide; M.UN.17e) 2-(3-pyridinyl)-N-[(tetrahydro-2-furanyl)methyl]-2H-indazole-5-carboxamide; M.UN.17f) methyl 2-[[2-(3-pyridinyl)-2H-indazol-5-yl]carbonyl]hydrazinecarboxylate; M.UN.17g) N-[(2,2-difluorocyclopropyl)methyl]-2-(3-pyridinyl)-2H-indazole-5-carboxamide; M.UN.17h) N-(2,2-difluoropropyl)-2-(3-pyridinyl)-2H-indazole-5-carboxamide; M.UN.17i) 2-(3-pyridinyl)-N-(2-pyrimidinylmethyl)-2H-indazole-5-carboxamide; M.UN.17j) N-[(5-methyl-2-pyrazinyl)methyl]-2-(3-pyridinyl)-2H-indazole-5-carboxamide, M.UN.18a) N-[3-chloro-1-(3-pyridyl)pyrazol-4-yl]-N-ethyl-3-(3,3,3-trifluoropropylsulfanyl)propanamide; M.UN.18b) N-[3-chloro-1-(3-pyridyl)pyrazol-4-yl]-N-ethyl-3-(3,3,3-trifluoropropylsulfinyl)propanamide; M.UN.18c) N-[3-chloro-1-(3-pyridyl)pyrazol-4-yl]-3-[(2,2-difluorocyclopropyl)methylsulfanyl]-N-ethyl-propanamide; M.UN.18d) N-[3-chloro-1-(3-pyridyl)pyrazol-4-yl]-3-[(2,2-difluorocyclopropyl)methylsulfinyl]-N-ethyl-propanamide;

M.UN.19 sarolaner, M.UN.20 lotilaner;

M.UN.21 N-[4-Chloro-3-[[(phenylmethyl)amino]carbonyl]phenyl]-1-methyl-3-(1,1,2,2,2-pentafluoroethyl)-4-(trifluoromethyl)-1H-pyrazole-5-carboxamide; M.UN.22a 2-(3-ethylsulfonyl-2-pyridyl)-3-methyl-6-(trifluoromethyl)imidazo[4,5-b]pyridine, or M.UN.22b 2-[3-ethylsulfonyl-5-(trifluoromethyl)-2-pyridyl]-3-methyl-6-(trifluoromethyl)imidazo[4,5-b]pyridine;

M.UN.23a 4-[5-(3,5-dichlorophenyl)-5-(trifluoromethyl)-4H-isoxazol-3-yl]-N-[(4R)-2-ethyl-3-oxo-isoxazolidin-4-yl]-2-methyl-benzamide, or M.UN.23b 4-[5-(3,5-dichloro-4-fluoro-phenyl)-5-(tri-fluoromethyl)-4H-isoxazol-3-yl]-N-[(4R)-2-ethyl-3-oxo-isoxazolidin-4-yl]-2-methyl-benzamide;

M.UN.24a) N-[4-chloro-3-(cyclopropylcarbamoyl)phenyl]-2-methyl-5-(1,1,2,2,2-pentafluoro-ethyl)-4-(trifluoromethyl)pyrazole-3-carboxamide or M.UN.24b) N-[4-chloro-3-[(1-cyanocyclopropyl)carbamoyl]phenyl]-2-methyl-5-(1,1,2,2,2-pentafluoroethyl)-4-(trifluoromethyl)pyrazole-3-carboxamide; M.UN.25 acynonapyr; M.UN.26 benzpyrimoxan; M.UN.27 2-chloro-N-(1-cyanocyclopropyl)-5-[1-[2-methyl-5-(1,1,2,2,2-pentafluoroethyl)-4-(trifluoromethyl)pyrazol-3-yl]pyrazol-4-yl]benzamide; M.29.28 oxazosulfyl (2-(3-ethylsulfonyl-2-pyridyl)-5-(trifluoroethylsulfonyl)-1,3-benzoxazole);

A) Respiration inhibitors

Inhibitors of complex III at Qo site: azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17), 2 (2-(3-(2,6-dichlorophenyl)-1-methyl-allylideneaminooxymethyl)-phenyl)-2 methoxyimino-N methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5 phenyl-pyrazol-3-yl)oxylmethyl]phenyl]-N-methoxy-carbamate (A.1.22), 1-[3-chloro-2 [[1 (4-chlorophenyl)-1H-pyrazol-3-yl]oxymethyl]phenyl]-4-methyl-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methylphenyl]-4-methyl-tetrazol-5-one (A.1.25), 1-[2-[[1-(4-chlorophenyl)pyrazol-3-yl]oxymethyl]-3-fluorophenyl]-4-methyl-tetrazol-5-one (A.1.26), 1-[2-[[1-(2,4-dichlorophenyl)pyrazol-3-yl]oxymethyl]-3-fluorophenyl]-4-methyl-tetrazol-5-one (A.1.27), 1-[3-cyclopropyl-2-[[2-methyl-4 (1 methylpyrazol-3-yl)phenoxy]methyl]phenyl]-4 methyl-tetrazol-5-one (A.1.30), 1 [3 (difluoro-methoxy)-2-[[2-methyl-4-(1 methylpyrazol-3 yl)phenoxy]methyl]phenyl]-4 methyl-tetrazol-5-one (A.1.31), 1-methyl-4-[3- methyl-2 [[2 methyl-4-(1-methylpyrazol-3 yl)phenoxy] methyl]phenyl]tetrazol-5-one (A.1.32), (Z,2E)-5-[1-(2, 4-dichlorophenyl)pyrazol-3-yl]-oxy-2-methoxyimino-N,3-di-methyl-pent-3-enamide (A.1.34), (Z,2E) 5 [1 (4-chlorophenyl)pyrazol-3-yl]oxy-2-methoxyimino-N, 3-dimethyl-pent-3-enamide (A.1.35), pyriminostrobin (A.1.36), bifujunzhi (A.1.37), 2-(ortho-((2,5-dimethylphenyl-oxy-methylen)phenyl)-3-methoxy-acrylic acid methylester (A.1.38);

inhibitors of complex III at Qi site: cyazofamid (A.2.1), amisulbrom (A.2.2), [(6S,7R,8R) 8 benzyl-3-[(3-hydroxy-4-methoxy-pyridine-2-carbonyl)amino]-6-methyl-4,9-dioxo-1,5-dioxonan-7-yl] 2-methylpropanoate (A.2.3), fenpicoxamid (A.2.4);

inhibitors of complex II: benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.15), penthiopyrad (A.3.16), pydiflumetofen (A.3.17), pyraziflumid (A.3.18), sedaxane (A.3.19), tecloftalam (A.3.20), thifluzamide (A.3.21), 3 (difluoromethyl)-1-methyl-N-(1,1,3-trimethylindan-4-yl) pyrazole-4 carboxamide (A.3.22), 3 (trifluoromethyl)-1-methyl-N-(1,1,3-trimethylindan-4-yl)pyrazole-4 carboxamide (A.3.23), 1,3-dimethyl-N-(1,1,3-trimethylindan-4-yl)pyrazole-4-carboxamide (A.3.24), 3-(trifluoromethyl)-1,5 dimethyl-N-(1,1,3-trimethylindan-4-yl)pyrazole-4-carboxamide (A.3.25), 1,3,5-trimethyl-N-(1,1,3-trimethylindan-4-yl)pyrazole-4-carboxamide (A.3.26), 3-(difluoromethyl)-1,5 dimethyl-N-(1,1,3-trimethylindan-4-yl)pyrazole-4-carboxamide (A.3.27), 3-(difluoromethyl)-N (7 fluoro-1,1,3-trimethyl-indan-4-yl)-1-methyl-pyrazole-4-carboxamide (A.3.28), N-[(5-chloro-2-isopropyl-phenyl)methyl]-N-cyclopropyl-5-fluoro-1,3-dimethyl-pyrazole-4-carboxamide (A.3.29), methyl (E)-2-[2-[[5-cyano-2-methyl-phenoxy)methyl]phenyl]-3-methoxy-prop-2 enoate (A.3.30), N-[(5-chloro-2-isopropyl-phenyl)methyl]-N-cyclopropyl-3-(difluoromethyl)-5 fluoro-1-methyl-pyrazole-4-carboxamide (A.3.31), 2-(difluoromethyl)-N-(1,1,3-trimethyl-indan-4-yl)pyridine-3-carboxamide (A.3.32), 2-(difluoromethyl)-N-[(3R)-1,1,3-trimethylindan-4-yl]pyridine-3-carboxamide (A.3.33), 2-(difluoromethyl)-N-(3-ethyl-1,1-dimethyl-indan-4-yl) pyridine-3-carboxamide (A.3.34), 2-(difluoromethyl)-N-[(3R)-3-ethyl-1,1-dimethyl-indan-4-yl]pyridine-3-carboxamide (A.3.35), 2-(difluoromethyl)-N-(1,1-dimethyl-3-propyl-indan-4-yl)pyridine-3-carboxamide (A.3.36), 2-(difluoromethyl)-N-[(3R)-1,1-dimethyl-3-propyl-indan-4-yl]pyridine-3-carboxamide (A.3.37), 2-(difluoromethyl)-N-(3-isobutyl-1,1-dimethyl-indan-4-yl)pyridine-3-carboxamide (A.3.38), 2-(difluoromethyl)-N-[(3R)-3-isobutyl-1,1-dimethyl-indan 4 yl]pyridine-3-carboxamide (A.3.39);

other respiration inhibitors: diflumetorim (A.4.1); nitrophenyl derivates: binapacryl (A.4.2), dinobuton (A.4.3), dinocap (A.4.4), fluazinam (A.4.5), meptyldinocap (A.4.6), ferimzone (A.4.7); organometal compounds: fentin salts, e.g. fentin-acetate (A.4.8), fentin chloride (A.4.9) or fentin hydroxide (A.4.10); ametoctradin (A.4.11); silthiofam (A.4.12);

B) Sterol biosynthesis inhibitors (SBI fungicides)

C14 demethylase inhibitors: triazoles: azaconazole (B.1.1), bitertanol (B.1.2), bromu-conazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), ipfentrifluconazole, (B.1.37), mefentrifluconazole (B.1.38), 2-(chloromethyl)-2-methyl-5-(p-tolylmethyl)-1 (1,2,4-triazol-1-ylmethyl)cyclopentanol (B.1.43); imidazoles: imazalil (B.1.44), pefurazoate (B.1.45), prochloraz (B.1.46), triflumizol (B.1.47); pyrimidines, pyridines and piperazines: fenarimol (B.1.49), pyrifenox (B.1.50), triforine (B.1.51), [3-(4-chloro-2-fluoro-phenyl)-5-(2,4-difluorophenyl)isoxazol-4-yl]-(3-pyridyl) methanol (B.1.52);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

Other Sterol biosynthesis inhibitors: chlorphenomizole (B.4.1);

C) Nucleic acid synthesis inhibitors phenylamides or acyl amino acid fungicides: benalaxyl (C.1.1), benalaxyl-M (C.1.2), kiralaxyl (C.1.3), metalaxyl (C.1.4), metalaxyl-M (C.1.5), ofurace (C.1.6), oxadixyl (C.1.7);

other nucleic acid synthesis inhibitors: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4 amine (C.2.6), 5-fluoro-2-(4-fluorophenylmethoxy)pyrimidin-4 amine (C.2.7), 5-fluoro-2 (4 chlorophenylmethoxy)pyrimidin-4 amine (C.2.8);

D) Inhibitors of cell division and cytoskeleton tubulin inhibitors: benomyl (D.1.1), carbendazim (D.1.2), fuberidazole (D1.3), thiabendazole (D.1.4), thiophanate-methyl (D.1.5), 3-chloro-4-(2,6-difluorophenyl)-6-methyl-5-phenyl-pyridazine (D.1.6), 3-chloro-6-methyl-5-phenyl-4-(2,4,6-trifluorophenyl)pyridazine (D.1.7), N ethyl-2-[(3-ethynyl-8-methyl-6-quinolyl) oxy]butanamide (D.1.8), N-ethyl-2-[(3-ethynyl-8 methyl-6 quinolyl)oxy]-2-methylsulfanyl-acetamide (D.1.9), 2-[(3-ethynyl-8-methyl-6-quinol-yl)oxy]-N (2-fluoroethyl)butanamide (D.1.10), 2-[(3-ethynyl-8-methyl-6-quinolyl)oxy]-N-(2-flu-oroethyl)-2-methoxy-acetamide (D.1.11), 2-[(3-ethynyl-8-methyl-6-quinolyl)oxy]-N-propyl-butanamide (D.1.12), 2-[(3-ethynyl-8-methyl-6-quinolyl)oxy]-2-methoxy-N-propyl-acetamide (D.1.13), 2-[(3-ethynyl-8-methyl-6-quinolyl)oxy]-2-methylsulfanyl-N-propyl-acetamide (D.1.14), 2 [(3 ethynyl-8-methyl-6-quinolyl)oxy]-N-(2-fluoroethyl)-2-methylsulfanyl-acetamide (D.1.15), 4-(2-bromo-4-fluoro-phenyl)-N-(2-chloro-6-fluoro-phenyl)-2,5-dimethyl-pyrazol-3 amine (D.1.16);

other cell division inhibitors: diethofencarb (D.2.1), ethaboxam (D.2.2), pencycuron (D.2.3), fluopicolide (D.2.4), zoxamide (D.2.5), metrafenone (D.2.6), pyriofenone (D.2.7);

E) Inhibitors of amino acid and protein synthesis methionine synthesis inhibitors: cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6);

F) Signal transduction inhibitors

MAP/histidine kinase inhibitors: fluoroimid (F.1.1), iprodione (F.1.2), procymidone (F.1.3), vinclozolin (F.1.4), fludioxonil (F.1.5);

G protein inhibitors: quinoxyfen (F.2.1);

G) Lipid and membrane synthesis inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7);

compounds affecting cell membrane permeability and fatty acids: propamocarb (G.4.1);

inhibitors of oxysterol binding protein: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihydro-1,2 oxazol-5-yl]phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5 yl}-3-chlorophenyl methanesulfonate (G.5.3), 4-[1-[2-[3-(difluoromethyl)-5-methyl-pyrazol-1-yl]acetyl]-4-piperidyl]-N-tetralin-1-yl-pyridine-2-carboxamide (G.5.4), 4-[1-[2-[3,5-bis(difluoromethyl)pyrazol-1-yl]acetyl]-4-piperidyl]-N-tetralin-1-yl-pyri-dine-2-carboxamide (G.5.5), 4-[1-[2-[3-(difluoromethyl)-5-(trifluoromethyl)pyrazol-1-yl]acetyl]-4-piperidyl]-N-tetralin-1-yl-pyridine-2-carboxamide (G.5.6), 4-[1-[2-[5-cyclopropyl-3-(difluoromethyl)pyrazol-1-yl]acetyl]-4-piperidyl]-N-tetralin-1-yl-pyridine-2-carboxamide (G.5.7), 4-[1-[2-[5-methyl-3-(trifluoromethyl)pyrazol-1-yl]acetyl]-4-piperidyl]-N-tetralin-1-yl-pyridine-2-carboxamide (G.5.8), 4-[1-[2-[5-(difluoromethyl)-3-(trifluoromethyl)pyrazol-1-yl]acetyl]-4-piperidyl]-N-tetralin-1-yl-pyridine-2-carboxamide (G.5.9), 4 [1 [2-[3,5-bis(trifluoromethyl)pyrazol-1-yl]acetyl]-4-piperidyl]-N-tetralin-1-yl-pyridine-2-carboxamide (G.5.10), (4-[1-[2-[5-cyclopropyl-3-(trifluoromethyl)pyrazol-1-yl]acetyl]-4-piperidyl]-N-tetralin-1-yl-pyridine-2-carboxamide (G.5.11);

H) Inhibitors with Multi Site Action inorganic active substances: Bordeaux mixture (H.1.1), copper (H.1.2), copper acetate (H.1.3), copper hydroxide (H.1.4), copper oxychloride (H.1.5), basic copper sulfate (H.1.6), sulfur (H.1.7);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds: anilazine (H.3.1), chlorothalonil (H.3.2), captafol (H.3.3), captan (H.3.4), folpet (H.3.5), dichlofluanid (H.3.6), dichlorophen (H.3.7), hexachlorbenzene (H.3.8), pentachlorphenole (H.3.9) and its salts, phthalide (H.3.10), tolylfluanid (H.3.11);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell wall synthesis inhibitors inhibitors of glucan synthesis: validamycin (1.1.1), polyoxin B (1.1.2);

melanin synthesis inhibitors: pyroquilon (1.2.1), tricyclazole (1.2.2), carpropamid (1.2.3), dicyclomet (1.2.4), fenoxanil (1.2.5);

J) Plant defence inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), calcium phosphonate (J.1.11), potassium phosphonate (J.1.12), potassium or sodium bicarbonate (J.1.9), 4 cyclopropyl-N-(2,4-dimethoxyphenyl)thiadiazole-5-carboxamide (J.1.10);

K) Unknown mode of action bronopol (K.1.1), chinomethionat (K.1.2), cyflufenamid (K.1.3), cymoxanil (K.1.4), dazomet (K.1.5), debacarb (K.1.6), diclocymet (K.1.7), diclomezine (K.1.8), difenzoquat (K.1.9), difenzoquat-methylsulfate (K.1.10), diphenylamin (K.1.11), fenitropan (K.1.12), fenpyrazamine (K.1.13), flumetover (K.1.14), flusulfamide (K.1.15), flutianil (K.1.16), harpin (K.1.17), metha-sulfocarb (K.1.18), nitrapyrin (K.1.19), nitrothal-isopropyl (K.1.20), tolprocarb (K.1.21), oxincopper (K.1.22), proquinazid (K.1.23), tebufloquin (K.1.24), tecloftalam (K.1.25), triazoxide (K.1.26), N'-(4-(4-chloro-3-trifluoromethyl-phenoxy)-2,5-dimethyl-phenyl)-N-ethyl-N methyl formamidine (K.1.27), N' (4-(4-fluoro-3-trifluoromethyl-phenoxy)-2,5-dimethyl-phenyl)-N-ethyl-N-methyl formamidine (K.1.28), N'-[4-[[3-[(4-chlorophenyl)methyl]-1,2,4-thiadiazol-5-yl]oxy]-2,5-dimethyl-phenyl]-N-ethyl-N-methyl-formamidine (K.1.29), N'-(5-bromo-6-indan-2-yloxy-2-methyl-3-pyridyl)-N-ethyl-N-methyl-formamidine (K.1.30), N'-[5-bromo-6-[1-(3,5-difluorophenyl)ethoxy]-2-methyl-3-pyridyl]-N-ethyl-N-methyl-formamidine (K.1.31), N'-[5-bromo-6-(4-isopropylcyclohexoxy)-2-methyl-3-pyridyl]-N-ethyl-N-methyl-formamidine (K.1.32), N' [5 bromo-2-methyl-6-(1-phenyl-ethoxy)-3-pyridyl]-N-ethyl-N-methyl-formamidine (K.1.33), N'-(2-methyl-5-trifluoromethyl-4-(3-trimethylsilanyl-propoxy)-phenyl)-N-ethyl-N-methyl formamidine (K.1.34), N'-(5-difluoromethyl-2 methyl-4-(3-trimethylsilanyl-propoxy)-phenyl)-N-ethyl-N-methyl formamidine (K.1.35), 2-(4-chloro-phenyl)-N-[4-(3,4-dimethoxy-phenyl)-isoxazol-5 yl]-2-prop-2-ynyloxy-acetamide (K.1.36), 3 [5-(4-chloro-phenyl)-2,3-dimethyl-isoxazolidin-3-yl]-pyridine (pyrisoxazole) (K.1.37), 3-[5-(4-methyl-phenyl)-2,3-dimethyl-isoxazolidin-3 yl]-pyridine (K.1.38), 5-chloro-1 (4,6-dimethoxy-pyrimidin-2-yl)-2-methyl-1H-benzoimidazole (K.1.39), ethyl (Z) 3 amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), but-3-ynyl N-[6-[[(Z)-[(1-methyltetrazol-5-yl)-phenyl-methylene]amino]oxymethyl]-2-pyridyl]carbamate (K.1.43), 2-[2-[(7,8-difluoro-2-methyl-3-quinolyl)oxy]-6-fluoro-phenyl]propan-2-ol (K.1.44), 2-[2-fluoro-6-[(8-fluoro-2-methyl-3-quinolyl)oxy]phen-yl]propan-2-ol (K.1.45), quinofumelin (K.1.47), 9-fluoro-2,2-dimethyl-5-(3-quinolyl)-3H 1,4 benzoxazepine (K.1.49), 2-(6-benzyl-2-pyridyl)quinazoline (K.1.50), 2-[6-(3-fluoro-4 methoxy-phenyl)-5-methyl-2-pyridyl]quinazoline (K.1.51), dichlobentiazox (K.1.52), N'-(2,5-dimethyl-4-phenoxy-phenyl)-N-ethyl-N-methyl-formamidine (K.1.53);

dipymetitrone, isoflucypram; fluindapyr, inpyrfluxam, pyrifenamine.

The commercially available compounds of the group M listed above may be found in The Pesticide Manual, 17th Edition, C. MacBean, British Crop Protection Council (2015) among other publications. The online Pesticide Manual is updated regularly and is accessible through http://bcpcdata.com/pesticide-manual.html.

Another online data base for pesticides providing the ISO common names is http://www.alanwood.net/pesticides.

The M.4 cycloxaprid is known from WO2010/069266 and WO2011/069456. M.4A.1 is known from CN 103814937; CN105367557, CN 105481839. M.4A.2, guadipyr, is known from WO 2013/003977, and M.4A.3 (approved as paichongding in China) is known from WO 2007/101369. M.22B.1 is described in CN10171577 and M.22B.2 in CN102126994. Spiropidion M.23.1 is known from WO 2014/191271. M.28.1 and M.28.2 are known from WO2007/101540. M.28.3 is described in WO2005/077934. M.28.4 is described in WO2007/043677. M.28.5a) to M.28.5d) and M.28.5h) are described in WO 2007/006670, WO2013/024009 and WO 2013/024010, M.28.5i) is described in WO2011/085575, M.28.5j) in WO2008/134969, M.28.5k) in US2011/046186 and M.28.5l) in WO2012/034403. M.28.6 can be found in WO2012/034472. M.UN.3 is known from WO2006/089633 and M.UN.4 from WO2008/067911. M.UN.5 is described in WO2006/043635, and biological control agents on the basis of *Bacillus firmus* are described in WO2009/124707. Flupyrimin is described in WO2012/029672. M.UN.8 is known from WO2013/055584. M.UN.9.a) is described in WO2013/050317. M.UN.9.b) is described in WO2014/126208. M.UN.10 is known from WO2010/060379. Broflanilide and M.UN.11.b) to M.UN.11.h) are described in WO2010/018714, and M.UN.11i) to M.UN.11.p) in WO 2010/127926. M.UN.12.a) to M.UN.12.c) are known from WO2010/006713, M.UN.12.d) and M.UN.12.e) are known from WO2012/000896, and M.UN.12.f) to M.UN.12.m) from WO 2010/129497. M.UN.14a) and M.UN.14b) are known from WO2007/101369. M.UN.16.a) to M.UN.16h) are described in WO2010/034737, WO2012/084670, and WO2012/143317, resp., and M.UN.16i) and M.UN.16j) are described in WO2015/055497. M.UN.17a) to M.UN.17.j) are described in WO2015/038503. M.UN.18a) to M.UN.18d) are described in US2014/0213448. M.UN.19 is described in WO2014/036056. M.UN.20 is known from WO2014/090918. M.UN.21 is known from EP2910126. M.UN.22a and M.UN.22b are known from WO2015/059039 and WO2015/190316. M.UN.23a and M.UN.23b are known from WO2013/050302. M.UN.24a and M.UN.24b are known from WO2012/126766. Acynonapyr M.UN.25 is known from WO 2011/105506. Benzpyrimoxan M.UN.26 is known from WO2016/104516. M.UN.27 is known from WO2016174049. The compound M.29.28 is known from WO2017104592.

The fungicides described by IUPAC nomenclature, their preparation and their pesticidal activity is also known (cf. Can. J. Plant Sci. 48(6), 587-94, 1968; EP-A 141317; EP-A 152031; EP-A 226917; EP-A 243970; EP-A 256503; EP-A 428941; EP-A 532022; EP-A 1028125; EP-A 1035122; EP-A 1201648; EP-A 1122244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 10/139271, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833), CN 1907024, CN 1456054, CN 103387541, CN 1309897, WO 12/84812, CN 1907024, WO 09094442, WO 14/60177, WO 13/116251, WO 08/013622, WO 15/65922, WO 94/01546, EP 2865265, WO 07/129454, WO 12/165511, WO 11/081174, WO 13/47441).

In a further embodiment, the invention relates to mixtures comprising a compound of formula (I) as described above, in particular a compound I-1 or I-R-1, and at least one compound II which is metaaldehyde, in particular granular metaaldehyde.

In a further embodiment, the invention relates to mixtures comprising a compound of formula (I) as described above, in particular a compound I-1 or I-R-1, and at least one compound II selected from the group of methiadinil, anthraquinones, beta-aminobutyric acid, laminarin, chitosan, thiamine and riboflavin.

In a further embodiment, the invention relates to methods according to the invention, applying mixtures comprising a compound of formula (I) as described above, in particular a compound I-1 or I-R-1, and at least one compound II selected from the group of oxyenadenine (also called zeatin), kinetin (oxy)enadenine, brassinolides, insecticidal extracts of *Celastrus angulatus*, matrine, cnidiadin, tetramycin.

In a further embodiment, the invention relates to mixtures comprising a non-racemic compound of formula (I) as described above, in particular a compound I-1 with enantiomeric excess of compound I-R-1, and at least one compound II which is metaaldehyde, in particular granular metaaldehyde.

In a further embodiment, the invention relates to mixtures comprising a non-racemic compound of formula (I) as described above, in particular a compound I-1 with enantiomeric excess of compound I-R-1, and at least one compound II selected from the group of methiadinil, anthraquinones, beta-aminobutyric acid, laminarin, chitosan, thiamine and riboflavin.

In a further embodiment, the invention relates to methods according to the invention, applying mixtures comprising a non-racemic compound of formula (I) as described above, in particular a compound I-1 with enantiomeric excess of compound I-R-1, and at least one compound II selected from the group of oxyenadenine (also called zeatin), kinetin (oxy)enadenine, brassinolides, insecticidal extracts of *Celastrus angulatus*, matrine, cnidiadin, tetramycin.

The present invention relates to a mixture of at least one compound I or non-racemic compound of formula (I) or compound of formula (I) with enantiomeric excess of compound of formula (I-R) or (I-S), of the present invention as component I with at least one mixing partner II as defined above. In one embodiment, the invention relates to binary mixtures of one components I with one mixing partner II as defined above as component II.

Preferred weight ratios for such binary mixtures are from 10000:1 to 1:10000, preferably from 7000:1 to 1:7000, also preferably from 5000:1 to 1:5000, also preferably from 1000:1 to 1:1000, more preferably from 100:1 to 1:100, also more preferably from 70:1 to 1:70, particularly preferably from 25:1 to 1:25, also particularly preferably from 10:1 to 1:10. In such binary mixtures, components I and II may be used in equal amounts, or an excess of component I, or an excess of component II may be used.

In the mixtures of the present invention, the ingredients may be used sequentially or in combination with each other, if appropriate also added only immediately prior to use (tank mix). For example, the plant(s) may be sprayed with compound II either before or after being treated with component I.

In one embodiment of the invention, the mixtures of the present invention are mixtures of a compound of formula (I), preferably (I-R), preferably compounds I-1, I-R-1, I-2, or I-R-2, with a compound selected from the group of benomyl, carbendazim, epoxiconazole, fluquinconazole, flutriafol, flusilazole, metconazole, prochloraz, prothioconazole, tebuconazole, triticonazole, pyraclostrobin, trifloxystrobin, boscalid, dimethomorph, penthiopyrad, dodemorph, famoxadone, fenpropimorph, proquinazid, pyrimethanil, tridemorph, maneb, mancozeb, metiram, thiram, chlorothalonil, dithianon, flusulfamide, metrafenone, fluxapyroxad, bixafen, penflufen, sedaxane, isopyrazam, oxazosulfyl. Especially preferred is pyraclostrobin, oxazosulfyl, and fluxapyroxad.

In one embodiment of the invention, the mixtures of the present invention are mixtures of a compound of formula (I), preferably (I-R), preferably compounds I-1, I-R-1, I-2 or I-R-2, with a compound selected from the group of imidacloprid, clothianidin, dinotefuran, chlorantraniliprole, cyantraniliprole, spinetoram, spinosad, ethiprole, fipronil, triflumezopyrim, flonicamid, oxazosulfyl, and tetraniliprole.

In one embodiment of the invention, the mixtures of the present invention are mixtures of a compound of formula (I), preferably (I-R), preferably compounds I-1, I-R-1, I-2 or I-R-2, with a compound selected from the group of probenazole, isotianil, tricyclazole, pyroquilon, isoprothiolane, tolprocarb, carpropamid, diclocymet, azoxystrobin, oxazosulfyl, and orysastrobin.

In one embodiment of the invention, the mixtures of the present invention are mixtures of a compound of formula (I), preferably (I-R), preferably compounds I-1, I-R-1, I-2 or I-R-2, with a compound selected from the group of furametpyr, thifluzamide, simeconazole, penflufen, azoxystrobin, orysastrobin.

In one embodiment of the invention, the mixtures of the present invention are mixtures of a compound of formula (I), preferably (I-R), preferably compounds I-1, I-R-1, I-2 or I-R-2, with Oxazosulfyl.

In one embodiment of the invention, the mixtures of the present invention are mixtures of a non-racemic compound of formula (I), preferably compound of formula (I) with enantiomeric excess of compound (I-R), preferably compounds I-1 with enantiomeric excess of compound I-R-1, or a compound of formula (I-R), preferably the compound I-R-1, with a compound selected from the group of M.2: GABA-gated chloride channel antagonists, M.3: Sodium channel modulators, M.4: Nicotinic acetylcholine receptor agonists, M.5: Nicotinic acetylcholine receptor allosteric activators, M.6: Chloride channel activators from the class of avermectins and milbemycins, M.9: Chordotonal organ TRPV channel modulators, M.13: Uncouplers of oxidative phosphorylation via disruption of the proton gradient, M.15: Inhibitors of the chitin biosynthesis type 0, M.16: Inhibitors of the chitin biosynthesis type, M.22: Voltage-dependent sodium channel blockers, M.23: Inhibitors of the of acetyl CoA carboxylase, M.28: Ryanodine receptor-modulators from the class of diamides, M.29:Chordotonal organ Modulators, M.UN.9.b, M.29.28, Respiration inhibitors: Inhibitors of complex Ill at Qo site, inhibitors of complex Ill at Qi site, inhibitors of complex II, Sterol biosynthesis inhibitors, Lipid and membrane synthesis inhibitors, Cell wall synthesis inhibitors preferably melanin synthesis inhibitors, Plant defence inducers, diclocymet (K.1.7), tolprocarb (K.1.21), and picarbutrazox (K.1.41).

In one embodiment of the invention, the mixtures of the present invention are mixtures of a non-racemic compound of formula (I), preferably compound of formula (I) with enantiomeric excess of compound (I-R), preferably compounds I-1 with enantiomeric excess of compound I-R-1, or a compound of formula (I-R), preferably the compound I-R-1, with a compound selected from the group of fipronil, alpha-cypermethrin, chlorfenapyr, metaflumizone, abamectin, pymetrozine, thiamethoxam, imidacloprid, dinotefuran, dinotefuran, clothianidin, flonicamid, spirotetramat, buprofezine, chlorantraniliprole, cyantraniliprole, tetraniliprole, sulfoxaflor, indoxacarb, triflumezopyrim, ethiprole, spinetoram, spinosad, spiropidion, fluxametamide, penflufen, tricyclazole, azoxystrobin, isoprothiolane, tolprocarb, carpropamid, diclocymet, furametpyr, simeconazole, probenazole, orysastrobin, pyroquilon, thifluzamide, picarbutrazox, oxazosulfyl, methoxyfenozid, flubendiamid, flufenoxuron, cyazofamid, metalaxyl, amisulbrom, cyclaniliprole, diclomet, and isotianil. Especially preferred is alpha-cypermethrin, flonicamid, fluxametamide, spinetoram, indoxacarb, oxazosulfyl, pymetrozine, triflumezopyrim, flufenoxuron, furametpyr, metalaxyl, probenazole, diclomet, penflufen, pyroquilon, simeconazol, buprofezin, tricyclazole, or spinosad In one embodiment of the invention, the mixtures of the present invention are mixtures of a non-racemic compound of formula (I), preferably compound of formula (I) with enantiomeric excess of compound (I-R), preferably compounds I-1 with enantiomeric excess of compound I-R-1, or a compound of formula (I-R), preferably the compound I-R-1, with a compound selected from the group of fipronil, alpha-cypermethrin, chlorfenapyr, metaflumizone, abamectin, pymetrozine, thiamethoxam, imidacloprid, dinotefuran, dinotefuran, clothianidin, flonicamid, spirotetramat, buprofezine, chlorantraniliprole, cyantraniliprole, tetraniliprole, sulfoxaflor, indoxacarb, triflumezopyrim, ethiprole, spinetoram, spinosad, spiropidion, fluxametamide, oxazosulfyl, methoxyfenozid, flubendiamid, flufenoxuron, and cyclaniliprole.

In one embodiment of the invention, the mixtures of the present invention are mixtures of a non-racemic compound of formula (I), preferably compound of formula (I) with enantiomeric excess of compound (I-R), preferably compounds I-1 with enantiomeric excess of compound I-R-1, or a compound of formula (I-R), preferably the compound I-R-1, with a compound selected from the group of probenazole, tricyclazole, pyroquilon, isoprothiolane, tolprocarb, carpropamid, diclocymet, azoxystrobin, orysastrobin, furametpyr, thifluzamide, simeconazole, penflufen, picarbutrazox, cyazofamid, metalaxyl, amisulbrom, and isotianil.

In one embodiment of the invention, the mixtures of the present invention are mixtures of a non-racemic compound of formula (I), preferably compound of formula (I) with enantiomeric excess of compound (I-R), preferably compounds I-1 with enantiomeric excess of compound I-R-1, with a compound selected from the group of fipronil, alpha-cypermethrin, chlorfenapyr, metaflumizone, abamectin, pymetrozine, thiamethoxam, imidacloprid, dinotefuran, dinotefuran, clothianidin, flonicamid, spirotetramat, buprofezine, chlorantraniliprole, cyantraniliprole, tetraniliprole, sulfoxaflor, indoxacarb, triflumezopyrim, ethiprole, spinetoram, spinosad, spiropidion, fluxametamide, penflufen, tricyclazole, azoxystrobin, isoprothiolane, tolprocarb, carpropamid, diclocymet, furametpyr, simeconazole, probenazole, orysastrobin, pyroquilon, thifluzamide, picarbutrazox, oxazosulfyl, methoxyfenozid, flubendiamid, flufenoxuron, cyazofamid, metalaxyl, amisulbrom, cyclaniliprole, dicyclomet, and isotianil. Especially preferred is alpha-cypermethrin, flonicamid, fluxametamide, spinetoram, indoxacarb, oxazosulfyl, pymetrozine, triflumezopyrim, flufenoxuron, furametpyr, metalaxyl, probenazole, dicyclomet, penflufen, pyroquilon, simeconazol, buprofezin, tricyclazole, or spinosad.

In one embodiment of the invention, the mixtures of the present invention are mixtures of a non-racemic compound of formula (I), preferably compound of formula (I) with enantiomeric excess of compound (I-R), preferably compounds I-1 with enantiomeric excess of compound I-R-1, with a compound selected from the group of fipronil, alpha-cypermethrin, chlorfenapyr, metaflumizone, abamectin, pymetrozine, thiamethoxam, imidacloprid, dinotefuran, dinotefuran, clothianidin, flonicamid, spirotetramat, buprofezine, chlorantraniliprole, cyantraniliprole, tetraniliprole, sulfoxaflor, indoxacarb, triflumezopyrim, ethiprole, spinetoram, spinosad, spiropidion, fluxametamide, oxazosulfyl, methoxyfenozid, flubendiamid, flufenoxuron, and cyclaniliprole.

In one embodiment of the invention, the mixtures of the present invention are mixtures of a non-racemic compound of formula (I), preferably compound of formula (I) with enantiomeric excess of compound (I-R), preferably compounds I-1 with enantiomeric excess of compound I-R-1, with a compound selected from the group of probenazole, tricyclazole, pyroquilon, isoprothiolane, tolprocarb, carpropamid, diclocymet, azoxystrobin, orysastrobin, furametpyr, thifluzamide, simeconazole, penflufen, picarbutrazox, cyazofamid, metalaxyl, amisulbrom, and isotianil.

In one embodiment of the invention, the mixtures of the present invention are mixtures of a non-racemic compound of formula (I), preferably compound of formula (I-R), preferably the compound I-R-1, with a compound selected from the group of fipronil, alpha-cypermethrin, chlorfenapyr, metaflumizone, abamectin, pymetrozine, thiamethoxam, imidacloprid, dinotefuran, dinotefuran, clothianidin, flonicamid, spirotetramat, buprofezine, chlorantraniliprole, cyantraniliprole, tetraniliprole, sulfoxaflor, indoxacarb, triflumezopyrim, ethiprole, spinetoram, spinosad, spiropidion, fluxametamide, penflufen, tricyclazole, azoxystrobin, isoprothiolane, tolprocarb, carpropamid, diclocymet, furametpyr, simeconazole, probenazole, orysastrobin, pyroquilon, thifluzamide, picarbutrazox, oxazosulfyl, methoxyfenozid, flubendiamid, flufenoxuron, cyazofamid, metalaxyl, amisulbrom, cyclaniliprole, dicyclomet, and isotianil. Especially preferred is alpha-cypermethrin, flonicamid, fluxametamide, spinetoram, indoxacarb, oxazosulfyl, pymetrozine, triflumezopyrim, flufenoxuron, furametpyr, metalaxyl, probenazole, dicyclomet, penflufen, pyroquilon, simeconazol, buprofezin, tricyclazole, or spinosad.

In one embodiment of the invention, the mixtures of the present invention are mixtures of a non-racemic compound of formula (I), preferably compound of formula (I-R), preferably the compound I-R-1, with a compound selected from the group of fipronil, alpha-cypermethrin, chlorfenapyr, metaflumizone, abamectin, pymetrozine, thiamethoxam, imidacloprid, dinotefuran, dinotefuran, clothianidin, flonicamid, spirotetramat, buprofezine, chlorantraniliprole, cyantraniliprole, tetraniliprole, sulfoxaflor, indoxacarb, triflumezopyrim, ethiprole, spinetoram, spinosad, spiropidion, fluxametamide, oxazosulfyl, methoxyfenozid, flubendiamid, flufenoxuron, and cyclaniliprole.

In one embodiment of the invention, the mixtures of the present invention are mixtures of a non-racemic compound of formula (I), preferably compound of formula (I-R), preferably the compound I-R-1, with a compound selected from the group of probenazole, tricyclazole, pyroquilon, isoprothiolane, tolprocarb, carpropamid, diclocymet, azoxystrobin, orysastrobin, furametpyr, thifluzamide, simeconazole, penflufen, picarbutrazox, cyazofamid, metalaxyl, amisulbrom, and isotianil.

In one embodiment of the invention, the mixtures of the present invention are mixtures of a non-racemic compound of formula (I), preferably compound of formula (I), preferably compounds I-1 with enantiomeric excess of compound I-R-1, with a compound selected from the group of alpha-cypermethrin, flonicamid, fluxametamide, spinetoram, indoxacarb, oxazosulfyl, pymetrozine, triflumezopyrim, flufenoxuron, furametpyr, metalaxyl, probenazole, dicyclomet, penflufen, pyroquilon, simeconazol, buprofezin, tricyclazole, or spinosad.

In one embodiment of the invention, the mixtures of the present invention are mixtures of a non-racemic compound of formula (I), preferably compound of formula (I-R), preferably the compound I-R-1, with a compound selected from the group of alpha-cypermethrin, flonicamid, fluxametamide, spinetoram, indoxacarb, oxazosulfyl, pymetrozine, triflumezopyrim, flufenoxuron, furametpyr, metalaxyl, probenazole, dicyclomet, penflufen, pyroquilon, simeconazol, buprofezin, tricyclazole, or spinosad.

In one embodiment of the invention, the mixtures of the present invention are mixtures of a non-racemic compound of formula (I), preferably compound of formula (I), preferably compounds I-1 with enantiomeric excess of compound I-R-1, or I-2 with enantiomeric excess of compound I-R-2, with Oxazosulfyl.

Especially preferred mixtures according to the invention are listed in the following table M, wherein the compounds I are as defined in the description:

TABLE M

| Mixture | Comp. I | Compound II |
|---------|---------|-------------|
| M-1 | I-1 | fipronil |
| M-2 | I-1 | alpha-cypermethrin |
| M-3 | I-1 | chlorfenapyr |
| M-4 | I-1 | metaflumizone |
| M-5 | I-1 | abamectin |
| M-6 | I-1 | pymetrozine |
| M-7 | I-1 | thiamethoxam |
| M-8 | I-1 | imidacloprid |
| M-9 | I-1 | dinotefuran |
| M-10 | I-1 | clothianidin |
| M-11 | I-1 | bifenthrin |
| M-12 | I-1 | acetamiprid |
| M-13 | I-1 | nitenpyram |
| M-14 | I-1 | cypermethrin |
| M-15 | I-1 | cyhalothrin |
| M-16 | I-1 | lambda-cyhalothrin |
| M-17 | I-1 | flonicamid |
| M-18 | I-1 | spirotetramat |
| M-19 | I-1 | buprofezine |

TABLE M-continued

| Mixture | Comp. I | Compound II |
|---|---|---|
| M-20 | I-1 | chlorantraniliprole |
| M-21 | I-1 | cyantraniliprole |
| M-22 | I-1 | tetraniliprole |
| M-23 | I-1 | sulfoxaflor |
| M-24 | I-1 | indoxacarb |
| M-25 | I-1 | afidopyropen |
| M-26 | I-1 | broflanilide |
| M-27 | I-1 | pyriprole |
| M-28 | I-1 | triflumezopyrim |
| M-29 | I-1 | flupyradifurone |
| M-30 | I-1 | dicloromezotiaz |
| M-31 | I-1 | chlorpyrifos |
| M-32 | I-1 | dichlorvos |
| M-33 | I-1 | triazophos |
| M-34 | I-1 | cartap |
| M-35 | I-1 | acephate |
| M-36 | I-1 | carbofuran |
| M-37 | I-1 | carbosulfan |
| M-38 | I-1 | emamectin |
| M-39 | I-1 | ethiprole |
| M-40 | I-1 | etofenprox |
| M-41 | I-1 | spinetoram |
| M-42 | I-1 | spinosad |
| M-43 | I-1 | fluhexafon |
| M-44 | I-1 | tefluthrin |
| M-45 | I-1 | momfluorothrin |
| M-46 | I-1 | benzpyrimoxan |
| M-47 | I-1 | cyhalodiamide |
| M-48 | I-1 | spiropidion |
| M-49 | I-1 | flupyrimin |
| M-50 | I-1 | cyclaniliprole |
| M-51 | I-1 | fluxametamide |
| M-52 | I-1 | tioxazafen |
| M-53 | I-1 | fluazaindolizine |
| M-54 | I-1 | pyrifluquinazone |
| M-55 | I-1 | metaaldehyde (in particular granular) |
| M-56 | I-1 | benomyl |
| M-57 | I-1 | epoxiconazole |
| M-58 | I-1 | fluquinconazole |
| M-59 | I-1 | flutriafol |
| M-60 | I-1 | flusilazole |
| M-61 | I-1 | metconazole |
| M-62 | I-1 | prochloraz |
| M-63 | I-1 | prothioconazole |
| M-64 | I-1 | tebuconazole |
| M-65 | I-1 | triticonazole |
| M-66 | I-1 | pyraclostrobin |
| M-67 | I-1 | trifloxystrobin |
| M-68 | I-1 | boscalid |
| M-69 | I-1 | dimethomorph |
| M-70 | I-1 | penthiopyrad |
| M-71 | I-1 | dodemorph |
| M-72 | I-1 | famoxadone |
| M-73 | I-1 | fenpropimorph |
| M-74 | I-1 | proquinazid |
| M-75 | I-1 | pyrimethanil |
| M-76 | I-1 | tridemorph |
| M-77 | I-1 | maneb |
| M-78 | I-1 | metiram |
| M-79 | I-1 | thiram |
| M-80 | I-1 | chlorothalonil |
| M-81 | I-1 | dithianon |
| M-82 | I-1 | flusulfamide |
| M-83 | I-1 | metrafenone |
| M-84 | I-1 | fluxapyroxad |
| M-85 | I-1 | bixafen |
| M-86 | I-1 | penflufen |
| M-87 | I-1 | sedaxane |
| M-88 | I-1 | isopyrazam |
| M-89 | I-1 | tricyclazole |
| M-90 | I-1 | azoxystrobin |
| M-91 | I-1 | difenoconazole |
| M-92 | I-1 | kasugamycin |
| M-93 | I-1 | isoprothiolane |
| M-94 | I-1 | tolprocarb |
| M-95 | I-1 | carpropamid |
| M-96 | I-1 | diclocymet |
| M-97 | I-1 | furametpyr |
| M-98 | I-1 | simeconazole |
| M-99 | I-1 | probenazole |
| M-100 | I-1 | mancozeb |
| M-101 | I-1 | propiconazole |
| M-102 | I-1 | hexaconazole |
| M-103 | I-1 | tebuconazole |
| M-104 | I-1 | carbendazim |
| M-105 | I-1 | flutolanil |
| M-106 | I-1 | hymexazol |
| M-107 | I-1 | isotianil |
| M-108 | I-1 | orysastrobin |
| M-109 | I-1 | pencycuron |
| M-110 | I-1 | phthalide |
| M-111 | I-1 | pyroquilon |
| M-112 | I-1 | thifluzamide |
| M-113 | I-1 | thiophanate |
| M-114 | I-1 | thiophanate-methyl |
| M-115 | I-1 | tiadinil |
| M-116 | I-1 | validamycin |
| M-117 | I-1 | tebufloquin |
| M-118 | I-1 | benzovindiflupyr |
| M-119 | I-1 | picarbutrazox |
| M-120 | I-1 | pyraziflumid |
| M-121 | I-1 | dipymetitrone |
| M-122 | I-1 | pydiflumetofen |
| M-123 | I-1 | quinofumelin |
| M-124 | I-1 | ipfentrifluconazole |
| M-125 | I-1 | dichlobentiazox |
| M-126 | I-1 | fenpicoxamid |
| M-127 | I-1 | isoflucypram |
| M-128 | I-1 | fluindapyr |
| M-129 | I-1 | inpyrfluxam |
| M-130 | I-1 | pyrifenamine |
| M-131 | I-1 | mefentrifluconazole |
| M-132 | I-1 | oxazosulfyl |
| M-133 | I-1 | Methoxyfenozid |
| M-134 | I-1 | Flubendiamid |
| M-135 | I-1 | Flufenoxuron |
| M-136 | I-1 | cyazofamid |
| M-137 | I-1 | metalaxyl |
| M-138 | I-1 | Amisulbrom |
| M-139 | I-R-1 | fipronil |
| M-140 | I-R-1 | alpha-cypermethrin |
| M-141 | I-R-1 | chlorfenapyr |
| M-142 | I-R-1 | metaflumizone |
| M-143 | I-R-1 | abamectin |
| M-144 | I-R-1 | pymetrozine |
| M-145 | I-R-1 | thiamethoxam |
| M-146 | I-R-1 | imidacloprid |
| M-147 | I-R-1 | dinotefuran |
| M-148 | I-R-1 | clothianidin |
| M-149 | I-R-1 | bifenthrin |
| M-150 | I-R-1 | acetamiprid |
| M-151 | I-R-1 | nitenpyram |
| M-152 | I-R-1 | cypermethrin |
| M-153 | I-R-1 | cyhalothrin |
| M-154 | I-R-1 | lambda-cyhalothrin |
| M-155 | I-R-1 | flonicamid |
| M-156 | I-R-1 | spirotetramat |
| M-157 | I-R-1 | buprofezine |
| M-158 | I-R-1 | chlorantraniliprole |
| M-159 | I-R-1 | cyantraniliprole |
| M-160 | I-R-1 | tetraniliprole |
| M-161 | I-R-1 | sulfoxaflor |
| M-162 | I-R-1 | indoxacarb |
| M-163 | I-R-1 | afidopyropen |
| M-164 | I-R-1 | broflanilide |
| M-165 | I-R-1 | pyriprole |
| M-166 | I-R-1 | triflumezopyrim |
| M-167 | I-R-1 | flupyradifurone |
| M-168 | I-R-1 | dicloromezotiaz |
| M-169 | I-R-1 | chlorpyrifos |
| M-170 | I-R-1 | dichlorvos |
| M-171 | I-R-1 | triazophos |
| M-172 | I-R-1 | cartap |
| M-173 | I-R-1 | acephate |
| M-174 | I-R-1 | carbofuran |

TABLE M-continued

| Mixture | Comp. I | Compound II |
|---|---|---|
| M-175 | I-R-1 | carbosulfan |
| M-176 | I-R-1 | emamectin |
| M-177 | I-R-1 | ethiprole |
| M-178 | I-R-1 | etofenprox |
| M-179 | I-R-1 | spinetoram |
| M-180 | I-R-1 | spinosad |
| M-181 | I-R-1 | fluhexafon |
| M-182 | I-R-1 | tefluthrin |
| M-183 | I-R-1 | momfluorothrin |
| M-184 | I-R-1 | benzpyrimoxan |
| M-185 | I-R-1 | cyhalodiamide |
| M-186 | I-R-1 | spiropidion |
| M-187 | I-R-1 | flupyrimin |
| M-188 | I-R-1 | cyclaniliprole |
| M-189 | I-R-1 | fluxametamide |
| M-190 | I-R-1 | tioxazafen |
| M-191 | I-R-1 | fluazaindolizine |
| M-192 | I-R-1 | pyrifluquinazone |
| M-193 | I-R-1 | metaaldehyde (in particular granular) |
| M-194 | I-R-1 | benomyl |
| M-195 | I-R-1 | epoxiconazole |
| M-196 | I-R-1 | fluquinconazole |
| M-197 | I-R-1 | flutriafol |
| M-198 | I-R-1 | flusilazole |
| M-199 | I-R-1 | metconazole |
| M-200 | I-R-1 | prochloraz |
| M-201 | I-R-1 | prothioconazole |
| M-202 | I-R-1 | tebuconazole |
| M-203 | I-R-1 | triticonazole |
| M-204 | I-R-1 | pyraclostrobin |
| M-205 | I-R-1 | trifloxystrobin |
| M-206 | I-R-1 | boscalid |
| M-207 | I-R-1 | dimethomorph |
| M-208 | I-R-1 | penthiopyrad |
| M-209 | I-R-1 | dodemorph |
| M-210 | I-R-1 | famoxadone |
| M-211 | I-R-1 | fenpropimorph |
| M-212 | I-R-1 | proquinazid |
| M-213 | I-R-1 | pyrimethanil |
| M-214 | I-R-1 | tridemorph |
| M-215 | I-R-1 | maneb |
| M-216 | I-R-1 | metiram |
| M-217 | I-R-1 | thiram |
| M-218 | I-R-1 | chlorothalonil |
| M-219 | I-R-1 | dithianon |
| M-220 | I-R-1 | flusulfamide |
| M-221 | I-R-1 | metrafenone |
| M-222 | I-R-1 | fluxapyroxad |
| M-223 | I-R-1 | bixafen |
| M-224 | I-R-1 | penflufen |
| M-225 | I-R-1 | sedaxane |
| M-226 | I-R-1 | isopyrazam |
| M-227 | I-R-1 | tricyclazole |
| M-228 | I-R-1 | azoxystrobin |
| M-229 | I-R-1 | difenoconazole |
| M-230 | I-R-1 | kasugamycin |
| M-231 | I-R-1 | isoprothiolane |
| M-232 | I-R-1 | tolprocarb |
| M-233 | I-R-1 | carpropamid |
| M-234 | I-R-1 | diclocymet |
| M-235 | I-R-1 | furametpyr |
| M-236 | I-R-1 | simeconazole |
| M-237 | I-R-1 | probenazole |
| M-238 | I-R-1 | mancozeb |
| M-239 | I-R-1 | propiconazole |
| M-240 | I-R-1 | hexaconazole |
| M-241 | I-R-1 | tebuconazole |
| M-242 | I-R-1 | carbendazim |
| M-243 | I-R-1 | flutolanil |
| M-244 | I-R-1 | hymexazol |
| M-245 | I-R-1 | isotianil |
| M-246 | I-R-1 | orysastrobin |
| M-247 | I-R-1 | pencycuron |
| M-248 | I-R-1 | phthalide |
| M-249 | I-R-1 | pyroquilon |
| M-250 | I-R-1 | thifluzamide |
| M-251 | I-R-1 | thiophanate |
| M-252 | I-R-1 | thiophanate-methyl |
| M-253 | I-R-1 | tiadinil |
| M-254 | I-R-1 | validamycin |
| M-255 | I-R-1 | tebufloquin |
| M-256 | I-R-1 | benzovindiflupyr |
| M-257 | I-R-1 | picarbutrazox |
| M-258 | I-R-1 | pyraziflumid |
| M-259 | I-R-1 | dipymetitrone |
| M-260 | I-R-1 | pydiflumetofen |
| M-261 | I-R-1 | quinofumelin |
| M-262 | I-R-1 | ipfentrifluconazole |
| M-263 | I-R-1 | dichlobentiazox |
| M-264 | I-R-1 | fenpicoxamid |
| M-265 | I-R-1 | isoflucypram |
| M-266 | I-R-1 | fluindapyr |
| M-267 | I-R-1 | inpyrfluxam |
| M-268 | I-R-1 | pyrifenamine |
| M-269 | I-R-1 | mefentrifluconazole |
| M-270 | I-R-1 | oxazosulfyl |
| M-271 | I-R-1 | Methoxyfenozid |
| M-272 | I-R-1 | Flubendiamid |
| M-273 | I-R-1 | Flufenoxuron |
| M-274 | I-R-1 | cyazofamid |
| M-275 | I-R-1 | metalaxyl |
| M-276 | I-R-1 | Amisulbrom |

Analogously to mixtures M-1 to M-138, mixtures of non-racemic compound I-1 instead of the compound I-1 are part of the invention.

Analogously to mixtures M-1 to M-138, mixtures of I-2 instead of I-1 are part of the invention.

Analogously to mixtures M-139 to M-276, mixtures of I-R-2 instead of I-R-1 are part of the invention.

Analogously to mixtures M-1 to M-138, mixtures of I-3 instead of I-1 are part of the invention.

Analogously to mixtures M-139 to M-276, mixtures of I-R-3 instead of I-R-1 are part of the invention.

Analogously to mixtures M-1 to M-138, mixtures of I-4 instead of I-1 are part of the invention.

Analogously to mixtures M-139 to M-276, mixtures of I-R-4 instead of I-R-1 are part of the invention.

Analogously to mixtures M-1 to M-138, mixtures of I-5 instead of I-1 are part of the invention.

Analogously to mixtures M-139 to M-276, mixtures of I-R-5 instead of I-R-1 are part of the invention.

Analogously to mixtures M-1 to M-138, mixtures of I-6 instead of I-1 are part of the invention.

Analogously to mixtures M-139 to M-276, mixtures of I-R-6 instead of I-R-1 are part of the invention.

Analogously to mixtures M-1 to M-138, mixtures of I-1 with enantiomeric excess of compound I-R-1 instead of I-1 are part of the invention.

Additional Mixing Partners

The mixtures of the present invention may be combined and applied in agriculture in mixture with further active ingredients, for example with other pesticides, insecticides, nematicides, fungicides, herbicides, safeners, fertilizers such as ammonium nitrate, urea, potash, and superphosphate, phytotoxicants and plant growth regulators.

These mixtures are also embraced by the term "mixture(s) of the present invention" or "mixture(s) according to the invention".

These additional ingredients may be used sequentially or in combination with the mixtures of the invention, if appropriate also added only immediately prior to use (tank mix). For example, the plant(s) may be sprayed with a mixture of this invention either before or after being treated with other active ingredients.

Mixing partners can be selected from pesticides, in particular insecticides, nematicides, and acaricides, fungicides, herbicides, plant growth regulators, fertilizers, and the like. Preferred mixing partners are insecticides, nematicides and fungicides.

In one embodiment, the invention relates to ternary mixtures, comprising a compound I, a compound II and one further compound III, which is not identical to the compound I or II already present in the mixture.

In a sub-embodiment, the invention relates to a mixture of (1) a compound of formula (I), or a non-racemic compound of formula (I) or a compound of formula (I) with enantiomeric excess of (I-R) or compound (I-R), preferably non-racemic compound I-1 or the compound I-1 with enantiomeric excess of I-R-1 or the compound I-R-1 or I-2 or I-R-2, and (2) a compound selected from the group of imidacloprid, clothianidin, dinotefuran, chlorantraniliprole, cyantraniliprole, spinetoram, spinosad, ethiprole, fipronil, triflumezopyrim, flonicamid, oxazosulfyl and tetraniliprole, and (3) a compound selected from the group of probenazole, isotianil, tricyclazole, pyroquilon, isoprothiolane, tolprocarb, carpropamid, diclocymet, azoxystrobin, orysastrobin.

In one embodiment, the invention relates to 4-way mixtures, comprising a compound I, a compound II and two further compounds III, which are not identical to the compound I or II already present in the mixture.

In a sub-embodiment, the invention relates to a mixture of (1) a compound of formula (I), or a non-racemic compound of formula (I) or a compound of formula (I) with enantiomeric excess of (I-R) or compound (I-R), preferably non-racemic compound I-1 or the compound I-1 with enantiomeric excess of I-R-1 or the compound I-R-1 or I-2 or I-R-2, and (2) a compound selected from the group of imidacloprid, clothianidin, dinotefuran, chlorantraniliprole, cyantraniliprole, spinetoram, spinosad, ethiprole, fipronil, triflumezopyrim, flonicamid, Oxazosulfyl and tetraniliprole, and (3) a compound selected from the group of probenazole, isotianil, tricyclazole, pyroquilon, isoprothiolane, tolprocarb, carpropamid, diclocymet, azoxystrobin, orysastrobin, and (4) a compound selected from the group of furametpyr, thifluzamide, simeconazole, penflufen, azoxystrobin, orysastrobin, provided it is different from the compound under (3).

In one embodiment, the invention relates to 5-way mixtures, comprising a compound I, a compound II and three further compounds III, which are not identical to the compound I or II already present in the mixture.

Formulations

The invention also relates to agrochemical compositions comprising an auxiliary and at least one compound of the present invention or a mixture thereof.

An agrochemical composition comprises a pesticidally effective amount of a compound of the present invention or a mixture thereof. The term "pesticidally effective amount" is defined below.

The compounds of the present invention or the mixtures thereof can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Mono-graph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl-sulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetaines and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the present invention on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidones, polyvinylacetates, polyvinyl alcohols, polyacrylates, biological or synthetic waxes, and cellulose ethers.

Examples for Composition Types and their Preparation are:

i) Water-Soluble Concentrates (SL, LS)

10-60 wt % of a compound I or II or mixture according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible Concentrates (DC)

5-25 wt % of a compound I or II or mixture according to the invention and 1-10 wt % dispersant (e.g. polyvinylpyrrolidone) are dissolved in up to 100 wt % organic solvent (e.g. cyclohexanone). Dilution with water gives a dispersion.

iii) Emulsifiable Concentrates (EC)

15-70 wt % of a compound I or II or mixture according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)

5-40 wt % of a compound I or II or mixture according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound I or II or mixture according to the invention are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active sub-stance. For FS type composition up to 40 wt % binder (e.g. polyvinylalcohol) is added.

vi) Water-Dispersible Granules and Water-Soluble Granules (WG, SG)

50-80 wt % of a compound I or II or mixture according to the invention are ground finely with addition of up to 100 wt % dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I or II or mixture according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of a compound I or II or mixture according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

ix) Microemulsion (ME)

5-20 wt % of a compound I or II or mixture according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.

x) Microcapsules (CS)

An oil phase comprising 5-50 wt % of a compound I or II or mixture according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I or II or mixture according to the invention, 0-40 wt % water insoluble organic solvent (e.g. aromatic hydrocarbon), and an isocyanate monomer (e.g. diphenyl-methene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsule. The monomers amount to 1-10 wt %. The wt % relate to the total CS composition.

xi) Dustable Powders (DP, DS)

1-10 wt % of a compound I or II or mixture according to the invention are ground finely and mixed intimately with up to 100 wt % solid carrier, e.g. finely divided kaolin.

xii) Granules (GR, FG)

0.5-30 wt % of a compound I or II or mixture according to the invention is ground finely and associated with up to 100 wt % solid carrier (e.g. silicate). Granulation is achieved by extrusion, spray-drying or the fluidized bed.

xiii) Ultra-Low Volume Liquids (UL)

1-50 wt % of a compound I or II or mixture according to the invention are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active sub-stance. The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds of the present invention and/or mixing partners as defined above, may be mixed by the user in a spray tank and further auxiliaries and additives may be added, if appropriate.

In a further embodiment, either individual components of the composition according to the invention or partially premixed components, e.g. components comprising compounds of the present invention and/or mixing partners as defined above, can be applied jointly (e.g. after tank mix) or consecutively.

Application Methods

The compounds and mixtures of the present invention are suitable for use in protecting crops, plants, plant propagation materials, such as seeds, or soil or water, in which the plants are growing, from attack or infestation by animal pests. Therefore, the present invention also relates to a plant protection method, which comprises contacting crops, plants, plant propagation materials, such as seeds, or soil or water, in which the plants are growing, to be protected from attack or infestation by animal pests, with a pesticidally effective amount of a compound of the present invention.

The compounds and mixtures of the present invention are also suitable for use in combating or controlling animal pests. Therefore, the present invention also relates to a method of combating or controlling animal pests, which comprises contacting the animal pests, their habitat, breeding ground, or food supply, or the crops, plants, plant propagation materials, such as seeds, or soil, or the area, material or environment in which the animal pests are growing or may grow, with a pesticidally effective amount of a compound of the present invention.

The compounds and mixtures of the present invention are effective through both contact and ingestion. Furthermore, the compounds and mixtures of the present invention can be applied to any and all developmental stages, such as egg, larva, pupa, and adult.

The compounds and mixtures of the present invention can be applied as such or in form of compositions comprising them as defined above. Furthermore, the compounds and mixtures of the present invention can be applied together with a mixing partner as defined above or in form of compositions comprising said mixtures as defined above. The components of said mixture can be applied simultaneously, jointly or separately, or in succession, that is immediately one after another and thereby creating the mixture "in situ" on the desired location, e.g. the plant, the sequence, in the case of separate application, generally not having any effect on the result of the control measures.

The application can be carried out both before and after the infestation of the crops, plants, plant propagation materials, such as seeds, soil, or the area, material or environment by the pests.

Suitable application methods include inter alia soil treatment, seed treatment, in furrow application, water inlet application (e.g. in rice paddy fields during irrigation) and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active component I or II or mixture to the furrow, and closing the furrow. Foliar application refers to the application of the pesticidally active component I or II or mixture to plant foliage, e.g. through spray equipment. For foliar applications, it can be advantageous to modify the behavior of the pests by use of pheromones in combination with the compounds and mixtures of the present invention. Suitable pheromones for specific crops and pests are known to a skilled person and publicly available from databases of pheromones and semiochemicals, such as http://www.pherobase.com.

As used herein, the term "contacting" includes both direct contact (applying the compounds/compositions directly on the animal pest or plant—typically to the foliage, stem or roots of the plant) and indirect contact (applying the compounds/compositions to the locus, i.e. habitat, breeding ground, plant, seed, soil, area, material or environment in which a pest is growing or may grow, of the animal pest or plant).

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The term "crop" refers to both, growing and harvested crops.

The term "plant" includes cereals, e.g. durum and other wheat, rye, barley, triticale, oats, rice, or maize (fodder maize and sugar maize/sweet and field corn); beet, e.g. sugar beet or fodder beet; fruits, such as pomes, stone fruits or soft fruits, e.g. apples, pears, plums, peaches, nectarines, almonds, cherries, papayas, strawberries, raspberries, blackberries or gooseberries; leguminous plants, such as beans, lentils, peas, alfalfa or soybeans; oil plants, such as rapeseed (oilseed rape), turnip rape, mustard, olives, sunflowers, coconut, cocoa beans, castor oil plants, oil palms, ground nuts or soybeans; cucurbits, such as squashes, pumpkins, cucumber or melons; fiber plants, such as cotton, flax, hemp or jute; citrus fruit, such as oranges, lemons, grape-fruits or mandarins; vegetables, such as eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, such as avocados, cinnamon or camphor; energy and raw material plants, such as corn, soybean, rapeseed, sugar cane or oil palm; tobacco; nuts, e.g. walnuts; pistachios; coffee; tea; bananas; vines (table grapes and grape juice grape vines); hop; sweet leaf (also called Stevia); natural rubber plants or ornamental and forestry plants, such as flowers (e.g. carnation, petunias, geranium/pelargoniums, pansies and impatiens), shrubs, broad-leaved trees (e.g. poplar) or evergreens, e.g. conifers; eucalyptus; turf; lawn; grass such as grass for animal feed or ornamental uses. Preferred plants include potatoes sugar beets, tobacco, wheat, rye, barley, oats, rice, corn, cotton, soybeans, rapeseed, legumes, sunflowers, coffee or sugar cane; fruits; vines; ornamentals; or vegetables, such as cucumbers, tomatoes, beans or squashes.

The term "plant" is to be understood as including wild type plants and plants, which have been modified by either conventional breeding, or mutagenesis or genetic engineering, or by a combination thereof, in order to provide a new trait to a plant or to modify an already present trait.

Mutagenesis includes techniques of random mutagenesis using X-rays or mutagenic chemicals, but also techniques of targeted mutagenesis, in order to create mutations at a specific locus of a plant genome. Targeted mutagenesis techniques frequently use oligonucleotides or proteins like CRISPR/Cas, zinc-finger nucleases, TALENs or meganucleases to achieve the targeting effect.

Genetic engineering usually uses recombinant DNA techniques to create modifications in a plant genome which under natural circumstances cannot readily be obtained by cross breeding, mutagenesis or natural recombination. Typically, one or more genes are integrated into the genome of a plant in order to add a trait or improve a trait. These integrated genes are also referred to as transgenes in the art, while plant comprising such transgenes are referred to as transgenic plants. The process of plant transformation usually produces several transformation events, which differ in the genomic locus in which a transgene has been integrated. Plants comprising a specific transgene on a specific genomic locus are usually described as comprising a specific "event", which is referred to by a specific event name. Traits which have been introduced in plants or have been modified include in particular herbicide tolerance, insect resistance, increased yield and tolerance to abiotic conditions, like drought.

Herbicide tolerance has been created by using mutagenesis as well as using genetic engineering. Plants which have been rendered tolerant to acetolactate synthase (ALS) inhibitor herbicides by conventional methods of mutagenesis and breeding comprise plant varieties commercially available under the name Clearfield®. However, most of the herbicide tolerance traits have been created via the use of transgenes.

Herbicide tolerance has been created to glyphosate, glufosinate, 2,4-D, dicamba, oxynil herbicides, like bromoxynil and ioxynil, sulfonylurea herbicides, ALS inhibitor herbicides and 4-hydroxyphenylpyruvate dioxygenase (HPPD) inhibitors, like isoxaflutole and mesotrione.

Transgenes which have been used to provide herbicide tolerance traits comprise: for tolerance to glyphosate: cp4 epsps, epsps grg23ace5, mepsps, 2mepsps, gat4601, gat4621 and goxv247, for tolerance to glufosinate: pat and bar, for tolerance to 2,4-D: aad-1 and aad-12, for tolerance to dicamba: dmo, for tolerance to oxynil herbicies: bxn, for tolerance to sulfonylurea herbicides: zm-hra, csr1-2, gm-hra, S4-HrA, for tolerance to ALS inhibitor herbicides: csr1-2, for tolerance to HPPD inhibitor herbicides: hppdPF, W336 and avhppd-03.

Transgenic corn events comprising herbicide tolerance genes are for example, but not excluding others, DAS40278, MON801, MON802, MON809, MON810, MON832, MON87411, MON87419, MON87427, MON88017, MON89034, NK603, GA21, MZHG0JG, HCEM485, VCO-Ø1981-5, 676, 678, 680, 33121, 4114, 59122, 98140, Bt10, Bt176, CBH-351, DBT418, DLL25, MS3, MS6, MZIR098, T25, TC1507 and TC6275.

Transgenic soybean events comprising herbicide tolerance genes are for example, but not excluding others, GTS 40-3-2, MON87705, MON87708, MON87712, MON87769, MON89788, A2704-12, A2704-21, A5547-127, A5547-35, DP356043, DAS44406-6, DAS68416-4, DAS-81419-2, GU262, SYHTØH2, W62, W98, FG72 and CV127.

Transgenic cotton events comprising herbicide tolerance genes are for example, but not excluding others, 19-51a, 31707, 42317, 81910, 281-24-236, 3006-210-23, BXN10211, BXN10215, BXN10222, BXN10224, MON1445, MON1698, MON88701, MON88913, GHB119, GHB614, LLCotton25, T303-3 and T304-40.

Transgenic canola events comprising herbicide tolerance genes are for example, but not excluding others, MON88302, HCR-1, HCN10, HCN28, HCN92, MS1, MS8, PHY14, PHY23, PHY35, PHY36, RF1, RF2 and RF3.

Insect resistance has mainly been created by transferring bacterial genes for insecticidal proteins to plants. Transgenes which have most frequently been used are toxin genes of Bacillus spec. and synthetic variants thereof, like cry1A, cry1Ab, cry1Ab-Ac, cry1Ac, cry1A.105, cry1F, cry1Fa2, cry2Ab2, cry2Ae, mcry3A, ecry3.1Ab, cry3Bb1, cry34Ab1, cry35Ab1, cry9C, vip3A(a), vip3Aa20. However, also genes of plant origin have been transferred to other plants. In particular genes coding for protease inhibitors, like CpTI and pinII. A further approach uses transgenes in order to produce double stranded RNA in plants to target and downregulate insect genes. An example for such a transgene is dvsnf7.

Transgenic corn events comprising genes for insecticidal proteins or double stranded RNA are for example, but not excluding others, Bt10, Bt11, Bt176, MON801, MON802, MON809, MON810, MON863, MON87411, MON88017, MON89034, 33121, 4114, 5307, 59122, TC1507, TC6275, CBH-351, MIR162, DBT418 and MZIR098.

Transgenic soybean events comprising genes for insecticidal proteins are for example, but not excluding others, MON87701, MON87751 and DAS-81419.

Transgenic cotton events comprising genes for insecticidal proteins are for example, but not excluding others, SGK321, MON531, MON757, MON1076, MON15985, 31707, 31803, 31807, 31808, 42317, BNLA-601, Event1, COT67B, COT102, T303-3, T304-40, GFM Cry1A, GK12, MLS 9124, 281-24-236, 3006-210-23, GHB119 and SGK321.

Increased yield has been created by increasing ear biomass using the transgene athb17, being present in corn event MON87403, or by enhancing photosynthesis using the transgene bbx32, being present in the soybean event MON87712.

Cultivated plants comprising a modified oil content have been created by using the transgenes: gm-fad2-1, Pj.D6D, Nc.Fad3, fad2-1A and fatb1-A. Soybean events comprising at least one of these genes are: 260-05, MON87705 and MON87769.

Tolerance to abiotic conditions, in particular to tolerance to drought, has been created by using the transgene cspB, comprised by the corn event MON87460 and by using the transgene Hahb-4, comprised by soybean event IND-ØØ41Ø-5.

Traits are frequently combined by combining genes in a transformation event or by combining different events during the breeding process. Preferred combination of traits are herbicide tolerance to different groups of herbicides, insect tolerance to different kind of insects, in particular tolerance to lepidopteran and coleopteran insects, herbicide tolerance with one or several types of insect resistance, herbicide tolerance with increased yield as well as a combination of herbicide tolerance and tolerance to abiotic conditions.

Plants comprising singular or stacked traits as well as the genes and events providing these traits are well known in the art. For example, detailed information as to the mutagenized or integrated genes and the respective events are available from websites of the organizations "International Service for the Acquisition of Agri-biotech Applications (ISAAA)" (http://www.isaaa.org/gmapprovaldatabase) and the "Center for Environmental Risk Assessment (CERA)" (http://cera-gmc.org/GMCropDatabase), as well as in patent applications, like EP3028573 and WO2017/011288.

In one embodiment of the invention the plant is preferably rice plant (*Oryza* species, preferably *Oryza sativa*). Two species of rice are most frequently cultivated, *Oryza sativa* and *Oryza glaberrima*. Numerous subspecies of *Oryza sativa* are commercially important including *Oryza sativa* subsp. *indica*, *Oryza sativa* subsp. *japonica*, *Oryza sativa* subsp. *javanica*, *Oryza sativa* subsp. *glutinosa* (glutinous rice), *Oryza sativa Aromatica* group (e.g., basmati), and *Oryza sativa* (Floating rice group).

Plants, which have been modified by mutagenesis or genetic engineering, and are of particular commercial importance, include rice. In plants, which have been modified by mutagenesis or genetic engineering, one or more genes have been mutagenized or integrated into the genetic material of the plant. The one or more mutagenized or integrated genes are preferably selected from pat, epsps, cry1Ab, bar, cry1Fa2, cry1Ac, cry34Ab1, cry35AB1, cry3A, cryF, cry1F, mcry3a, cry2Ab2, cry3Bb1, cry1A.105, dfr, barnase, vip3Aa20, barstar, als, bxn, bp40, asn1, and ppo5. The mutagenesis or integration of the one or more genes is performed in order to improve certain properties of the plant. Such properties, also known as traits, include abiotic stress tolerance, altered growth/yield, disease resistance, herbicide tolerance, insect resistance, modified product quality, and pollination control. Of these properties, herbicide tolerance, e.g. imidazolinone tolerance, glyphosate tolerance, or glufosinate tolerance, is of particular importance.

It has surprisingly been found that the pesticidal activity of the compounds of the present invention may be enhanced by the insecticidal trait of a modified plant. Furthermore, it has been found that the compounds of the present invention are suitable for preventing insects to become resistant to the insecticidal trait or for combating pests, which already have become resistant to the insecticidal trait of a modified plant. Moreover, the compounds of the present invention are suitable for combating pests, against which the insecticidal trait is not effective, so that a complementary insecticidal activity can advantageously be used.

The use of compositions according to the invention on cultivated plants may result in effects which are specific to a cultivated plant comprising a certain gene or event. These effects might involve changes in growth behavior or changed resistance to biotic or abiotic stress factors. Such effects may in particular comprise enhanced yield, enhanced resistance or tolerance to insects, nematodes, fungal, bacterial, *mycoplasma*, viral or viroid pathogens as well as early vigour, early or delayed ripening, cold or heat tolerance as well as changed amino acid or fatty acid spectrum or content.

It has surprisingly been found that the pesticidal activity of the compounds and mixtures of the present invention may be enhanced by the insecticidal trait of a modified plant. Furthermore, it has been found that the compounds and mixtures of the present invention are suitable for preventing insects to become resistant to the insecticidal trait or for combating pests, which already have become resistant to the insecticidal trait of a modified plant. Moreover, the compounds and mixtures of the present invention are suitable for combating pests, against which the insecticidal trait is not effective, so that a complementary insecticidal activity can advantageously be used.

The term "plant propagation material" refers to all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "seed" embraces seeds and plant propagules of all kinds including but not limited to true seeds, seed pieces, suckers, corms, bulbs, fruit, tubers, grains, cuttings, cut shoots and the like, and means in a preferred embodiment true seeds.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment, in furrow application or of application to the pests dwelling place or nest, the quantity of active ingredient ranges from 0.0001 to 500 g per 100 m$^2$, preferably from 0.001 to 20 g per 100 m$^2$.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The compounds and mixtures of the present invention are particularly suitable for use in the treatment of seeds in order to protect the seeds from insect pests, in particular from soil-living insect pests, and the resulting seedling's roots and shoots against soil pests and foliar insects. The present invention therefore also relates to a method for the protection of seeds from insects, in particular from soil insects, and of the seedling's roots and shoots from insects, in particular from soil and foliar insects, said method comprising treating the seeds before sowing and/or after pregermination with a compound of the present invention. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active compound I or II or mixture is carried out by spraying or by dusting the seeds before sowing of the plants and before emergence of the plants.

The present invention also comprises seeds coated with or containing the active component I or a mixture thereof. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

The present invention also comprises a composition comprising seeds and the active component I or a mixture thereof.

The present invention also comprises a composition comprising seeds and the active non-racemic compound I, or a mixture thereof.

The present invention also comprises a composition comprising seeds and the active compound I with enantiomeric excess of compound I-R, preferably compound I-1 with enantiomeric excess of compound I-R-1, or a mixture thereof.

The present invention also comprises a composition comprising seeds and the active compound I-R, preferably compound I-R-1, or a mixture thereof.

Suitable seed is for example seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens*.

In addition, the active compound may also be used for the treatment of seeds from plants, which have been modified by mutagenesis or genetic engineering, and which e.g. tolerate the action of herbicides or fungicides or insecticides. Such modified plants have been described in detail above.

Conventional seed treatment formulations include for example flowable concentrates FS, solutions LS, suspoemulsions (SE), powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of the compounds and mixtures of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

In the treatment of seed, the application rates of the compounds of the invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising a compound of the present invention, or an agriculturally useful salt thereof, as defined herein. The amount of the compound of the present invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The compounds and mixtures of the present invention may also be used for improving the health of a plant. Therefore, the present invention also relates to a method for improving plant health by treating a plant, plant propagation material and/or the locus where the plant is growing or is to grow with an effective and non-phytotoxic amount of a compound of the present invention.

As used herein "an effective and non-phytotoxic amount" means that the component I or II or mixture is used in a quantity which allows to obtain the desired effect but which does not give rise to any phytotoxic symptom on the treated plant or on the plant grown from the treated propagule or treated soil.

The terms "plant" and "plant propagation material" are defined above.

"Plant health" is defined as a condition of the plant and/or its products which is determined by several aspects alone or in combination with each other such as yield (for example increased biomass and/or increased content of valuable ingredients), quality (for example improved content or composition of certain ingredients or shelf life), plant vigour (for example improved plant growth and/or greener leaves ("greening effect"), tolerance to abiotic (for example drought) and/or biotic stress (for example disease) and production efficiency (for example, harvesting efficiency, processability).

The above identified indicators for the health condition of a plant may be interdependent and may result from each other. Each indicator is defined in the art and can be determined by methods known to a skilled person.

The compounds of the invention are also suitable for use against non-crop insect pests. For use against said non-crop pests, compounds and mixtures of the present invention can be used as bait composition, gel, general insect spray, aerosol, as ultra-low volume application and bed net (impregnated or surface applied). Furthermore, drenching and rodding methods can be used.

As used herein, the term "non-crop insect pest" refers to pests, which are particularly relevant for non-crop targets, such as ants, termites, wasps, flies, ticks, mosquitos, crickets, or cockroaches, preferably mosquitos, more preferably yellow fever mosquitos.

The bait can be a liquid, a solid or a semisolid preparation (e.g. a gel). The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature (e.g. http://www.pherobase.com), and are known to those skilled in the art.

For use in bait compositions, the typical content of active ingredient is from 0.001 weight % to 15 weight %, desirably from 0.001 weight % to 5% weight % of active component I or mixture.

Formulations of the compounds and mixtures of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound I or mixture, solvents, furthermore auxiliaries such as emulsifiers, perfume oils, if appropriate stabilizers, and, if required, propellants.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds and mixtures of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds and mixtures of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder.

The compounds and mixtures of the present invention and its compositions can be used for protecting wooden materials such as trees, board fences, sleepers, frames, artistic artifacts, etc. and buildings, but also construction materials, furniture, leathers, fibers, vinyl articles, electric wires and cables etc. from ants and/or termites, and for controlling ants and termites from doing harm to crops or human being (e.g. when the pests invade into houses and public facilities).

Customary application rates in the protection of materials are, for example, from 0.001 g to 2000 g or from 0.01 g to 1000 g of active component I or mixture per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

Pests

The compounds of the present invention are especially suitable for efficiently combating animal pests such as arthropods, gastropods and nematodes including but not limited to:

insects from the order of Lepidoptera, for example *Achroia grisella, Acleris* spp. such as *A. fimbriana, A. gloverana, A. variana; Acrolepiopsis assectella, Acronicta major, Adoxophyes* spp. such as *A. cyrtosema, A. orana; Aedia leucomelas, Agrots* spp. such as *A. exclamationis, A. fucosa, A. ipsilon, A. orthogoma, A. segetum, A. subterranea; Alabama argillacea, Aleurodicus dispersus, Alsophila pometaria, Ampelophaga rubiginosa, Amyelois transitella, Anacampsis sarcitella, Anagasta kuehniella, Anarsia lineatella, Anisota senatoria, Antheraea pernyi, Anticarsia (=Thermesia)* spp. such as *A. gemmatali; Apamea* spp., *Aproaerema modicella, Archips* spp. such as *A. argyrospila, A. fuscocupreanus, A. rosana, A. xyloseanus; Argyresthia conjugella, Argyroploce* spp., *Argyrotaenia* spp. such as *A. velutinana; Athetis mindara, Austroasca viridigrisea, Autographa gamma, Autographa nigrisigna, Barathra brassicae, Bedellia* spp., *Bonagota salubricola, Borbo cinnara, Bucculatrix thurberiella, Bupalus piniarius, Busseola* spp., *Cacoecia* spp. such as *C. murinana, C. podana; Cactoblastis cactorum, Cadra cautella, Calingo braziliensis, Caloptilis theivora, Capua reticulana, Carposina* spp. such as *C. niponensis, C. sasakii; Cephus* spp., *Chaetocnema aridula, Cheimatobia brumata, Chilo* spp. such as *C. Indicus, C.*

*suppressalis, C. partellus; Choreutis pariana, Choristoneura* spp. such as *C. conflictana, C. fumiferana, C. longicellana, C. murinana, C. occidentalis, C. rosaceana; Chrysodeixis (=Pseudoplusia)* spp. such as *C. eriosoma, C. includens; Cirphis unipuncta, Clysia ambiguella, Cnaphalocerus* spp., *Cnaphalocrocis medinalis, Cnephasia* spp., *Cochylis hospes, Coleophora* spp., *Colias eurytheme, Conopomorpha* spp., *Conotrachelus* spp., *Copitarsia* spp., *Corcyra cephalonica, Crambus caliginosellus, Crambus teterrellus, Crocidosema (=Epinotia) aporema, Cydalima (=Diaphania) perspectalis, Cydia (=Carpocapsa)* spp. such as *C. pomonella, C. latiferreana; Dalaca noctuides, Datana integerrima, Dasychira pinicola, Dendrolimus* spp. such as *D. pini, D. spectabilis, D. sibiricus; Desmia funeralis, Diaphania* spp. such as *D. nitidalis, D. hyalinata; Diatraea grandiosella, Diatraea saccharalis, Diphthera festiva, Earias* spp. such as *E. insulana, E. vittella, Ecdytolopha aurantianu, Egira (=Xylomyges) curialis, Elasmopalpus lignosellus, Eldana saccharina, Endopiza viteana, Ennomos subsignaria, Eoreuma loftini, Ephestia* spp. such as *E. cautella, E. elutella, E. kuehniella; Epinotia aporema, Epiphyas postvittana, Erannis tiliaria, Erionota thrax, Etiella* spp., *Eulia* spp., *Eupoecilia ambiguella, Euproctis chrysorrhoea, Euxoa* spp., *Evetria bouliana, Faronta albilinea, Feltia* spp. such as *F. subterranean; Galleria mellonella, Gracillaria* spp., *Grapholita* spp. such as *G. funebrana, G. molesta, G. inopinata; Halysidota* spp., *Harrisina americana, Hedylepta* spp., *Helicoverpa* spp. such as *H. armigera (=Heliothis armigera), H. zea (=Heliothis zea); Heliothis* spp. such as *H. assulta, H. subflexa, H. virescens; Hellula* spp. such as *H. undalis, H. rogatalis; Helocoverpa gelotopoeon, Hemileuca oliviae, Herpetogramma licarsisalis, Hibernia defoliarna, Hofmannophila pseudospretella, Homoeosoma electellum, Homona magnanima, Hypena scabra, Hyphantria cunea, Hyponomeuta padella, Hyponomeuta malinellus, Kakivorna flavofasciata, Keiferia lycopersicella, Lambdina fiscellarna fiscellaria, Lambdina fiscellarna lugubrosa, Lamprosema indicata, Laspeyresia molesta, Leguminivora glycinivorella, Lerodea eufala, Leucinodes orbonalis, Leucoma salicis, Leucoptera* spp. such as *L. coffeella, L. scitella; Leuminivora lycinivorella, Lithocolletis blancardella, Lithophane antennata, Llattia octo (=Amyna axis), Lobesia botrana, Lophocampa* spp., *Loxagrotis albicosta, Loxostege* spp. such as *L. sticticalis, L. cereralis; Lymantria* spp. such as *L. dispar, L. monacha; Lyonetia clerkella, Lyonetia prunifoliella, Malacosoma* spp. such as *M. americanum, M. californicum, M. constrictum, M. neustria; Mamestra* spp. such as *M. brassicae, M. configurata; Mamstra brassicae, Manduca* spp. such as *M. quinquemaculata, M. sexta; Marasmia* spp, *Marmara* spp., *Maruca testulalis, Megalopyge lanata, Melanchra picta, Melanitis leda, Mocis* spp. such as *M. lapites, M. repanda; Mocis latipes, Monochroa fragariae, Mythimna separata, Nemapogon cloacella, Neoleucinodes elegantalis, Nepytia* spp., *Nymphula* spp., *Oiketicus* spp., *Omiodes indicata, Omphisa anastomosalis, Operophtera brumata, Orgyia pseudotsugata, Ora* spp., *Orthaga thyrisalis, Ostrinia* spp. such as *O. nubilalis; Oulema oryzae, Paleacrita vernata, Panolis flammea, Parnara* spp., *Papaipema nebris, Papilio cresphontes, Paramyelois transitella, Paranthrene regalis, Paysandisia archon, Pectinophora* spp. such as *P. gossypiella; Peridroma saucia, Perileucoptera* spp., such as *P. coffeella; Phalera bucephala, Phryganidia californica, Phthornmaea* spp. such as *P. operculella; Phyllocnistis citrella, Phyllonorycter* spp. such as *P. blancardella, P. crataegella, P. issikii, P. ringoniella; Pieris* spp. such as *P. brassicae, P. rapae, P. napi; Pilocrocis trpunctata, Plathypena scabra, Platynota* spp. such as *P. flavedana, P. idaeusalis, P. stultana; Platyptilia carduidactyla, Plebejus argus, Plodia interpunctella, Plusia* spp, *Plutella maculipennis, Plutella xylostella, Pontia protodica, Prays* spp., *Prodenia* spp., *Proxenus lepigone, Pseudaletia* spp. such as *P. sequax, P. unipuncta; Pyrausta nubilalis, Rachiplusia nu, Richia albicosta, Rhizobius ventralis, Rhyacionia frustrana, Sabulodes aegrotata, Schizura concinna, Schoenobius* spp., *Schreckensteinia festaliella, Scirpophaga* spp. such as *S. incertulas, S. innotata; Scotia segetum, Sesamia* spp. such as *S. inferens, Seudyra subflava, Sitotroga cerealella, Sparganothis pilleriana, Spilonota lechriaspis, S. ocellana, Spodoptera (=Lamphygma)* spp. such as *S. cosmoides, S. eridania, S. exigua, S. frugiperda, S. latisfascia, S. littoralis, S. litura, S. omithogalli; Stigmella* spp., *Stomopteryx subsecivella, Strymon bazochii, Sylepta derogata, Synanthedon* spp. such as *S. exitiosa, Tecia solanivora, Telehin licus, Thaumatopoea pityocampa, Thaumatotibia (=Cryptophlebia) leucotreta, Thaumetopoea pityocampa, Thecla* spp., *Theresimima ampelophaga, Thyrinteina* spp, *Tildenia inconspicuella, Tinea* spp. such as *T. cloacella, T. pellionella; Tineola bisselliella, Tortrix* spp. such as *T. viridana; Trichophaga tapetzella, Trichoplusia* spp. such as *T. ni; Tuta (=Scrobipalpula) absoluta, Udea* spp. such as *U. rubigalis, U. rubigalis; Virachola* spp., *Yponomeuta padella*, and *Zeiraphera canadensis;* insects from the order of Coleoptera, for example *Acalymma vittatum, Acanthoscehdes obtectus, Adoretus* spp., *Agelastica alni, Agrilus* spp. such as *A. anxius, A. planipennis, A. sinuatus; Agriotes* spp. such as *A. fuscicollis, A. lineatus, A. obscurus; Alphitobius diaperinus, Amphimallus solstitialis, Anisandrus dispar, Anisoplia austriaca, Anobium punctatum, Anomala corpulenta, Anomala rufocuprea, Anoplophora* spp. such as *A. glabriDennis Anthonomus* spp. such as *A. eugenii, A. grandis, A. pomorum; Anthrenus* spp., *Aphthona euphoridae, Apion* spp., *Apogonia* spp., *Athous haemorrhoidalis, Atomarna* spp. such as *A. linearis; Attagenus* spp., *Aulacophora femoralis, Blastophagus piniperda, Blitophaga undata, Bruchidius obtectus, Bruchus* spp. such as *B. lentis, B. pisorum, B. rufimanus; Byctiscus betulae, Callidiellum rufipenne, Callopistria floridensis, Callosobruchus chinensis, Cameraria ohridella, Cassida nebulosa, Cerotoma trifurcata, Cetonia aurata, Ceuthorhynchus* spp. such as *C. assimilis, C. napi; Chaetocnema tibialis, Cleonus mendicus, Conoderus* spp. such as *C. vespertinus; Conotrachelus nenuphar, Cosmopolites* spp., *Costelytra zealandica, Crioceris asparagi, Cryptolestes ferrugineus, Cryptorhynchus lapathi, Ctenicera* spp. such as *C. destructor; Curculio* spp., *Cylindrocopturus* spp., *Cyclocephala* spp., *Dactylispa balyi, Dectes texanus, Dermestes* spp., *Diabrotica* spp. such as *D. undecimpunctata, D. speciosa, D. longicornis, D. semipunctata, D. virgifera; Diaprepes abbreviates, Dichocrocis* spp., *Dicladispa armigera, Diloboderus abderus, Diocalandra frumenti (Diocalandra stigmaticollis), Enaphalodes rufulus, Epilachna* spp. such as *E. varivestis, E. vigintioctomaculata; Epitrx* spp. such as *E. hirtipennis, E. similarns; Eutheola humilis, Eutinobothrus brasiliensis, Faustinus cubae, Gibbium psylloides, Gnathocerus cornutus, Hellula undalis, Heteronychus arator, Hylamorpha elegans, Hylobius abietis, Hylotrupes bajulus, Hypera* spp. such as *H. brunneipennis, H. postica; Hypomeces squamosus, Hypothenemus* spp., *Ips typographus, Lachnosterna consanguinea, Lasioderma serricore, Latheticus oryzae, Lathridius* spp., *Lema* spp. such as *L. bilineata, L. melanopus; Leptinotarsa* spp. such as *L. decemlineata; Leptispa pygmaea, Limonius californicus, Lissorhoptrus oryzophilus, Lixus* spp., *Luperodes* spp., *Lyctus* spp. such as *L. bruneus*; *Liogenys fuscus*, *Macrodactylus* spp. such as *M. subspinosus*; *Maladera matrida*, *Megaplatypus mutates*, *Megascelis* spp., *Melanotus communis*, *Meligethes* spp. such as *M. aeneus*, *Melolontha* spp. such as *M. hippocastani*, *M. melolontha*; *Metamasius hemipterus*, *Microtheca* spp., *Migdolus* spp. such as *M. fryanus*, *Monochamus* spp. such as *M. alternatus*, *Naupactus xanthographus*, *Niptus hololeucus*, *Oberia brevis*, *Oemona hirta*, *Oryctes rhinoceros*, *Oryzaephilus surinamensis*, *Oryzaphagus oryzae*, *Otiorrhynchus sulcatus*, *Otiorrhynchus ovatus*, *Otiorrhynchus sulcatus*, *Oulema melanopus*, *Oulema oryzae*, *Oxycetonia jucunda*, *Phaedon* spp. such as *P. brassicae*, *P. cochleariae*; *Phoracantha recurva*, *Phyllobius pyri*, *Phyllopertha horticola*, *Phyllophaga* spp. such as *P. helleri*; *Phyllotreta* spp. such as *P. chrysocephala*, *P. nemorum*, *P. striolata*, *P. vittula*; *Phyllopertha horticola*, *Popillia japonica*, *Premnotrypes* spp., *Psacothea hilaris*, *Psylliodes chrysocephala*, *Prostephanus truncates*, *Psylliodes* spp., *Ptinus* spp., *Pulga saltona*, *Rhizopertha dominica*, *Rhynchophorus* spp. such as *R. billineatus*, *R. ferrugineus*, *R. palmarum*, *R. phoenicis*, *R. vulneratus*, *Saperda candida*, *Scolytus schevyrewi*, *Scyphophorus acupunctatus*, *Sitona lineatus*, *Sitophilus* spp. such as *S. granaria*, *S. oryzae*, *S. zeamais*; *Sphenophorus* spp. such as *S. levis*; *Stegobium paniceum*, *Sternechus* spp. such as *S. subsignatus*, *Strophomorphus ctenotus*, *Symphyletes* spp., *Tanymecus* spp., *Tenebrio molitor*, *Tenebrioides mauretanicus*, *Tribolium* spp. such as *T. castaneum*; *Trogoderma* spp., *Tychius* spp., *Xylotrechus* spp. such as *X. pyrrhoderus*, and, *Zabrus* spp. such as *Z. tenebrioides*, insects from the order of Diptera for example *Aedes* spp. such as *A. aegypti*, *A. albopictus*, *A. vexans*; *Anastrepha ludens*, *Anopheles* spp. such as *A. albimanus*, *A. crucians*, *A. freeborni*, *A. gambiae*, *A. leucosphyrus*, *A. maculipennis*, *A. minimus*, *A. quadrimaculatus*, *A. sinensis*; *Bactrocera invadens*, *Biblo hortulanus*, *Calliphora erythrocephala*, *Calliphora vicina*, *Ceratitis capitata*, *Chrysomyia* spp. such as *C. bezziana*, *C. hominivorax*, *C. macellaria*; *Chrysops atlanticus*, *Chrysops discalis*, *Chrysops silacea*, *Cochliomyia* spp. such as *C. hominivorax*; *Contarinia* spp. such as *C. sorghicola*; *Cordylobia anthropophaga*, *Culex* spp. such as *C. nigripalpus*, *C. piens*, *C. quinquefasciatus*, *C. tarsalis*, *C. tritaeniorhynchus*; *Culicoides furens*, *Culiseta inornata*, *Culiseta melanura*, *Cuterebra* spp., *Dacus cucurbitae*, *Dacus oleae*, *Dasineura brassicae*, *Dasineura oxycoccana*, *Delia* spp. such as *D. antique*, *D. coarctata*, *D. platura*, *D. radicum*; *Dermatobia hominis*, *Drosophila* spp. such as *D. suzukii*, *Fannia* spp. such as *F. canicularis*; *Gastraphilus* spp. such as *G. intestinalis*; *Geomyza tipunctata*, *Glossina* spp. such as *G. fuscipes*, *G. morsitans*, *G. palpalis*, *G. tachinoides*; *Haematobia irritans*, *Haplodiplosis equestris*, *Hippelates* spp., *Hylemyia* spp. such as *H. platura*; *Hypoderma* spp. such as *H. lineata*; *Hyppobosca* spp., *Hydrellia philippina*, *Leptoconops torrens*, *Liriomyza* spp. such as *L. sativae*, *L. trifolii*; *Lucilia* spp. such as *L. caprina*, *L. cuprina*, *L. sericata*; *Lycoria pectoralis*, *Mansonia titillanus*, *Mayetiola* spp. such as *M. destructor*; *Musca* spp. such as *M. autumnalis*, *M. domestica*; *Muscina stabulans*, *Oestrus* spp. such as *O. ovis*; *Opomyza florum*, *Oscinella* spp. such as *O. frit*; *Orseolia oryzae*, *Pegomya hysocyami*, *Phlebotomus argentipes*, *Phorbia* spp. such as *P. antiqua*, *P. brassicae*, *P. coarctata*; *Phytomyza gymnostoma*, *Prosimulium mixtum*, *Psila rosae*, *Psorophora columbiae*, *Psorophora discolor*, *Rhagoletis* spp. such as *R. cerasi*, *R. cingulate*, *R. indifferens*, *R. mendax*, *R. pomonella*; *Rivellia quadrifasciata*, *Sarcophaga* spp. such as *S. haemorrhoidalis*; *Simulium vittatum*, *Sitodiplosis mosellana*, *Stomoxys* spp. such as *S. calcitrans*; *Tabanus* spp. such as *T. atratus*, *T. bovinus*, *T. lineola*, *T. similis*; *Tannia* spp., *Thecodiplosis japonensis*, *Tipula oleracea*, *Tipula paludosa*, and *Wohlfahrtia* spp;

insects from the order of Thysanoptera for example, *Baliothrips biformis*, *Dichromothrips corbetti*, *Dichromothrips* ssp., *Echinothrips americanus*, *Enneothrips flavens*, *Frankliniella* spp. such as *F. fusca*, *F. occidentalis*, *F. tritici*; *Heliothrips* spp., *Hercinothrips femoralis*, *Kakothrips* spp., *Microcephalothrips abdominalis*, *Neohydatothrips samayunkur*, *Pezothrips kellyanus*, *Rhipiphorothrips cruentatus*, *Scirtothrips* spp. such as *S. citri*, *S. dorsalis*, *S. perseae*; *Stenchaetothrips* spp, *Taeniothrips cardamoni*, *Taeniothrips inconsequens*, *Thrips* spp. such as *T. imagines*, *T. hawaiiensis*, *T. oryzae*, *T. palmi*, *T. parvispinus*, *T. tabaci*;

insects from the order of Hemiptera for example, *Acizzia jamatonica*, *Acrosternum* spp. such as *A. hilare*; *Acyrthosipon* spp. such as *A. onobrychis*, *A. pisum*; *Adelges laricis*, *Adelges tsugae*, *Adelphocoris* spp., such as *A. rapidus*, *A. superbus*; *Aeneolamia* spp., *Agonoscena* spp., *Aulacorthum solani*, *Aleurocanthus woglumi*, *Aleurodes* spp., *Aleurodicus disperses*, *Aleurolobus barodensis*, *Aleurothrixus* spp., *Amrasca* spp., *Anasa tristis*, *Antestiopsis* spp., *Anuraphis cardui*, *Aonidiella* spp., *Aphanostigma piri*, *Aphidula nasturtii*, *Aphis* spp. such as *A. craccivora*, *A. fabae*, *A. forbesi*, *A. gossypii*, *A. grossulariae*, *A. maidiradicis*, *A. pomi*, *A. sambuci*, *A. schneideri*, *A. spiraecola*; *Arboridia apicalis*, *Arilus critatus*, *Aspidiella* spp., *Aspidiotus* spp., *Atanus* spp., *Aulacaspis yasumatsui*, *Aulacorthum solani*, *Bactericera cockerelli (Paratrioza cockerelli)*, *Bemisia* spp. such as *B. argentifolii*, *B. tabaci (Aleurodes tabaci)*; *Blissus* spp. such as *B. leucopterus*; *Brachycaudus* spp. such as *B. cardui*, *B. helichrysi*, *B. persicae*, *B. prunicola*; *Brachycolus* spp., *Brachycorynella asparagi*, *Brevicoryne brassicae*, *Cacopsylla* spp. such as *C. fulguralis*, *C. pyricola (Psylla piri)*, *Calliqypona marginata*, *Calocoris* spp., *Campylomma livida*, *Capitophorus horni*, *Carneocephala fulgida*, *Caveerius* spp., *Ceraplastes* spp., *Ceratovacuna lanigera*, *Ceroplastes ceriferus*, *Cerosipha gossypii*, *Chaetosiphon fragaefolii*, *Chionaspis tegalensis*, *Chlornta onukii*, *Chromaphis juglandicola*, *Chrysomphalus ficus*, *Cicadulina mbila*, *Cimex* spp. such as *C. hemipterus*, *C. lectularius*; *Coccomytilus halli*, *Coccus* spp. such as *C. hesperidum*, *C. pseudomagnoliarum*; *Corythucha arcuata*, *Creontiades dilutus*, *Cryptomyzus ribis*, *Chrysomphalus aonidum*, *Cryptomyzus ribis*, *Ctenarytaina spatulata*, *Cyrtopeltis notatus*, *Dalbulus* spp., *Dasynus piperis*, *Dialeurodes* spp. such as *D. citrifolii*; *Dalbulus maidis*, *Diaphorina* spp. such as *D. citri*; *Diaspis* spp. such as *D. bromeliae*; *Dichelops furcatus*, *Diconocoris hewetti*, *Doralis* spp., *Dreyfusia nordmannianae*, *Dreyfusia piceae*, *Drosicha* spp., *Dysaphis* spp. such as *D. plantaginea*, *D. pyri*, *D. radicola*; *Dysaulacorthum pseudosolani*, *Dysdercus* spp. such as *D. cingulatus*, *D. intermedius*; *Dysmicoccus* spp., *Edessa* spp., *Geocoris* spp., *Empoasca* spp. such as *E. fabae*, *E. solana*; *Epidiaspis leperii*, *Eriosoma* spp. such as *E. lanigerum*, *E. pyricola*; *Erythroneura* spp., *Eurygaster* spp. such as *E. integriceps*; *Euscelis bilobatus*, *Euschistus* spp. such as *E. heros*, *E. impictiventris*, *E. servus*; *Fiorinia theae*, *Geococcus coffeae*, *Glycaspis brimblecombei*, *Halyomorpha* spp. such as *H. halys*; *Heliopeltis* spp., *Homalodisca vitrpennis (=H. coagulata)*, *Horcias nobilellus*, *Hyalopterus pruni*, *Hyperomyzus lactucae*, *Icerya* spp. such as *I. purchase*; *Idiocerus* spp., *Idioscopus* spp., *Laodelphax striatellus*, *Lecanium* spp., *Lecanoideus floccissimus*, *Lepidosaphes* spp. such as *L. ulmi*; *Leptocorisa* spp., *Leptoglossus phyllopus*, *Lipaphis erysimi*, *Lygus* spp. such as *L. hesperus*, *L. lineolaris*, *L. pratensis*; *Maconellic-* occus hirsutus, Marchalina hellenica, Macropes excavatus, Macrosiphum spp. such as M. rosae, M. avenae, M. euphorbiae; Macrosteles quadrilineatus, Mahanarva fimbriolata, Megacopta cribraria, Megoura viciae, Melanaphis pyrarius, Melanaphis sacchari, Melanocallis (=Tinocallis) caryaefoliae, Metcafiella spp., Metopolophium dirhodum, Monellia costalis, Monelliopsis pecanis, Myzocallis coryli, Murgantia spp., Myzus spp. such as M. ascalonicus, M. cerasi, M. nicotianae, M. persicae, M. varians; Nasonovia ribis-nigri, Neotoxoptera formosana, Neomegalotomus spp, Nephotettix spp. such as N. malayanus, N. nigropictus, N. parvus, N. virescens; Nezara spp. such as N. viridula; Nilaparvata lugens, Nysius huttoni, Oebalus spp. such as O. pugnax; Oncometopia spp., Orthezia praelonga, Oxycaraenus hyalinipennis, Parabemisia myricae, Parlatoria spp., Parthenolecanium spp. such as P. corn, P. persicae; Pemphigus spp. such as P. bursarius, P. populivenae; Peregrinus maidis, Perkinsiella saccharicida, Phenacoccus spp. such as P. aceris, P. gossypii; Phloeomyzus passerinii, Phorodon humuli, Phylloxera spp. such as P. devastatrk, Piesma quadrata, Piezodorus spp. such as P. guildinii; Pinnaspis aspidistrae, Planococcus spp. such as P. citri, P. ficus; Prosapia bicincta, Protopulvinaria pyriformis, Psallus seriatus, Pseudacysta persea, Pseudaulacaspis pentagona, Pseudococcus spp. such as P. comstocki; Psylla spp. such as P. mali; Pteromalus spp., Pulvinaria amygdali, Pyrilla spp., Quadraspidiotus spp., such as Q. perniciosus; Quesada gigas, Rastrococcus spp., Reduvius senilis, Rhizoecus americanus, Rhodnius spp., Rhopalomyzus ascalonicus, Rhopalosiphum spp. such as R. pseudobrassicas, R. insertum, R. maidis, R. padi; Sagatodes spp., Sahlbergella singularis, Saissetia spp., Sappaphis mala, Sappaphis mal, Scaptocoris spp., Scaphoides tanus, Schizaphis graminum, Schizoneura lanuginosa, Scotinophora spp., Selenaspidus articulatus, Sitobion avenae, Sogata spp., Sogatella furcifera, Solubea insularis, Spissistilus festinus (=Stictocephala festina), Stephanitis nashi, Stephanitis pyrioides, Stephanitis takeyai, Tenalaphara malayensis, Tetraleurodes perseae, Therioaphis maculate, Thyanta spp. such as T. accerra, T. perditor; Tibraca spp., Tomaspis spp., Toxoptera spp. such as T. aurantii; Trialeurodes spp. such as T. abutilonea, T. ricini, T. vaporariorum; Triatoma spp., Trioza spp., Typhlocyba spp., Unaspis spp. such as U. citri, U. yanonensis; and Viteus vitifolii, Insects from the order Hymenoptera for example Acanthomyops interjectus, Athalia rosae, Atta spp. such as A. capiguara, A. cephalotes, A. cephalotes, A. laevigata, A. robusta, A. sexdens, A. texana, Bombus spp., Brachymyrmex spp., Camponotus spp. such as C. floridanus, C. pennsylvanicus, C. modoc; Cardiocondyla nuda, Chalibion sp, Crematogaster spp., Dasymutilla occidentalis, Diprion spp., Dolichovespula maculata, Dorymyrmex spp., Dryocosmus kuriphilus, Formica spp., Hoplocampa spp. such as H. minuta, H. testudinea; Iridomyrmex humilis, Lasius spp. such as L. niger, Linepithema humile, Liometopum spp., Leptocybe invasa, Monomorium spp. such as M. pharaonis, Monomorium, Nylandria fulva, Pachycondyla chinensis, Paratrechina longicornis, Paravespula spp., such as P. germanica, P. pennsylvanica, P. vulgaris; Pheidole spp. such as P. megacephala; Pogonomyrmex spp. such as P. barbatus, P. californicus, Polistes rubiginosa, Prenolepis impairs, Pseudomyrmex gracilis, Schelipron spp., Sirex cyaneus, Solenopsis spp. such as S. geminata, S.invicta, S. molesta, S. richteri, S. xyloni, Sphecius speciosus, Sphex spp., Tapinoma spp. such as T. melanocephalum, T. sessile; Tetramorium spp. such as T. caespitum, T. bicarinatum, Vespa spp. such as V. crabro; Vespula spp. such as V. squamosal; Wasmannia auropunctata, Xylocopa sp;

Insects from the order Orthoptera for example Acheta domesticus, Calliptamus italicus, Chortoicetes terminifera, Ceuthophilus spp., Diastrammena asynamora, Dociostaurus maroccanus, Gryllotalpa spp. such as G. africana, G. gryllotalpa; Gryllus spp., Hieroglyphus daganensis, Kraussaria angulifera, Locusta spp. such as L. migratoria, L. pardalina; Melanoplus spp. such as M. bivittatus, M. femurrubrum, M. mexicanus, M. sanguinipes, M. spretus; Nomadacris septemfasciata, Oedaleus senegalensis, Scapteriscus spp., Schistocerca spp. such as S. americana, S. gregaria, Stemopelmatus spp., Tachycines asynamorus, and Zonozerus variegatus;

Pests from the Class Arachnida for example Acari, e.g. of the families Argasidae, Ixodidae and Sarcoptidae, such as Amblyomma spp. (e.g. A. americanum, A. variegatum, A. maculatum), Argas spp. such as A. persicu), Boophilus spp. such as B. annulatus, B. decoloratus, B. microplus, Dermacentor spp. such as D. silvarum, D. andersoni, D. variabilis, Hyalomma spp. such as H. truncatum, Ixodes spp. such as I. ricinus, I. rubicundus, I. scapularIs, I. holocyclus, I. pacificus, Rhipicephalus sanguineus, Ornithodorus spp. such as O. moubata, O. hermsi, O. turicata, Ornithonyssus bacoti, Otobius megnini, Dermanyssus gallinae, Psoroptes spp. such as P. ovis, Rhipicephalus spp. such as R. sanguineus, R. appendiculatus, Rhipicephalus evertsi, Rhizoglyphus spp., Sarcoptes spp. such as S. Scabiei; and Family Eriophyidae including Aceria spp. such as A. sheldoni, A. anthocoptes, Acallitus spp., Aculops spp. such as A. lycopersici, A. pelekassi; Aculus spp. such as A. schlechtendali; Colomerus vitis, Epitrimerus pyri, Phyllocoptruta oleivora; Eriophytes ribis and Eriophyes spp. such as Eriophyes sheldoni Family Tarsonemidae including Hemitarsonemus spp., Phytonemus pallidus and Polyphagotarsonemus latus, Stenotarsonemus spp. Steneotarsonemus spinkr; Family Tenuipalpidae including Brevipalpus spp. such as B. phoenicis; Family Tetranychidae including Eotetranychus spp., Eutetranychus spp., Oligonychus spp., Petrobia latens, Tetranychus spp. such as T. cinnabarinus, T. evansi, T. kanzawai, T. pacificus, T. phaseulus, T. telarius and T. urticae; Bryobia praetiosa; Panonychus spp. such as P. ulmi, P. citrr; Metatetranychus spp. and Oligonychus spp. such as O. pratensis, O. perseae, Vasates lycopersici; Raoiella indica, Family Carpoglyphidae including Carpoglyphus spp.; Penthaleidae spp. such as Halotydeus destructor, Family Demodicidae with species such as Demodex spp.; Family Trombicidea including Trombicula spp.; Family Macronyssidae including Ornothonyssus spp.; Family Pyemotidae including Pyemotes tritici; Tyrophagus putrescentiae; Family Acaridae including Acarus siro; Family Araneida including Latrodectus mactans, Tegenaria agrestis, Chiracanthium sp, Lycosa sp Achaearanea tepidariorum and Loxosceles reclusa;

Pests from the Phylum Nematoda, for example, plant parasitic nematodes such as root-knot nematodes, Meloidogyne spp. such as M. hapla, M. incognita, M. javanica; cyst-forming nematodes, Globodera spp. such as G. rostochiensis; Heterodera spp. such as H. avenae, H. glycines, H. schachtii, H. trifolii; Seed gall nematodes, Anguina spp.; Stem and foliar nematodes, Aphelenchoides spp. such as A. besseyi; Sting nematodes, Belonolaimus spp. such as B. longicaudatus; Pine nematodes, Bursaphelenchus spp. such as B. lignicolus, B. xylophilus; Ring nematodes, Criconema spp., Criconemella spp. such as C. xenoplax and C. ornata; and, Criconemoides spp. such as Criconemoides informis; Mesocriconema spp.; Stem and bulb nematodes, Ditylen-

*chus* spp. such as *D. destructor, D. dipsaci*; Awl nematodes, *Dolichodorus* spp.; Spiral nematodes, *Heliocotylenchus multicinctus*; Sheath and sheathoid nematodes, *Hemicycliophora* spp. and *Hemicriconemoides* spp.; *Hirshmanniella* spp.; Lance nematodes, *Hoploaimus* spp.; False rootknot nematodes, *Nacobbus* spp.; Needle nematodes, *Longidorus* spp. such as *L. elongatus*; Lesion nematodes, *Pratylenchus* spp. such as *P. brachyurus, P. neglectus, P. penetrans, P. curvitatus, P. goodeyi*; Burrowing nematodes, *Radopholus* spp. such as *R. similis*; *Rhadopholus* spp.; *Rhodopholus* spp.; Reniform nematodes, *Rotylenchus* spp. such as *R. robustus, R. reniformis*; *Scutellonema* spp.; Stubby-root nematode, *Trichodorus* spp. such as *T. obtusus, T. primitivus*; *Paratrichodorus* spp. such as *P. minor*; Stunt nematodes, *Tylenchorhynchus* spp. such as *T. claytoni, T. dubius*; Citrus nematodes, *Tylenchulus* spp. such as *T. semipenetrans*; Dagger nematodes, *Xiphinema* spp.; and other plant parasitic nematode species;

Insects from the order Isoptera for example *Calotermes flavicollis, Coptotermes* spp. such as *C. formosanus, C. gestroi, C. acinaciformis*; *Cornitermes cumulans, Cryptotermes* spp. such as *C. brevis, C. cavifrons*; *Globitermes sulfureus, Heterotermes* spp. such as *H. aureus, H. longiceps, H. tenuis*; *Leucotermes flavipes, Odontotermes* spp., *Incisitermes* spp. such as *I. minor, I. Snyder, Marginitermes hubbardi, Mastotermes* spp. such as *M. darwiniensis Neocapritermes* spp. such as *N. opacus, N. parvus*; *Neotermes* spp., *Procornitermes* spp., *Zootermopsis* spp. such as *Z. angusticollis, Z. nevadensis, Reticulitermes* spp. such as *R. hesperus, R. tibialis, R. speratus, R. flavipes, R. grassei, R. lucifugus, R. santonensis, R. virginicus*; *Termes natalensis*, Insects from the order Blattaria for example *Blatta* spp. such as *B. orientalis, B. lateralis*; *Blattella* spp. such as *B. asahinae, B. germanica*; *Leucophaea maderae, Panchlora nivea, Periplaneta* spp. such as *P. americana, P. australasiae, P. brunnea, P. fuligginosa, P. japonica*; *Supella longipalpa, Parcoblatta pennsylvanica, Eurycotis floridana, Pycnoscelus surinamensis*, Insects from the order Siphonoptera for example *Cediopsylla simples, Ceratophyllus* spp., *Ctenocephalides* spp. such as *C. felis, C. canis, Xenopsylla cheopis, Pulex irritans, Trichodectes canis, Tunga penetrans*, and *Nosopsyllus fasciatus*, Insects from the order Thysanura for example *Lepisma saccharina, Ctenolepisma urbana*, and *Thermobia domestica*, Pests from the class Chilopoda for example *Geophilus* spp., *Scutigera* spp. such as *Scutigera coleoptrata*;

Pests from the class Diplopoda for example *Blaniulus guttulatus, Julus* spp., *Narceus* spp., Pests from the class Symphyla for example *Scutigerella immaculata*, Insects from the order Dermaptera, for example *Forficula auricularia*, Insects from the order Collembola, for example *Onychiurus* spp., such as *Onychiurus armatus*, Pests from the order Isopoda for example, *Armadillidium vulgare, Oniscus asellus, Porcellio scaber*, Insects from the order Phthiraptera, for example *Damalinia* spp., *Pediculus* spp. such as *Pediculus humanus capitis, Pediculus humanus corporis, Pediculus humanus humanus*; *Pthirus pubis, Haematopinus* spp. such as *Haematopinus eurysternus, Haematopinus suis*; *Linognathus* spp. such as *Linognathus vituli*; *Bovicola bovis, Menopon gallinae, Menacanthus stramineus* and *Solenopotes capillatus, Trichodectes* spp., Examples of further pest species which may be controlled by compounds of formula (I) include: from the Phylum Mollusca, class Bivalvia, for example, *Dreissena* spp.; class Gastropoda, for example, *Arion* spp., *Biomphalaria* spp., *Bulinus* spp., *Deroceras* spp., *Galba* spp., *Lymnaea* spp., *Oncomelania* spp., *Pomacea canaliclata, Succinea* spp.; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus*; *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti*.

In one embodiment of the invention, pests are from the order of Hemiptera, Lepidoptera, Coleoptera, or Thysanoptera, preferably selected from *Trialeurodes* spp., *Nephotettix* spp., *Nezara* spp., *Aphis* spp., *Megoura viciae, Myzus* spp., *Heliothis* spp., *Chilo* spp., *Scirpophaga* spp., *Anthonomus* spp., or *Thrips(dichromothrips corbetti)*, more preferably are Greenhouse Whitefly (*Trialeurodes vaporariorum*), green leafhopper (*Nephotettix virescens*), Rice brown plant hopper (*Nilaparvata lugens*), Cowpea aphid (*Aphis craccivora*), vetch aphid (*Megoura viciae*), green peach aphid (*Myzus persicae*), tobacco budworm (*Heliothis virescens*), rice stem borer/striped stem borer—*Chilo suppressalis*, yellow rice borer—*Tryporyza* (=*Scirpophaga*) *incertulas*, boll weevil (*Anthonomus grandis*), or *Thrips* (*dichromothrips corbeti*);

In one embodiment of the invention, the invention relates to method of controlling rice pest invertebrates in rice, which method comprises applying to said rice pest invertebrates at least one pesticidally active non-racemic compound (I) or enantiomers thereof, or the mixtures thereof.

In one embodiment of the invention, the invention relates to method of controlling rice pest invertebrates in rice, which method comprises applying to said rice pest invertebrates at least one pesticidally active compound of formula (I) with enantiomeric excess of compound I-R, or the mixtures thereof.

In one embodiment of the invention, the invention relates to method of controlling rice pest invertebrates in rice, which method comprises applying to said rice pest invertebrates at least one pesticidally active compound I-R, or the mixtures thereof.

Rice Pests:

In the context of this invention, rice pest invertebrates are animal pests, which occur in rice. The rice pest invertebrates include insects, acarids and nematodes, preferably insects. Rice pest invertebrates, which are well-known in rice, include but are not limited to the following species:

Hemiptera:
brown planthopper—*Nilaparvata lugens*
small brown planthopper—*Laodelphax striatellus*
white-backed planthopper—*Sogatella furcifera*
white leafhopper—*Cofana spectra* green leafhopper—*Nephotettix virescens, N. nigriceps, N. cincticeps, N. malayanus*
    zig zag leafhopper—*Recilia dorsalis*
    maize orange leafhopper—*Cicadulina bipunctata*
    aster leafhopper—*Macrosteles fascifrons*
    rice earhead bug, *Leptocorisa oratorius, L. acuta*
    rice stink bugs—*Nezara viridula, Pygomenida varipennis, Eysarcoris, Tibraca limbatriventris, Eysarcoris ventralis*
    small stink bug—*Oebalus poecilus, O. pugnax*
    coreid bug—*Eysarcoris sp*
    chinch bug—*Blissus leucopterus leucopterus*
    rice mealybug, *Brevennia rehi, Pseudococcus saccharicola*
    rice aphids, *Rhopalosiphum rufiabdominalis, Macrosiphum avenae, Hysteroneura setariae, Tetraneuro nigriabdominalis*
    bean root aphid—*Smynthurodes betae*
Lepidoptera:
    rice skipper—*Parnara guttata, Melanitis leda ismene*
    rice stem borer/striped stem borer—*Chilo suppressalis, Chilo polychrusus, Chilo partellus, Chilo plejadellus*
    rice stalk borer—*Chilotraea polychrysa*
    pink rice borer—*Sesamia inferens*
    yellow rice borer—*Tryporyza (=Scirpophaga) incertulas*
    white rice borer—*Tryporyza innotata*
    rice leafroller/leaf folder—*Cnaphalocrocis medinalis, Marasmia patnalis, M. exigua*
    rice ear-cutting caterpillar/armyworm—*Pseudaletia separata*
    green caterpillar—*Xanthodes transversa*
    green rice caterpillar—*Narnaga aenescens*
    green horned caterpillars—*Melanitis leda ismene, Mycalesis sp*
    fall army worm—*Spodoptera frugiperda*
    cutworm—*Mythimna separata*
    rice case worm—*Nymphula depunctalis*
    black hairy caterpillar, *Amata sp.*
    hairy caterpillar—*Mocis frugalis*
    yellow caterpillar, *Psalis pennatula*
    rice semi-brown looper, *Mocis frugalis*
    rice semi-looper, *Chrysodeixis chalcites*
    grass webworm—*Herpetogramma licarsisalis*
    sugarcane borer—*Diatraea saccharalis*
    corn stalk borer—*Elasmopalpus lignosellus*
    striped grass looper—*Mocis latipes*
    european corn borer—*Ostrinia nublalis*
    Mexican rice borer—*Eoreuma loftini*
Coleoptera:
    water weevil—*Lissorhopterus oryzophilus*
    rice plant weevil—*Echinocnemus squamous*
    rice weevil—*Oryzophagus oryzae*
    rice hispa—*Diclodispa armigera*
    rice leaf beetle—*Oulema oryzae*
    rice blackbug—*Scotinophora vermidulate, S. vermidulate, S. lurida, S. latiuscula*
    rice flea beetle—*Chaetocnima basalis*
    grubs—*Leucopholis irrorata, Leucopholis irrorata, Phyllophaga sp, Heteronychus sp*
    scarab beetle (bicho torito)—*Diloboderus abderus*
    billbugs—*Sphenophorus spp*
    grape *colaspis*—*Colaspis brunnea, C. louisianae*
    rice pollen beetle, *Chilolaba acuta*
Diptera:
    stem maggot—*Chlorops oryzae*
    leafminer—*Agromyza oryzae*
    rice whorl maggot/rice stem maggot—*Hydrellia sasakii*
    rice whorl maggot/small rice leafminer—*Hydrellia griseola*
    rice gall midge—*Orseolia (=Pachydiplosis) oryzae*
    rice shoot fly—*Atherigona oryzae*
    rice seed midge—*Chironomus cavazzai, Chironomus* spp, *Cricotopus* spp
Thysanoptera:
    rice *thrips*—*Chloethrips oryzae, Stenochaetothrips biformis, Perrisothrips sp., Hoplothrips sp.,*
Orthoptera:
    rice grasshoppers, *Hieroglyphus banian, Hieroglyphus nigrorepletus, Catantops pinguis, Attractomorpha burri, A. crenulate, A. psittacina psittacina, A. Bedeli, Oxya adenttata, Oxya ebneri, Oxya hyla intricata, Acrida turricata*
    locusts—*Locusta migratoria manilensis*
    mole cricket, *Grylotalpa africana*
    field cricket: *Gryllus bimaculatus, Teleogryllus occipitalis, Euscyrtus concinus*
    katydid—*Conocephalus longipennis*
Isoptera:
    termites—*Macrotermes gilvus, Syntermes molestans*
Hymenoptera:
    ants—*Solenopsis geminata*
    rice white tip nematode—*Aphelenchoides besseyi*
Acari:
    rice panicle mite—*Steotarsonemus pinki*
Crustacea:
    tadpole shrimp—*Triops longicaudatus. T. cancriformis*
    rice crayfish—*Procambarus clarkii, Orconectes virilis.*

In addition, rice is affected by a range of bugs including *Leptocorisa chinensis, Lagynotomus elongates, Nerzara viridula, Eysacoris parvus, Leptocorisa oratorius, Oebalus pugnax, Cletus trigonus*, as well as a variety of mites, caterpillars, beetles, rootworms and maggots.

In one embodiment, the rice pest invertebrate is a biting/chewing insect.

In one embodiment, the rice pest invertebrate is a piercing/sucking insect.

In one embodiment, the rice pest invertebrate is a rasping insect.

In one embodiment, the rice pest invertebrate is a siphoning insect.

In one embodiment, the rice pest invertebrate is a sponging insect.

In one embodiment, the rice pest invertebrate is selected from brown planthopper (*Nilaparvata lugens*), small brown planthopper (*Laodelphax striatellus*), white-backed planthopper (*Sogatella furcifera*), rice stem borer/striped stem borer (*Chilo suppressalis*), yellow rice borer (*Tryporyza (=Scirpophaga) incertulas*), rice leafroller/leaf folder (*Cnaphalocrocis medinalis*), water weevil (*Lissorhopterus oryzophilus*).

In one embodiment, the rice pest invertebrate is from the order Hemiptera or Lepidoptera.

In one embodiment, the rice pest invertebrate is from the order Hemiptera. In a further embodiment, the rice pest invertebrate is a hopper, preferably selected from brown planthopper (*Nilaparvata lugens*), small brown planthopper (*Laodelphax striatellus*), white-backed planthopper (*Sogatella furcifera*), green leafhopper (*Nephotettix virescens*). In a further embodiment, the rice pest invertebrate is selected from brown planthopper (*Nilaparvata lugens*) and green leafhopper (*Nephotettix virescens*), preferably brown planthopper (*Nilaparvata lugens*).

In one embodiment, the rice pest invertebrate is the brown planthopper (*Nilaparvata lugens*).

In one embodiment, the rice pest invertebrate is the green leafhopper (*Nephotettix virescens*).

In a further embodiment, the rice pest invertebrate is a stink bug, preferably selected from rice stink bugs (*Nezara viridula, Pygomenida varipennis, Eysarcoris, Tibraca limbatriventris, Eysarcoris ventralis*) or small stink bug (*Oebalus poecilus, O. pugnax*).

In one embodiment, the rice pest invertebrate is from the order Lepidoptera. In a further embodiment, the rice pest invertebrate is a borer, preferably stem borer, preferably rice stem borer (*Chilo suppressalis*) or yellow rice borer (*Tryporyza* (=*Scirpophaga*) *incertulas*).

In a further embodiment, the rice pest invertebrate is the rice leafroller/leaf folder (*Cnaphalocrocis medinalis, Marasmia patnalis, M. exigua*).

In one embodiment, the rice pest invertebrate is from the order Coleoptera. In a further embodiment, the rice pest invertebrate is water weevil (*Lissorhopterus oryzophilus*). In a further embodiment, the rice pest invertebrate is rice weevil (*Oryzophagus oryzae*).

In one embodiment, the rice pest invertebrate is from the family of termites (order Isoptera).

Animal Health

The compounds and mixtures of the present invention are suitable for use in treating or protecting animals against infestation or infection by parasites. Therefore, the present invention also relates to the use of a compound of the present invention for the manufacture of a medicament for the treatment or protection of animals against infestation or infection by parasites. Furthermore, the present invention relates to a method of treating or protecting animals against infestation and infection by parasites, which comprises orally, topically or parenterally administering or applying to the animals a parasiticidally effective amount of a compound of the present invention.

The present invention also relates to the non-therapeutic use of compounds and mixtures of the present invention for treating or protecting animals against infestation and infection by parasites. Moreover, the present invention relates to a non-therapeutic method of treating or protecting animals against infestation and infection by parasites, which comprises applying to a locus a parasiticidally effective amount of a compound of the present invention.

The compounds and mixtures of the present invention are further suitable for use in combating or controlling parasites in and on animals. Furthermore, the present invention relates to a method of combating or controlling parasites in and on animals, which comprises contacting the parasites with a parasitically effective amount of a compound of the present invention.

The present invention also relates to the non-therapeutic use of compounds and mixtures of the present invention for controlling or combating parasites. Moreover, the present invention relates to a non-therapeutic method of combating or controlling parasites, which comprises applying to a locus a parasiticidally effective amount of a compound of the present invention.

The compounds and mixtures of the present invention can be effective through both contact (via soil, glass, wall, bed net, carpet, blankets or animal parts) and ingestion (e.g. baits). Furthermore, the compounds and mixtures of the present invention can be applied to any and all developmental stages.

The compounds and mixtures of the present invention can be applied as such or in form of compositions comprising the compounds and mixtures of the present invention.

The compounds and mixtures of the present invention can also be applied together with a mixing partner, which acts against pathogenic parasites, e.g. with synthetic coccidiosis compounds, polyetherantibiotics such as Amprolium, Robenidin, Toltrazuril, Monensin, Salinomycin, Madurami-cin, Lasalocid, Narasin or Semduramicin, or with other mixing partners as defined above, or in form of compositions comprising said mixtures.

The compounds and mixtures of the present invention and compositions comprising them can be applied orally, par-enterally or topically, e.g. dermally. The compounds and mixtures of the present invention can be systemically or non-systemically effective.

The application can be carried out prophylactically, thera-peutically or non-therapeutically. Furthermore, the applica-tion can be carried out preventively to places at which occurrence of the parasites is expected.

As used herein, the term "contacting" includes both direct contact (applying the com-pounds/compositions directly on the parasite, including the application directly on the animal or excluding the application directly on the animal, e.g. at it's locus for the latter) and indirect contact (applying the compounds/compositions to the locus of the parasite). The contact of the parasite through application to its locus is an example of a non-therapeutic use of the compounds and mixtures of the present invention.

The term "locus" means the habitat, food supply, breeding ground, area, material or environment in which a parasite is growing or may grow outside of the animal.

As used herein, the term "parasites" includes endo- and ectoparasites. In some embodiments of the present inven-tion, endoparasites can be preferred. In other embodiments, ectoparasites can be preferred. Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds and mixtures of the present invention are especially useful for combating parasites of the following orders and species, respectively:

fleas (Siphonaptera), e.g. *Ctenocephalides felis, Cteno-cephalides canis, Xenopsylla cheopis, Pulex irritans, Tunga penetrans*, and *Nosopsyllus fasciatus*; cockroaches (*Blat-taria*—Blattodea), e.g. *Blattella germanica, Blattella asa-hinae, Periplaneta americana, Periplaneta japonica, Peri-planeta brunnea, Periplaneta fuligginosa, Periplaneta australasiae*, and *Blatta orientalis*; flies, mosquitoes (*Dip-tera*), e.g. *Aedes aegypti, Aedes albopictus, Aedes vexans, Anastrepha ludens, Anopheles maculipennis, Anopheles cru-cians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellarna, Chrysops discalis, Chrysops silacea, Chrysops atlanticus, Cochliomyia hominivorax, Cordylobia anthropophaga, Culicoides furens, Culex pipiens, Culex nigrpalpus, Culex quinquefasciatus, Culex tarsalis, Culiseta inornata, Culiseta melanura, Dermatobia hominis, Fannia canicularls, Gas-terophilus intestinalis, Glossina morsitans, Glossina palpa-lis, Glossina fuscipes, Glossina tachinoides, Haematobia irritans, Haplodiplosis equestris, Hippelates* spp., *Hypo-derma lineata, Leptoconops torrens, Lucilia caprina, Lucilia cuprina, Lucilia sericata, Lycoria pectoralis, Man-sonia* spp., *Musca domestica, Muscina stabulans, Oestrus ovis, Phlebotomus argentipes, Psorophora columbiae, Pso-rophora discolor, Prosimulium mixtum, Sarcophaga haem-orrhoidalis, Sarcophaga* sp., *Simulium vittatum, Stomoxys calcitrans, Tabanus bovinus, Tabanus atratus, Tabanus line-*

*ola*, and *Tabanus similis*; lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*; ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*; Actinedida (Prostigmata) und Acaridida (Astigmata), e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp; Bugs (Heteropterida): *Cimex lectularius, Cimex hemipterus, Reduvius senilis, Triatoma* spp., *Rhodnius* ssp., *Panstrongylus* ssp., and *Arilus critatus*; Anoplurida, e.g. *Haematopinus* spp., *Linognathus* spp., *Pediculus* spp., *Phtirus* spp., and *Solenopotes* spp.; Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp.; Roundworms Nematoda: Wipeworms and *Trichinosis* (Trichosyringida), e.g. Trichinellidae (*Trichinella* spp.), (Trichuridae) *Trichuris* spp., *Capillaria* spp.; Rhabditida, e.g. *Rhabditis* spp., *Strongyloides* spp., *Helicephalobus* spp.; Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp., *Aleurostrongylus abstrusus*, and *Dioctophyma renale*; Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*; Camallanida, e.g. *Dracunculus medinensis* (guinea worm); Spirurida, e.g. *Thelazia* spp., *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp.; Thorny headed worms (Acanthocephala), e.g. *Acanthocephalus* spp., *Macracanthorhynchus hirudinaceus* and *Oncicola* spp.; Planarians (Plathelminthes): Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp.; Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

As used herein, the term "animal" includes warm-blooded animals (including humans) and fish. Preferred are mammals, such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels. Particularly preferred are domestic animals, such as dogs or cats.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally, it is favorable to apply the compounds and mixtures of the present invention in total amounts of 0.5 mg/kg to 100 mg/kg per day, preferably 1 mg/kg to 50 mg/kg per day.

For oral administration to warm-blooded animals, the compounds and mixtures according to the invention may be formulated as animal feeds, animal feed premixes, animal feed concentrates, pills, solutions, pastes, suspensions, drenches, gels, tablets, boluses and capsules. In addition, the compounds and mixtures according to the invention may be administered to the animals in their drinking water. For oral administration, the dosage form chosen should provide the animal with 0.01 mg/kg to 100 mg/kg of animal body weight per day of the component I compound, preferably with 0.5 mg/kg to 100 mg/kg of animal body weight per day.

Alternatively, the compounds (component I) and mixtures according to the invention may be administered to animals parenterally, for example, by intraruminal, intramuscular, intravenous or subcutaneous injection. The compounds (component I) and mixtures according to the invention may be dispersed or dissolved in a physiologically acceptable carrier for subcutaneous injection. Alternatively, the compounds (component I) and mixtures according to the invention may be formulated into an implant for subcutaneous administration. In addition the component I compound may be transdermally administered to animals. For parenteral administration, the dosage form chosen should provide the animal with 0.01 mg/kg to 100 mg/kg of animal body weight per day of the component I compound.

The compounds (component I) and mixtures according to the invention may also be applied topically to the animals in the form of dips, dusts, powders, collars, medallions, sprays, sham-poos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the component I. In addition, the compounds (component I) and mixtures according to the invention may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active component I or II or mixture is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further auxiliaries such as acids, bases, buffer salts, preservatives, and solubilizers. Suitable auxiliaries for injection solutions are known in the art. The solutions are filtered and filled sterile.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Gels are applied to or spread on the skin or introduced into body cavities. Gels are prepared by treating solutions which have been prepared as described in the case of the injection solutions with sufficient thickener that a clear material having an ointment-like consistency results. Suitable thickeners are known in the art.

Pour-on formulations are poured or sprayed onto limited areas of the skin, the active compound I or mixture penetrating the skin and acting systemically. Pour-on formulations are prepared by dissolving, suspending or emulsifying the active component I or II or mixture in suitable skin-compatible solvents or solvent mixtures. If appropriate, other auxiliaries such as colorants, bioabsorption-promoting substances, antioxidants, light stabilizers, adhesives are added. Suitable such auxiliaries are known in the art.

Emulsions can be administered orally, dermally or as injections. Emulsions are either of the water-in-oil type or of the oil-in-water type. They are prepared by dissolving the active component I or mixture either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances. Suitable hydrophobic phases (oils), suitable hydrophilic phases, suitable emulsifiers, and suitable further auxiliaries for emulsions are known in the art.

Suspensions can be administered orally or topically/dermally. They are prepared by suspending the active component I or II or mixture in a suspending agent, if appropriate with addition of other auxiliaries such as wetting agents, colorants, bioabsorption-promoting substances, preservatives, antioxidants, light stabilizers. Suitable suspending agents, and suitable other auxiliaries for suspensions including wetting agents are known in the art.

Semi-solid preparations can be administered orally or topically/dermally. They differ from the suspensions and emulsions described above only by their higher viscosity.

For the production of solid preparations, the active component I or II or mixture is mixed with suitable excipients, if appropriate with addition of auxiliaries, and brought into the desired form. Suitable auxiliaries for this purpose are known in the art.

The compositions which can be used in the invention can comprise generally from about 0.001 to 95% of the component I of the present invention.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the component I against endoparasites in concentrations of 10 ppm to 2 percent by weight, preferably of 0.05 to 0.9 percent by weight, very particularly preferably of 0.005 to 0.25 percent by weight.

Topical application may be conducted with compound-containing shaped articles such as collars, medallions, ear tags, bands for fixing at body parts, and adhesive strips and foils.

Generally it is favorable to apply solid formulations which release compounds (component I) and mixtures of the present invention in total amounts of 10 mg/kg to 300 mg/kg, preferably 20 mg/kg to 200 mg/kg, most preferably 25 mg/kg to 160 mg/kg body weight of the treated animal in the course of three weeks.

EXAMPLES

Synthesis Example: 3-(2-chlorothiazol-5-yl)-8-methyl-7-oxo-6-phenyl-2,3-dihydrothiazolo[3,2-a]pyrimidin-8-ium-5-olate (Corresponding to Compound I-1)

Step 1: 2-chloro-N-methoxy-N-methyl-acetamide

N-Methoxymethanamine hydrochloride (345 g) and water (1.5 L) were cooled to 0° C. To this reaction mixture, $K_2CO_3$ (1466 g) was added in lots, then methyl tert-butyl ether (1000 mL) was added at 0° C. The reaction mixture was cooled to −5° C. Chloroacetylchloride (400 g) in methyl tert-butyl ether (500 ml) was added drop wise at −5° C. to 0° C. and stirred for 2 hours at 0° C. The reaction mixture was allowed to come to 20-25° C. From the organic layer, the desired product was obtained as white solid (438 g, 90% yield; 98.45% HPLC purity).

Step 2: 2-chloro-1-(2-chlorothiazol-5-yl) ethanone 2-chlorothiazole (187 ml) in 750 ml tetrahydrofurane under nitrogen atmosphere were cooled to −20° C. Isopropylmagnesium chloride×LiCl (1684 ml, 1.3 molar in tetrahydrofurane) was added drop wise and stirred at −20° C. for 60 minutes. A solution of 2-chloro-N-methoxy-N-methyl-acetamide (250 g) in tetrahydrofurane was added drop wise at −20° C. to −25° C. The reaction mixture was stirred at −20° C. for 90 minutes. Saturated aqueous ammonium chloride solution was added at −20° C., then the reaction mixture was brought to 20-25° C. The two phases were separated and the aqueous phase was extracted with ethyl acetate. From the combined organic layers, the desired crude product was obtained as dark brown colored oil, which was treated with activated charcoal and silica in methyl tert-butyl ether to get the crude product as pale brown colored oil (335 g) for direct use in the next step.

Step 3: N-[2-chloro-1-(2-chlorothiazol-5-yl) ethylidene]-2-methyl-propane-2-sulfinamide To crude 2-chloro-1-(2-chlorothiazol-5-yl) ethanone (335 g) in tetrahydrofurane at 20-25° C. under nitrogen atmosphere, tert-butyl sulfinamide (206 g) and Ti(OEt)$_4$ (396 ml) are added. The mixture was heated to 50° C. and stirred for 2 hours, then cooled to 20-25° C. and diluted with ethyl acetate. After adding water, the mixture was stirred for 30 minutes, then filtered. The organic phase was evaporated to obtain the desired crude product as brown colored oil. After treatment with activated charcoal and silica in methyl tert-butyl ether, the crude product was obtained as pale brown colored oil (365 g) for direct use in the next step.

Step 4: N-[2-chloro-1-(2-chlorothiazol-5-yl) ethyl]-2-methyl-propane-2-sulfinamide To N-[2-chloro-1-(2-chlorothiazol-5-yl) ethylidene]-2-methyl-propane-2-sulfinamide (365 g) in tetrahydrofurane and methanole at −5° C., NaBH$_4$ (23 g) was added lot wise and stirred for 30 minutes. Saturated aqueous ammonium chloride solution was added at 0° C. After extracting with ethyl acetate, the organic layer yielded the desired crude product as brown colored oil (310 g).

Step 5: 2-chloro-1-(2-chlorothiazol-5-yl) ethanamine hydrochloride

N-[2-chloro-1-(2-chlorothiazol-5-yl) ethyl]-2-methyl-propane-2-sulfinamide was stirred with HCl in methanole (1 molar, 620 mL) at 20-25° C. for 12 hours. Removal of methanole under vacuum yielded a pale yellow sticky solid (244 g), which was washed with methyl tert-butyl ether and subsequently with ethyl acetate to get a pale yellow color solid (78 g, 26% yield over steps 2 to 5, >98% purity).

Step 6: 4-(2-chlorothiazol-5-yl)-N-methyl-thiazolidin-2-imine 2-chloro-1-(2-chlorothiazol-5-yl) ethanamine hydrochloride (285 g) in methyl tert-butyl ether and 2 molar aqueous NaOH solution (1060 mL) were stirred for 20 minutes at 23° C. The organic layer yielded the free amine as pale brown colored oil (230 g).

The amine (230 g) in ethanole was reacted with triethylamine NEt3 (351 ml) and Me-NCS (143.2 g) at 22 to 25° C. for 18 hours. The reaction mass was concentrated to obtain a brown colored residue, to which aqueous NaOH solution (114 g in 920 mL of water) was added. The resulting mixture was heated to 100° C. for 2 hours, then cooled to 20-25° C. and diluted with water. After extraction with ethyl acetate, the organic layer yielded crude 4-(2-chlorothiazol-5-yl)-N-methyl-thiazolidin-2-imine as brown colored solid (256 g), which was stirred with 20% ethyl acetate in heptane (300 mL) for 30 minutes. After filtering, the product was obtained as a brown colored solid (245 g, 85% yield).

Step 7: 3-(2-chlorothiazol-5-yl)-8-methyl-7-oxo-6-phenyl-2,3-dihydrothiazolo[3,2-a] pyrimidin-8-ium-5-olate (I-1)

4-(2-chlorothiazol-5-yl)-N-methyl-thiazolidin-2-imine (110 g) in toluene was stirred at 110 to 115° C. After adding bis(4-chlorophenyl) 2-phenylpropanedioate (226 g), the reaction mixture was stirred at this temperature for 2 hours, then cooled to 40 to 45° C. After removal of toluene under vacuum, a brown solid was obtained, which was triturated with methyl tert-butyl ether to obtain a yellow color solid.

Stirring in methyl tert-butyl ether (1 L) at 22 to 25° C. for 14 hours yielded a pale yellow solid (160 g). Further purification by dissolving in dichloromethane and precipitating with methyl tertbutyl ether yielded the desired product as fine pale yellow colored powder (129 g, 80% yield).

*: HPLC Method: Retention time in minutes; mass charge ratio m/z

HPLC Method A:
MSD4/5: Shimadzu Nexera UHPLC+Shimadzu LCMS 20-20, ESI
Column: Phenomenex Kinetex 1.7 μm XB-C18 100 A, 50×2.1 mm
Mobile Phase: A: water+0.1% trifluoroacetic acid; B: acetonitrile, Temperature: 60° C.
Gradient: 5% B to 100% B in 1.50 min; 100% B 0.25 min
Flow: 0.8 ml/min to 1.0 ml/min in 1.51 min
MS method: ESI positive, Mass range (m/z): 100-700
HPLC Method B:
MSD4/5: Shimadzu Nexera UHPLC+Shimadzu LCMS 20-20, ESI
Column: Agilent Eclipse Plus C18, 50 mm×4.6 mm×3
Mobile phase: A=10 mM ammonium formate (0.1% Formic Acid) B=acetonitrile (0.1% Formic Acid), Flow=1.2 ml/min. Column oven: 30 C
Gradient:=10% B to 100% B—1.5 min, hold for 1 min, 2.51 min—10% B; Run Time=3.50 min
HPLC Method C:
same as Method A, but MS method: ESI positive, Mass range (m/z): 100-1400

Example—Separation of the Enantiomers

R-3-(2-chlorothiazol-5-yl)-8-methyl-7-oxo-6-phenyl-2,3-dihydrothiazolo[3,2-a] pyrimidin-8-ium-5-olate and S-3-(2-chlorothiazol-5-yl)-8-methyl-7-oxo-6-phenyl-2,3-dihydrothiazolo[3,2-a] pyrimidin-8-ium-5-olate The enantiomers of 3-(2-chlorothiazol-5-yl)-8-methyl-7-oxo-6-phenyl-2,3-dihydrothiazolo[3,2-a]pyrimidin-8-ium-5-olate from example 1 can be separated by preparative chiral supercritical fluid chromatography. 126 g of rac-3-(2-chlorothiazol-5-yl)-8-methyl-7-oxo-6-phenyl-2,3-dihydrothiazolo[3,2-a] pyrimidin-8-ium-5-olate were separated. This yielded 53.4 g of R-3-(2-chlorothiazol-5-yl)-8-methyl-7-oxo-6-phenyl-2,3-dihydrothiazolo[3,2-a] pyrimidin-8-ium-5-olate at a retention time of 1.94 min and 57.7 g of S-3-(2-chlorothiazol-5-yl)-8-methyl-7-oxo-6-phenyl-2,3-dihydrothiazolo[3,2-a] pyrimidin-8-ium-5-olate at a retention time of 1.41 min. These retention times refer to the analytical method cited below. The configuration of the chiral centre was determined by X-ray analysis.

Analytical Separation Method:
Instrument: Thar analytical SFC
Column: Chiralpak AS-H, 150×4.6 mm i.d., 5 u
Mobile phase: A for CO$_2$ and B for MeOH, Gradient: B %=40%
Flow rate: 4.0 mL/min, Back pressure: 100 bar, Column temperature: 35° C.
Wavelength: 220 nm
Preparative Separation Method:
Instrument: Thar 80 preparative SFC
Column: Chiralcel OJ-H, 250×30 mm I.D. 5 u
Mobile phase: A for CO$_2$ and B for CH$_3$CN, Gradient: B %=50%
Flow rate: 80 g/min, Back pressure: 100 bar, Column temperature: 40° C.
Wavelength: 220 nm
Cycletime: 6.5 min Sample preparation: Racemic material was dissolved in mixed solution of MeOH—$CH_3CN$-DCM (1:1:0.5) to 20 mg/mL and filtrated through membrane with pore sized 0.45 um.

Injection: 4 mL per injection.

After separation, the fractions were dried off via rotary evaporator at bath temperature 35° C. to get the two enantiomers.

Preparation of Compound of Formula I with Enantiomeric Excess:

The characterization can be done by coupled High Performance Liquid Chromatography/mass spectrometry (HPLC/MS), Gas chromatography (GC), by NMR or by their melting points.

HPLC method: Agilent Eclipse Plus C18, 150 mm×4.6 mm ID×5 um

Gradient A=0.1% TFA in Water, B=0.1% TFA in Acetonitrile.

Flow=1.4 ml/min., column oven temperature=30 C

Gradient program=10% B-100% B—5 min, hold for 2 min, 3 min—10% B.

Run Time=10 min

LCMS method 1: C18 Column (50 mm×3.0 mm×3μ)

Gradient A=10 Mm Ammonium formate in water, B=0.1% Formic acid in acetonitrile

Flow=1.2 ml/min., column oven temperature=40° C.

Gradient program=10% B to 100% B in 1.5 min., hold for 1 min 100% B, 1 min—10% B Run time: 3.75 min Chiral HPLC method 1: ChiralPak IA column, 150 mm×4.6 mm×5μ

Mobile phase A=heptane, B=isopropanol,

Flow=1.0 ml/min, column oven temperature=40° C.

Gradient program=10% B Isocratic; run time: 20 min

Chiral HPLC method 3: ChiralPak IA column, 150 mm×4.6 mm×5μ

Mobile phase A=heptane, B=isopropanol,

Flow=1.0 ml/min, column oven temperature=40° C.

Gradient program=40% B Isocratic; run time: 20 min $^1$H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplet, q=quartet, t=triplet, d=doublet and s=singlet.

Abbreviations used are: h for hour(s), min for minute(s), rt for retention time and ambient temperature for 20-25° C.

Example 1: Preparation of Compound of Formula I-1 with Enantiomeric Excess of Compound I-R-1 ((3R)-3-(2-chlorothiazol-5-yl)-8-methyl-7-oxo-6-phenyl-2,3-dihydrothiazolo[3,2-a]pyrimidin-4-ium-5-olate)

Step-1: Preparation of 2-chloro-N-methoxy-N-methyl-acetamide

A 3 L four necked flask equipped with Teflon-blade stirrer, reflux condenser and thermo-pocket was charged with N-methoxymethanamine hydrochloride (345 g), water (1.6 litre) and the resulting reaction mixture was cooled to 0 to −5° C. Then potassium carbonate (1466 g) was added in lots to the above reaction mixture followed by the addition of methyl tert-butyl ether (1.4 litre). The chloroacetyl chloride (400 g) was dissolved in tert-butyl methyl ether (0.2 litre) and added dropwise in to the above kept reaction mixture at −5° C. to 0° C. and the reaction mixture was stirred for 2 h at 0° C. The reaction mixture was allowed to come to ambient temperature and two phases were separated. The organic layer was dried over sodium sulfate, filtered and evaporated to provide 2-chloro-N-methoxy-N-methyl-acetamide as white solid (440 g, 90% yield and 98.0% area purity by HPLC).

Step-2: Preparation of 2-chloro-1-(2-chlorothiazol-5-yl)ethenone

A 5 L, four necked flask equipped with Teflon-blade stirrer, reflux condenser and thermo-pocket was charged with 2-chlorothiazole (250 g), THF (0.75 L) and the resulting reaction mixture was cooled to 0 to −5° C. Then isopropylmagnesium chloride lithium chloride (1.929 L, 1.3 M solution in THF) was added over 0.5 h into the above kept reaction mixture at 0 to −5° C. The reaction mixture was then heated to 40° C. and the reaction was continued at 40° C. for 2 h. The formation of chloro-(2-chlorothiazol-5-yl) magnesium species was confirmed by quenching the small aliquot of the reaction mixture with iodine and monitoring the formation of 2-chloro-5-iodo-thiazole by GC analysis (96% conversion was observed by GC analysis). The reaction mixture was cooled to 0 to −5° C. and the solution of 2-chloro-N-methoxy-N-methyl-acetamide (343 g) in THF (0.25 L) was added dropwise. The reaction was continued at −5 to 0° C. for 1 h and the reaction progress was monitored by HPLC. The reaction mixture was quenched with 1.5 N aq. HCl solution (1 L) at −5 to 0° C. and then warmed to ambient temperature. The two phases were separated and the aqueous phase extracted with methyl tert-butyl ether (2×300 mL). The combined organic layers were dried over sodium sulfate, filtered and evaporated to obtain crude residue. The crude product was dissolved in methyl tert-butyl ether (0.7 L) at ambient temperature and activated charcoal (4 g) and silica (80 g, 60-120 mesh) were added. The slurry was stirred for 0.5 h, filtered through Buchner funnel and washed with methyl tert-butyl ether (0.3 L). The filtrate was evaporated to obtain 2-chloro-1-(2-chlorothiazol-5-yl)ethanone as pale brown colored oil (409 g, 46% area purity by HPLC)

Step-3: Preparation of [2-(2-chlorothiazol-5-yl)-2-oxo-ethyl] acetate

A 0.25 L, three necked flask equipped with teflon-blade stirrer, reflux condenser and thermo-pocket was charged with 2-chloro-1-(2-chlorothiazol-5-yl)ethanone (15 g, 46 area % HPLC purity) and dimethylformamide (45 mL) at ambient temperature. Then sodium acetate (12.55 g) was added in portions and reaction was continued at ambient temperature for 4 h. The reaction progress was monitored by HPLC (>95% conversion by HPLC). The reaction was quenched with water (50 mL) and extracted with methyl tert-butyl ether (3×100 mL). The two phases were separated and the combined organic phases were dried over sodium sulfate, filtered and evaporated to obtain crude residue (17 g). The crude product was purified by silica gel column chromatography to obtain [2-(2-chlorothiazol-5-yl)-2-oxo-ethyl]acetate as yellow colored solid (7.5 g).

Step-4: Preparation of 1-(2-chlorothiazol-5-yl)-2-hydroxy-ethanone

A 250 mL, three necked flask equipped with magnetic stirrer, reflux condenser and thermo-pocket was charged with [2-(2-chlorothiazol-5-yl)-2-oxo-ethyl]acetate (7.5 g) and 1 N HCl in MeOH (50 mL). The resulting solution was stirred for 5 h and reaction progress was monitored by TLC. The methanol from reaction mixture was distilled under vacuum and crude residue obtained was purified by column chromatography to obtain 1-(2-chlorothiazol-5-yl)-2-hydroxy-ethanone as pale yellow solid (2.8 g, 84% area purity by HPLC).

Step-5: Preparation of 4-(2-chlorothiazol-5-yl)-5H-oxathiazole 2,2-dioxide

A 100 mL, three neck flasks equipped with magnetic stirrer, reflux condenser and thermo-pocket was charged with 1-(2-chlorothiazol-5-yl)-2-hydroxy-ethanone (1 g), toluene (20 mL), chlorosulfonamide (0.975 g) and p-toluenesulfonic acid (0.214 g). The resulting solution was heated to 100° C. and stirred for 1 h. The reaction progress was monitored by HPLC (>95% conversion). The reaction mixture was quenched with water and extracted with MTBE (15 mL×2). The two phases were separated, organic phase was evaporated and purified by column chromatography 4-(2-chlorothiazol-5-yl)-5H-oxathiazole 2,2-dioxide (0.42 g).

Step-6: Preparation of (4R)-4-(2-chlorothiazol-5-yl) oxathiazolidine 2,2-dioxide a) Preparation of Rhodium Catalyst—RhCl[(R,R)-TsDPEN]Cp*:

A 250 mL, three necked flask equipped with teflon-blade stirrer, nitrogen inlet and thermo-pocket was charged with [RhCl$_2$Cp*]$_2$ (2.0 g), (1R,2R)—N-p-toluenesulfonyl-1,2-diphenylethylenediamine (2.38 g), dichloromethane (68 mL) and triethylamine (1.72 ml) under nitrogen atmosphere. The resulting slurry was stirred for 0.5 h at 22-27° C. and distilled water was added (40 mL). The two phases were separated and the organic phase was washed with water (40 mL). The organic phase was dried over sodium sulfate, filtered and evaporated to get brown coloured solid residue. The brown residue was triturated with n-heptane (20 mL), filtered and dried under nitrogen atmosphere to get obtain RhCl [(R,R)-TsDPEN]Cp* as red coloured solid (3.4 g).

b) Preparation of HCOOH-NEt$_3$ Mixture:

In a 2 liter, 3 neck round bottom flask Formic acid (275 mL, >=99% w/w) was added and cooled to 0° C. To this, triethylamine 250 mL, >=99% w/w) was added slowly at 0° C. and used immediately in reaction.

c) Preparation of (4R)-4-(2-chlorothiazol-5-yl)oxathiazolidine 2,2-dioxide:

A 100 ml, two necked flask equipped with magnetic stirrer, condenser and thermo-pocket was charged with 4-(2-chlorothiazol-5-yl)-5H-oxathiazole 2,2-dioxide (0.5 g) and dimethylformamide (15 mL, 30V) was degassed with nitrogen for 10 min. Then RhCl[(R,R)-TsDPEN]Cp* (27 mg) was added followed by dropwise addition of HCOOH-NEt$_3$ (2.5 mL, in a ratio of 5:2). The resulting mixture was stirred for 2 h. The HPLC showed >97% conversion. The reaction mixture was quenched with water (15 ml) and extracted with methyl tert-butyl ether (3×50 mL). The combined organic phase was evaporated to obtain (4R)-4-(2-chlorothiazol-5-yl)oxathiazolidine 2,2-dioxide (500 mg; 90 area % HPLC purity (rt=3.645 min.), >99% ee by chiral HPLC method 1).

Step-7: Preparation of (4R)-4-(2-chlorothiazol-5-yl)-N-methyl-thiazolidin-2-imine A 100 mL, three necked flask equipped with magnetic stirrer, reflux condenser and thermo-pocket was charged with (4R)-4-(2-chlorothiazol-5-yl)oxathiazolidine 2,2-dioxide (0.5 g, with 99% ee), ethanol (2 ml), methyl isothiocyanate (0.228 g) and triethylamine (0.56 ml) at ambient temperature. The resulting mixture was stirred for 14 h at 22-27° C. Then organic volatiles were re-moved under vacuum and sodium hydroxide (0.2 g) and water (2 mL) were added into the reaction flask. The reaction mixture was heated to 100° C. and stirred for 2 h. The reaction was diluted with water (2 mL) and extracted with methyl tert-butyl ether (2×50 mL). The organic phases were dried over sodium sulfate and evaporated under vacuum to provide (4R)-4-(2-chlorothiazol-5-yl)-N-methyl-thiazolidin-2-imine as brown oil [0.34 g, m/z=234 amu (M+H$^+$)].

Step-8: Preparation of (3R)-3-(2-chlorothiazol-5-yl)-8-methyl-7-oxo-6-phenyl-2,3-dihydrothiazolo[3,2-a]pyrimidin-4-ium-5-olate A 50 mL, three necked flask equipped with magnetic stirrer, reflux condenser and thermo-pocket was charged with (E,4R)-4-(2-chlorothiazol-5-yl)-N-methyl-thiazolidin-2-imine (0.34 g), toluene (2 mL) and heated to 110° C. under nitrogen atmosphere. Then bis(2,4,6-trichlorophenyl) 2-phenylpropanedioate (0.857 g) was added in lots into the reaction mass kept at 110° C. After stirring at 110° C. for 2 h, HPLC showed >99% conversion. The reaction was cooled below 50° C. and the precipitated pale yellow colored solid was filtered through sintered funnel and then solid residue was washed with methyl tert-butyl ether (4 mL) and dried under vacuum to provide (3R)-3-(2-chlorothiazol-5-yl)-8-methyl-7-oxo-6-phenyl-2,3-dihydrothiazolo[3,2-a]pyrimidin-4-ium-5-olate (110 mg, m/z=378 amu (M+H$^+$) & 95.2% enantiomeric excess by chiral HPLC method 3). $^1$H NMR (300 MHz, DMSO-d6): 3.42 (s, 3H), 3.94 (d, J=12 Hz, 1H), 4.25-4.32 (m, 1H), 6.48 (d, J=8.1 Hz, 1H), 7.06-7.11 (m, 1H), 7.21-7.26 (m, 2H), 7.6 (d, J=7.5 Hz, 1H), 7.96 (s, 1H).

Biological Examples

If not otherwise specified, the test solutions are prepared as follows:

The active compound is dissolved at the desired concentration in a mixture of 1:1 (vol:vol) distilled water: acetone. The test solution is prepared at the day of use.

Test compound I-R-1 used in below biological examples is in 95% enantiomeric excess unless otherwise specified.

Test compound I-S-1 used in below biological examples is in 95% enantiomeric excess unless otherwise specified.

B.1 Rice Green Leafhopper (*Nephotettix virescens*):

Rice seedlings are cleaned and washed 24 hours before spraying. The active compounds are formulated in 50:50 acetone:water (vol:vol), and 0.1% vol/vol surfactant (EL 620) is added. Potted rice seedlings are sprayed with 5 ml test solution, air dried, placed in cages and inoculated with 10 adults. Treated rice plants are kept at about 28-29° C. and relative humidity of about 50-60%. Percent mortality is recorded after 72 hours.

B.2 Rice Brown Plant Hopper (*Nilaparvata lugens*):

Rice seedlings are cleaned and washed 24 hours before spraying. The active compounds are formulated in 50:50 acetone:water (vol:vol) and 0.1% vol/vol surfactant (EL 620) is added. Potted rice seedlings are sprayed with 5 ml test solution, air dried, placed in cages and inoculated with 10 adults. Treated rice plants are kept at about 28-29° C. and relative humidity of about 50-60%. Percent mortality is recorded after 72 hours.

B.3 Cowpea aphid (*Aphis craccivora*):

For evaluating control of Cowpea aphid through contact or systemic means the test unit consists of 24-well-microtiter plates containing broad bean leaf disks.

The compounds are formulated using a solution containing 75% v/v water and 25% v/v DMSO. Different concentrations of formulated compounds are sprayed onto the leaf disks at 2.5 µl, using a custom built micro atomizer, at two replications.

After application, the leaf disks are air-dried and 5-8 adult aphids placed on the leaf disks inside the microtiter plate wells. The aphids are then allowed to suck on the treated leaf disks and incubated at about 23±1° C. and about 50±5% relative humidity for 5 days. Aphid mortality and fecundity is then visually assessed.

B.4 *Thrips* (*Dichromothrips Corbetti*):

*Dichromothrips corbetti* adults used for bioassay are obtained from a colony maintained continuously under laboratory conditions. For testing purposes, the test compound is diluted in a 1:1 mixture of acetone:water (vol:vol), plus 0.01% vol/vol Alkamuls® EL 620 surfactant.

*Thrips* potency of each compound is evaluated by using a floral-immersion technique. Plastic petri dishes are used as test arenas. All petals of individual, intact orchid flowers are dipped into treatment solution and allowed to dry. Treated flowers are placed into individual petri dishes along with about 20 adult *thrips*. The petri dishes v then covered with lids. All test arenas are held under continuous light and a temperature of about 28° C. for duration of the assay. After 3 days, the numbers of live *thrips* are counted on each flower, and along inner walls of each petri dish. The percent mortality is recorded 72 hours after treatment.

Tables A below shows activity data:

TABLE A

| | | Test species | | | |
|---|---|---|---|---|---|
| Compound | Dose (ppm) | Cowpea aphid | Rice green leafhopper | Rice brown plant hopper | Thrips |
| | | Mortality % | | | |
| I-1 (racemic mixture) | 1 | 80 | 50 | 54 | — |
| I-R-1 | 1 | 90 | 100 | 90 | — |
| I-S-1 | 1 | 0 | 0 | 0 | — |
| I-1 (racemic mixture) | 10 | — | — | — | 73 |
| | | Test species | | | |
| I-R-1 | 10 | — | — | — | 100 |
| I-S-1 | 10 | — | — | — | 0 |

B.3. Rice Stem Borer

B.3a Vial Bioassays

Field-collected rice straws were washed with tap water and cut for a certain of length. Straws were air dried before placing individually in vials (=replicate, 3×). About 125 µl test solution was sprayed per vial. Treated rice straws in vials were air dried under the laboratory hood. After air-drying, each straw was inoculated with 10 newly-emerged (0-day old) stem borer larvae. Vials were then covered. Set-up was kept in a holding room maintained at 27° C. and 65% RH for three days. At 3 days after inoculation, rice straws were manually dissected for larval mortality assessment. The data (Table C) show activity against two species of rice stem borers.

TABLE C

Efficacy of mesoionic compounds against rice stem borers

| Test species | | *Chilo suppressalis* |
|---|---|---|
| Life stage | | $1^{st}$ instar |
| Evaluation | | 3 DAT/3 DAI |
| compound | Dose (ppm) | Mortality (%) |
| I-1 (racemic mixture) | 300 | 80 |
| I-R-1 | 300 | 83 |

B.3b Foliar Spraying

All three pots (=replicates) of four to five-week old potted rice per treatment were simultaneously sprayed with 12 mL test solution. After spray application, plants were air dried in the laboratory before inoculation. After air-drying, 5 to 6-day old egg masses of CHILSU were used for inoculation. All stem borer-infested potted rice plants were transferred inside the screenhouse 1 day after inoculation until the final assessment. Assessment was done 10 days after treatment and inoculation. Whole plant damage was assessed before cutting each hill at the basal portion for tiller dissection. Each dissected tiller was inspected looking for dead (if possible) and alive stemborer larvae.

The results showed that the tested compound have excellent activity against striped rice stem borer in terms of larvae mortality and feed suppression

TABLE D

Efficacy of mesoionic compounds against rice striped stem borer by foliar spraying

| Test species | | *Chilo suppressalis* | |
|---|---|---|---|
| Life stage | | Neonates | |
| Evaluation | | 14 DAT | |
| compound | Dose (ppm) | Mortality (%) | Feeding damage (%) |
| I-1 (racemic mixture) | 200 | 96 | 15 |
| I-R-1 | 200 | 99 | 7 |

B.3c Drench Application

The test solution was poured onto the soil of each potted rice plant (=replicate) with five tillers each pot. After drench application, treated plants were transferred inside the screenhouse for three days prior to stemborer inoculation inside the laboratory. Three days after drench application, 5 to 6-day old egg masses of CHILSU were used for inoculation. All stemborer-infested potted rice plants were transferred inside the screenhouse 1 day after inoculation until the final assessment. Assessment was done 12 days after treatment (9 days after inoculation). Whole plant damage was assessed before cutting each hill at the basal portion for tiller dissection. Each dissected tiller was inspected looking for dead (if possible) and alive stemborer larvae.

The data (Table 3) showed that similar results were obtained through drench application when compared with foliar application for all tested compound against striped rice stem borer in terms of larvae mortality and feed suppression

TABLE E

Efficacy of mesoionic compounds against rice striped stem borer by drench application

| Test species | Chilo suppressalis | |
|---|---|---|
| Life stage | Neonates | |
| Evaluation | 14 DAT | |

| compound | Dose (mg) | Mortality (%) | Feeding damage (%) |
|---|---|---|---|
| I-1 (racemic mixture) | 10 | 96 | 15 |
| I-R-1 | 10 | 99 | 7 |

Examples of Mixtures:

Synergism can be described as an interaction where the combined effect of two or more compounds is greater than the sum of the individual effects of each of the compounds. The presence of a synergistic effect in terms of percent control, between two mixing partners (X and Y) can be calculated using the Colby equation (Colby, S. R., 1967, Calculating Synergistic and Antagonistic Responses in Herbicide Combinations, *Weeds*, 15, 20-22):

$$E = X + Y - \frac{XY}{100}$$

When the observed combined control effect is greater than the expected combined control effect (E), then the combined effect is synergistic.

The following tests demonstrate the control efficacy of compounds, mixtures or compositions of this invention on specific pests, wherein the compound I-R-1 is in 95% enantiomeric excess unless otherwise specified. However, the pest control protection afforded by the compounds, mixtures or compositions is not limited to these species. In certain instances, combinations of a compound of this invention with other invertebrate pest control compounds or agents are found to exhibit synergistic effects against certain important invertebrate pests.

The analysis of synergism or antagonism between the mixtures or compositions was determined using Colby's equation.

Test 1

For evaluating control of vetch aphid (*Megoura viciae*) through contact or systemic means the test unit consisted of 24-well-microtiter plates containing broad bean leaf disks.

The compounds or mixtures were formulated using a solution containing 75% water and 25% DMSO. Concentrations of formulated compounds or mixtures were sprayed onto the leaf disks at 2.5 µl, using a custom built micro atomizer, at two replications.

For experimental mixtures in these tests identical volumes of both mixing partners at the desired concentrations respectively, were mixed together.

After application, the leaf disks were air-dried and 5-8 adult aphids placed on the leaf disks inside the microtiter plate wells. The aphids were then allowed to suck on the treated leaf disks and incubated at 23±1° C., 50±5% RH for 5 days. Aphid mortality and fecundity was then visually assessed. For the mixture tested the results are listed in table 1.

TABLE 1

I-R-1 and Spinetoram.

| | solo application | | | | combination | |
|---|---|---|---|---|---|---|
| | Spinetoram | | I-R-1 | | Spinetoram + I-R-1 | |
| insect | use rate (ppm) | Average control % | use rate (ppm) | Average control % | use rate (ppm) | Average control % |
| Vetch Aphid | 2 | 50 | 20 | 0 | 20 + 2 | 100 |

Test 2

For evaluating control of green peach aphid (*Myzus persicae*) through systemic means the test unit consisted of 96-well-microtiter plates containing liquid artificial diet under an artificial membrane.

The compounds or mixtures were formulated using a solution containing 75% water and 25% DMSO. Concentrations of formulated compounds or mixtures were pipetted into the aphid diet, using a custom built pipetter, at two replications.

For experimental mixtures in these tests identical volumes of both mixing partners at the desired concentrations respectively, were mixed together.

After application, 5-8 adult aphids were placed on the artificial membrane inside the microtiter plate wells. The aphids were then allowed to suck on the treated aphid diet and incubated at 23±1° C., 50±5% RH for 3 days. Aphid mortality and fecundity was then visually assessed.

For the mixture tested the results are listed in tables 2.1 to 2.6.

TABLE 2.1

I-R-1 and Spinosad.

| | solo application | | | | combination | |
|---|---|---|---|---|---|---|
| | Spinosad | | I-R-1 | | Spinosad + I-R-1 | |
| insect | use rate (ppm) | Average control % | use rate (ppm) | Average control % | use rate (ppm) | Average control % |
| Green Peach Aphid | 4 | 0 | 2 | 25 | 4 + 2 | 100 |

TABLE 2.2

I-R-1 and Flufenoxuron.

| | solo application | | | | combination | |
|---|---|---|---|---|---|---|
| | Flufenoxuron | | I-R-1 | | Flufenoxuron + I-R-1 | |
| insect | use rate (ppm) | Average control % | use rate (ppm) | Average control % | use rate (ppm) | Average control % |
| Green Peach Aphid | 0.8 | 0 | 2 | 0 | 0.8 + 2 | 100 |

TABLE 2.3

I-R-1 and Triflumezopyrim.

| | solo application | | | | combination | |
|---|---|---|---|---|---|---|
| | Triflumezopyrim | | I-R-1 | | Triflumezopyrim + I-R-1 | |
| insect | use rate (ppm) | Average control % | use rate (ppm) | Average control % | use rate (ppm) | Average control % |
| Green Peach Aphid | 0.4 | 0 | 0.4 | 50 | 0.4 + 0.4 | 100 |

TABLE 2.4

I-R-1 and Indoxacarb.

| | solo application | | | | combination | |
|---|---|---|---|---|---|---|
| | Indoxacarb | | I-R-1 | | Indoxacarb + I-R-1 | |
| insect | use rate (ppm) | Average control % | use rate (ppm) | Average control% | use rate (ppm) | Average control % |
| Green Peach Aphid | 2 | 0 | 50 | 0 | 2 + 2 | 100 |

TABLE 2.5

I-R-1 and Flonicamid.

| | solo application | | | | combination | |
|---|---|---|---|---|---|---|
| | Flonicamid | | I-R-1 | | Flonicamid + I-R-1 | |
| insect | use rate (ppm) | Average control % | use rate (ppm) | Average control % | use rate (ppm) | Average control % |
| Green Peach Aphid | 2 | 0 | 2 | 50 | 2 + 2 | 100 |

TABLE 2.6

I-R-1 and Alpha-Cypermethrin.

| | solo application | | | | combination | |
|---|---|---|---|---|---|---|
| | Alpha-Cypermethrin | | I-R-1 | | Alpha-Cypermethrin + I-R-1 | |
| insect | use rate (ppm) | Average control % | use rate (ppm) | Average control % | use rate (ppm) | Average control % |
| Green Peach Aphid | 10 | 0 | 2 | 25 | 10 + 2 | 100 |

Test 3

For evaluating control of boll weevil (*Anthonomus grandis*) the test unit consisted of 24-well-microtiter plates containing an insect diet and 20-30 *A. grandis* eggs.

The compounds or mixtures were formulated using a solution containing 75% water and 25% DMSO. Concentrations of formulated compounds or mixtures were sprayed onto the insect diet at 20 µl, using a custom built micro atomizer, at two replications.

For experimental mixtures in these tests identical volumes of both mixing partners at the desired concentrations respectively, were mixed together.

After application, microtiter plates were incubated at 23±1° C., 50±5% RH for 5 days. Egg and larval mortality was then visually assessed. For the mixture tested the results are listed in table 3.1 to table 3.3.

TABLE 3.1

I-R-1 and Flufenoxuron.

| | solo application | | | | combination | |
|---|---|---|---|---|---|---|
| | Flufenoxuron | | I-R-1 | | Flufenoxuron + I-R-1 | |
| insect | use rate (ppm) | Average control % | use rate (ppm) | Average control % | use rate (ppm) | Average control % |
| Boll Weevil | 0.8 | 0 | 50 | 0 | 0.8 + 50 | 75 |

TABLE 3.2

I-R-1 and Spinetoram.

| | solo application | | | | combination | |
|---|---|---|---|---|---|---|
| | Spinetoram | | I-R-1 | | Spinetoram + I-R-1 | |
| insect | use rate (ppm) | Average control % | use rate (ppm) | Average control % | use rate (ppm) | Average control % |
| Boll Weevil | 4 | 0 | 2 | 0 | 4 + 2 | 100 |

TABLE 3.3

I-R-1 and Fluxametamide.

| | solo application | | | | combination | |
|---|---|---|---|---|---|---|
| | Fluxametamide | | I-R-1 | | Fluxametamide + I-R-1 | |
| insect | use rate (ppm) | Average control % | use rate (ppm) | Average control % | use rate (ppm) | Average control % |
| Boll Weevil | 0.4 | 25 | 2 | 0 | 0.4 + 2 | 100 |

Test 4

For evaluating control of tobacco budworm (*Heliothis virescens*) the test unit consisted of 96-well-microtiter plates containing an insect diet and 15-25 *H. virescens* eggs.

The compounds or mixtures were formulated using a solution containing 75% water and 25% DMSO. Concentrations of formulated compounds or mixtures were sprayed onto the insect diet at 10 µl, using a custom built micro atomizer, at two replications.

For experimental mixtures in these tests identical volumes of both mixing partners at the desired concentrations respectively, were mixed together.

After application, microtiter plates were incubated at 28±1° C., 80±5% RH for 5 days. Egg and larval mortality was then visually assessed. For the mixture tested the results are listed in tables 4.1 and 4.2.

TABLE 4.1

| | I-R-1 and Pymetrozine. | | | | | |
|---|---|---|---|---|---|---|
| | solo application | | | | combination | |
| | Pymetrozine | | I-R-1 | | Pymetrozine + I-R-1 | |
| insect | use rate (ppm) | Average control % | use rate (ppm) | Average control % | use rate (ppm) | Average control % |
| Tobacco budworm | 10 | 0 | 10 | 0 | 10 + 10 | 50 |

TABLE 4.2

| | I-R-1 and Alpha-Cypermethrin. | | | | | |
|---|---|---|---|---|---|---|
| | solo application | | | | combination | |
| | Alpha-Cypermethrin | | I-R-1 | | Alpha-Cypermethrin + I-R-1 | |
| insect | use rate (ppm) | Average control % | use rate (ppm) | Average control % | use rate (ppm) | Average control % |
| Tobacco budworm | 2 | 50 | 0.4 | 0 | 2 + 0.4 | 100 |

For evaluating control of Greenhouse Whitefly (*Trialeurodes vaporariorum*) the test unit consisted of 96-well-microtiter plates containing a leaf disk of egg plant leaf disk with white fly eggs. The compounds or mixtures were formulated using a solution containing 75% water and 25% DMSO. Concentrations of formulated compounds or mixtures were sprayed onto the insect diet at 2.5 µl, using a custom built micro atomizer, at two replications.

For experimental mixtures in these tests identical volumes of both mixing partners at the desired concentrations respectively, were mixed together.

After application, microtiter plates were incubated at 23±1° C., 65±5% RH for 6 days. Mortality of hatched crawlers was then visually assessed. For the mixture tested the results are listed in table 5.

TABLE 5

| | I-R-1 and Oxazosulfyl. | | | | | |
|---|---|---|---|---|---|---|
| | solo application | | | | combination | |
| | Oxazosulfyl | | I-R-1 | | Oxazosulfyl + I-R-1 | |
| insect | use rate (ppm) | Average control % | use rate (ppm) | Average control % | use rate (ppm) | Average control % |
| Greenhouse Whitefly | 50 | 50 | 2 | 0 | 50 + 2 | 100 |

Test 6:

For evaluating control of brown planthopper (*Nilaparvata lugens*) by foliar spray method. Clean potted rice seedlings with upper leaf portion cut are properly labeled. Placed three potted rice plants per treatment concentration/combination on top of the rotating disc (270 mm) and sprayed with the 12 mL spray solution. Treated plants are allowed to air-dry in the laboratory for about an hour. After air-drying, covered each treated rice plant. Each treated plant was infested with brown planthoppers using a suction vacuum. Plants are maintained at 27° C.±1° C., 50±5% RH and 24 hours light conditions in a holding room. Percent mortality is recorded 7 days after infestation by counting both the dead and alive brown planthoppers on the plants and on the water. The average control after 7 days of compounds and mixtures tested are given in table 6.1 to 6.2.

TABLE 6.1

I-R-1 and Pymetrozine.

| | solo application | | | | combination | |
|---|---|---|---|---|---|---|
| | Pymetrozine | | I-R-1 | | Pymetrozine + I-R-1 | |
| insect | use rate (ppm) | Average control % | use rate (ppm) | Average control % | use rate (ppm) | Average control % |
| brown planthopper | 300 | 26 | 5 | 62 | 300 + 5 | 85 |

TABLE 6.2

I-R-1 and Spinetoram.

| | solo application | | | | combination | |
|---|---|---|---|---|---|---|
| | Spinetoram | | I-R-1 | | Spinetoram + I-R-1 | |
| insect | use rate (ppm) | Average control % | use rate (ppm) | Average control % | use rate (ppm) | Average control % |
| brown planthopper | 70 | 62 | 5 | 62 | 70 + 5 | 100 |

Test 7:

For evaluating control of vetch aphid (*Megoura viciae*) through contact or systemic means the test unit consisted of 24-well-microtiter plates containing broad bean leaf disks.

The compounds or mixtures were formulated using a solution containing 75% water and 25% DMSO. Concentrations of formulated compounds or mixtures were sprayed onto the leaf disks at 2.5 µl, using a custom built micro atomizer, at two replications.

For experimental mixtures in these tests identical volumes of both mixing partners at the desired concentrations respectively, were mixed together.

After application, the leaf disks were air-dried and 5-8 adult aphids placed on the leaf disks inside the microtiter plate wells. The aphids were then allowed to suck on the treated leaf disks and incubated at 23±1° C., 50±5% RH for 5 days. Aphid mortality and fecundity was then visually assessed. For the mixture tested the results are listed in tables 7.1 and 7.2.

TABLE 7.1

| | solo application | | | | combination | |
|---|---|---|---|---|---|---|
| | Furametpyr | | I-R-1 | | Furametpyr + I-R-1 | |
| insect | use rate (ppm) | Average control % | use rate (ppm) | Average control % | use rate (ppm) | Average control % |
| Vetch Aphid | 2500 | 0 | 2 | 25 | 2500 + 2 | 75 |

TABLE 7.2

| insect | solo application | | | | combination | |
|---|---|---|---|---|---|---|
| | Metalaxyl | | I-R-1 | | Metalaxyl + I-R-1 | |
| | use rate (ppm) | Average control % | use rate (ppm) | Average control % | use rate (ppm) | Average control % |
| Vetch Aphid | 2500 | 0 | 2 | 25 | 2500 + 2 | 50 |

Test 8:
For evaluating control of green peach aphid (*Myzus persicae*) through systemic means the test unit consisted of 96-well-microtiter plates containing liquid artificial diet under an artificial membrane.

The compounds or mixtures were formulated using a solution containing 75% water and 25% DMSO. Concentrations of formulated compounds or mixtures were pipetted into the aphid diet, using a custom built pipetter, at two replications.

For experimental mixtures in these tests identical volumes of both mixing partners at the desired concentrations respectively, were mixed together.

After application, 5-8 adult aphids were placed on the artificial membrane inside the microtiter plate wells. The aphids were then allowed to suck on the treated aphid diet and incubated at 23±1° C., 50±5% RH for 3 days. Aphid mortality and fecundity was then visually assessed. For the mixture tested the results are listed in tables 8.1 and 8.2.

TABLE 8.1

| insect | solo application | | | | combination | |
|---|---|---|---|---|---|---|
| | Probenazole | | I-R-1 | | Probenazole + I-R-1 | |
| | use rate (ppm) | Average control % | use rate (ppm) | Average control % | use rate (ppm) | Average control % |
| Green Peach Aphid | 500 | 0 | 0.4 | 0 | 500 + 0.4 | 75 |

TABLE 8.2

| insect | solo application | | | | combination | |
|---|---|---|---|---|---|---|
| | Dicyclomet | | I-R-1 | | Dicyclomet + I-R-1 | |
| | use rate (ppm) | Average control % | use rate (ppm) | Average control % | use rate (ppm) | Average control % |
| Green Peach Aphid | 2500 | 0 | 0.4 | 0 | 2500 + 0.4 | 75 |

Test 9:
For evaluating control of boll weevil (*Anthonomus grandis*) the test unit consisted of 24-well-microtiter plates containing an insect diet and 20-30 *A. grandis* eggs.

The compounds or mixtures were formulated using a solution containing 75% water and 25% DMSO. Concentrations of formulated compounds or mixtures were sprayed onto the insect diet at 20 µl, using a custom built micro atomizer, at two replications.

For experimental mixtures in these tests identical volumes of both mixing partners at the desired concentrations respectively, were mixed together.

After application, microtiter plates were incubated at 23±1° C., 50±5% RH for 5 days. Egg and larval mortality was then visually assessed. For the mixture tested the results are listed in tables 9.1 and 9.2.

TABLE 9.1

| insect | solo application | | | | combination | |
|---|---|---|---|---|---|---|
| | Penflufen | | I-R-1 | | Penflufen + I-R-1 | |
| | use rate (ppm) | Average control % | use rate (ppm) | Average control % | use rate (ppm) | Average control % |
| Boll Weevil | 2500 | 0 | 50 | 25 | 2500 + 50 | 50 |

TABLE 9.2

| insect | solo application | | | | combination | |
| --- | --- | --- | --- | --- | --- | --- |
| | Metalaxyl | | I-R-1 | | Metalaxyl + I-R-1 | |
| | use rate (ppm) | Average control % | use rate (ppm) | Average control % | use rate (ppm) | Average control % |
| Boll Weevil | 500 | 0 | 10 | 25 | 500 + 10 | 50 |

Test 10:
For evaluating control of tobacco budworm (*Heliothis virescens*) the test unit consisted of 96-well-microtiter plates containing an insect diet and 15-25 *H. virescens* eggs.

The compounds or mixtures were formulated using a solution containing 75% water and 25% DMSO. Different concentrations of formulated compounds or mixtures were sprayed onto the insect diet at 10 μl, using a custom built micro atomizer, at two replications.

For experimental mixtures in these tests identical volumes of both mixing partners at the desired concentrations respectively, were mixed together.

After application, microtiter plates were incubated at 28±1° C., 80±5% RH for 5 days. Egg and larval mortality was then visually assessed. For the mixture tested the results are listed in tables 10.1 and 10.2.

TABLE 10.1

| insect | solo application | | | | combination | |
| --- | --- | --- | --- | --- | --- | --- |
| | Probenazole | | I-R-1 | | Probenazole + I-R-1 | |
| | use rate (ppm) | Average control % | use rate (ppm) | Average control % | use rate (ppm) | Average control % |
| Tobacco budworm | 2500 | 0 | 10 | 0 | 2500 + 10 | 50 |

TABLE 10.2

| insect | solo application | | | | combination | |
| --- | --- | --- | --- | --- | --- | --- |
| | Pyroquilon | | I-R-1 | | Pyroquilon + I-R-1 | |
| | use rate (ppm) | Average control % | use rate (ppm) | Average control % | use rate (ppm) | Average control % |
| Tobacco budworm | 2500 | 0 | 10 | 25 | 2500 + 10 | 50 |

Test 11:
For evaluating control of Greenhouse Whitefly (*Trialeurodes vaporariorum*) the test unit consisted of 96-well-microtiter plates containing a leaf disk of egg plant leaf disk with white fly eggs.

The compounds or mixtures were formulated using a solution containing 75% water and 25% DMSO. Different concentrations of formulated compounds or mixtures were sprayed onto the insect diet at 2.5 μl, using a custom built micro atomizer, at two replications.

For experimental mixtures in these tests identical volumes of both mixing partners at the desired concentrations respectively, were mixed together.

After application, microtiter plates were incubated at 23±1° C., 65±5% RH for 6 days. Mortality of hatched crawlers was then visually assessed. For the mixture tested the results are listed in tables 11.1 and 11.2.

TABLE 11.1

| insect | solo application | | | | combination | |
| --- | --- | --- | --- | --- | --- | --- |
| | Simeconazol | | I-R-1 | | Simeconazol + I-R-1 | |
| | use rate (ppm) | Average control % | use rate (ppm) | Average control % | use rate (ppm) | Average control % |
| Greenhouse Whitefly | 2500 | 0 | 50 | 25 | 2500 + 50 | 100 |

TABLE 11.2

| | solo application | | | | combination | |
|---|---|---|---|---|---|---|
| | Buprofezin | | I-R-1 | | Buprofezin + I-R-1 | |
| insect | use rate (ppm) | Average control % | use rate (ppm) | Average control % | use rate (ppm) | Average control % |
| Greenhouse Whitefly | 2500 | 50 | 10 | 0 | 2500 + 10 | 100 |

Test 12:

For evaluating control of yellow fever mosquito (*Aedes aegypti*) the test unit consisted of 96-well-microtiter plates containing 200 μl of tap water per well and 5-15 freshly hatched *A. aegypti* larvae.

The compounds or mixtures were formulated using a solution containing 75% water and 25% DMSO. Different concentrations of formulated compounds or mixtures were sprayed onto the insect diet at 2.5 μl, using a custom built micro atomizer, at two replications.

For experimental mixtures in these tests identical volumes of both mixing partners at the desired concentrations respectively, were mixed together.

After application, microtiter plates were incubated at 28±1° C., 80±5% RH for 2 days. Larval mortality was then visually assessed. For the mixture tested the results are listed in tables 12.

TABLE 12

| | solo application | | | | combination | |
|---|---|---|---|---|---|---|
| | Tricyclazol | | I-R-1 | | Tricyclazol + I-R-1 | |
| insect | use rate (ppm) | Average control % | use rate (ppm) | Average control % | use rate (ppm) | Average control % |
| Yellow Fever Mosquito | 2500 | 50 | 10 | 0 | 2500 + 10 | 100 |

The invention claimed is:

1. A mixture comprising:
   (1) a compound of formula I-R-1 or a salt thereof:

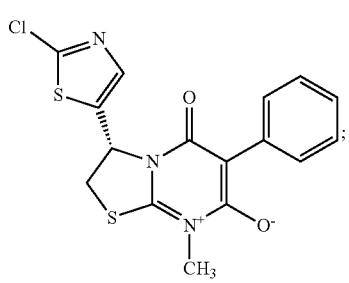

(I-R-1)

and (2) at least one compound II selected from the group consisting of spinetoram, spinosad, flufenoxuron, triflumezopyrim, indoxacarb, flonicamid, alpha-cypermethrin, fluxametamide, pymetrozine, oxazosulfyl, furametpyr, metalaxyl, probenazole, dicyclomet, penflufen, pyroquilon, simeconazol, buprofezin, tricyclazol, and combinations thereof;

wherein:
the ratio of the compound of formula I-R-1 and the compound II is between 1000:1 to 1:1000; and
an enantiomeric excess between the compound of formula I-R-1 and any corresponding S-enantiomer in the mixture is at least 90%.

2. The mixture of claim 1, wherein the ratio of the compound of formula I-R-1 and the compound II is between 100:1 and 1:100.

3. The mixture of claim 1, wherein the enantiomeric excess between the compound of formula I-R-1 and any corresponding S-enantiomer in the mixture is at least 95%.

4. The mixture of claim 1, wherein the enantiomeric excess between the compound of formula I-R-1 and any corresponding S-enantiomer in the mixture is at least 98%.

5. A pesticidal composition comprising a liquid or solid carrier and the mixture of claim 1.

6. A seed comprising the mixture of claim 1 in an amount of from 0.1 g to 10 kg per 100 kg of seeds.

7. A method for controlling insects, acarids or nematodes comprising contacting an insect, acarid or nematode or their food supply, habitat, breeding grounds or their locus with the mixture of claim 1.

8. A method of protecting plants from attack or infestation by insects, acarids or nematodes comprising contacting the plant, or soil or water in which the plant is growing, with a pesticidally effective amount of the mixture of claim 1.

9. A method for protection of plant propagation material comprising contacting the plant propagation material with the mixture of claim 1 in pesticidally effective amounts.

10. The method of claim 8, wherein the plant is a rice plant and the insects are selected from the group consisting of Hemiptera, Lepidoptera, Coleoptera, *Diptera*, Thysanoptera, Orthoptera, Isoptera, Hymenoptera, Acari, and Crustacea.

* * * * *